United States Patent
Amalfitano et al.

(10) Patent No.: US 10,752,902 B2
(45) Date of Patent: Aug. 25, 2020

(54) COMPOSITIONS COMPRISING FUSION PROTEINS USEFUL FOR MODULATING AN IMMUNE RESPONSE

(71) Applicant: Board of Trustees of Michigan State University, East Lansing, MI (US)

(72) Inventors: Andrea Amalfitano, East Lansing, MI (US); Yasser A. Aldhamen, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 173 days.

(21) Appl. No.: 15/513,660

(22) PCT Filed: Sep. 22, 2015

(86) PCT No.: PCT/US2015/051442
§ 371 (c)(1),
(2) Date: Mar. 23, 2017

(87) PCT Pub. No.: WO2016/049022
PCT Pub. Date: Mar. 31, 2016

(65) Prior Publication Data
US 2017/0292127 A1    Oct. 12, 2017

Related U.S. Application Data

(60) Provisional application No. 62/054,133, filed on Sep. 23, 2014.

(51) Int. Cl.
*C07K 19/00* (2006.01)
*C07K 14/47* (2006.01)
*C12N 15/117* (2010.01)
*C07K 14/705* (2006.01)
*A61K 38/02* (2006.01)
*A61K 38/17* (2006.01)
*A61K 39/00* (2006.01)

(52) U.S. Cl.
CPC ............ *C12N 15/117* (2013.01); *A61K 38/02* (2013.01); *A61K 38/177* (2013.01); *C07K 14/70507* (2013.01); *A61K 2039/5154* (2013.01); *A61K 2039/6056* (2013.01)

(58) Field of Classification Search
None
See application file for complete search history.

(56) References Cited

U.S. PATENT DOCUMENTS

2005/0025763 A1 * 2/2005 Williams ......... C07K 14/70507
424/144.1
2011/0159021 A1   6/2011 Munshi et al.

FOREIGN PATENT DOCUMENTS

WO    WO-2014/071402 A1    5/2014

OTHER PUBLICATIONS

Rudikoff et al. (Proceedings of the National Academy of Sciences USA, vol. 79, pp. 1979-1983, 1982) (Year: 1982).*
Bae et al., "A novel immunogenic CS1-specific peptide inducing antigen-specific cytotoxic T lymphocytes targeting multiple myeloma," Br J Haematol, 157(6): 687-701 (2012).
International Search Report and Written Opinion for International Application No. PCT/US2015/051442 dated Feb. 1, 2016.
Tai et al., "Anti-CS1 humanized monoclonal antibody HuLuc63 inhibits myeloma cell adhesion and induces antibody-dependent cellular cytotoxicity in the bone marrow milieu," Blood, 112(4): 1329-1337 (2007).

* cited by examiner

*Primary Examiner* — Michael Allen
(74) *Attorney, Agent, or Firm* — Foley Hoag LLP

(57) ABSTRACT

The disclosure relates to, among other things, agents that modulate the homophilic interaction between two CRACC polypeptides, methods for making such agents, and therapeutic applications in which the agents are useful. For example, the agents described herein are useful for modulating an immune response in a mammal. Also featured are screening methods for identifying additional agents capable of modulating the activation of an immune cell exposed to an antigen.

3 Claims, 37 Drawing Sheets

Specification includes a Sequence Listing.

5A
5B

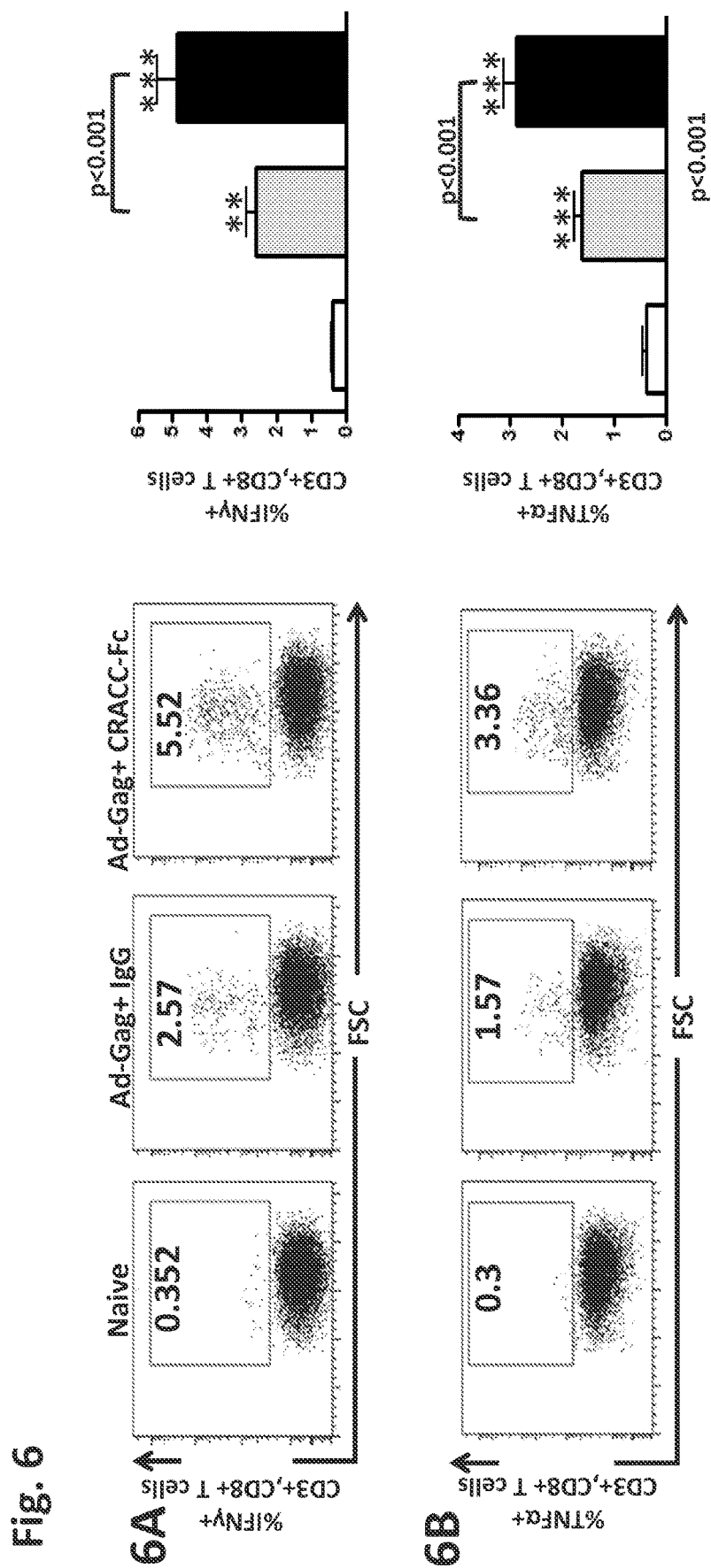

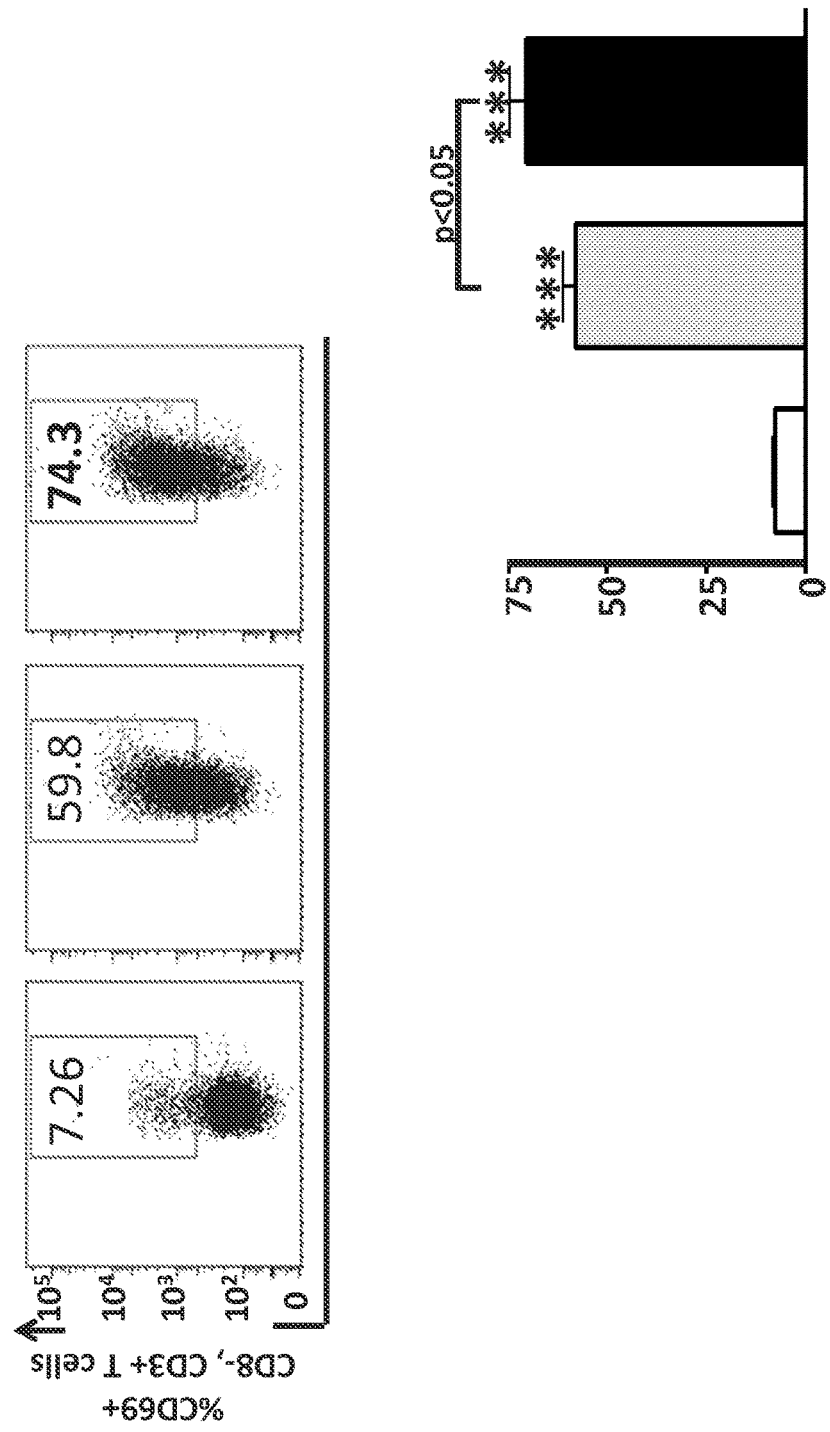

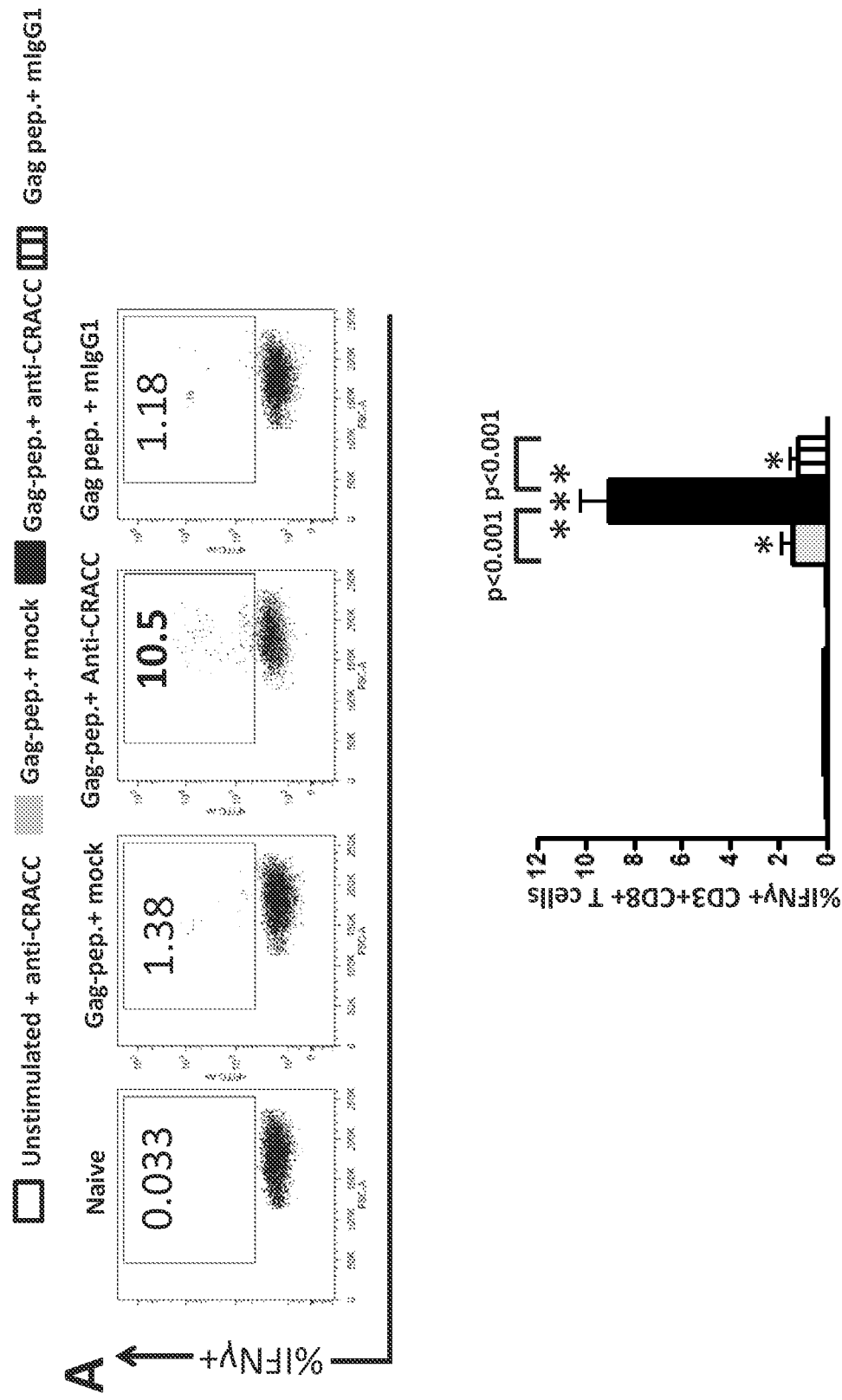
Fig.: 13A

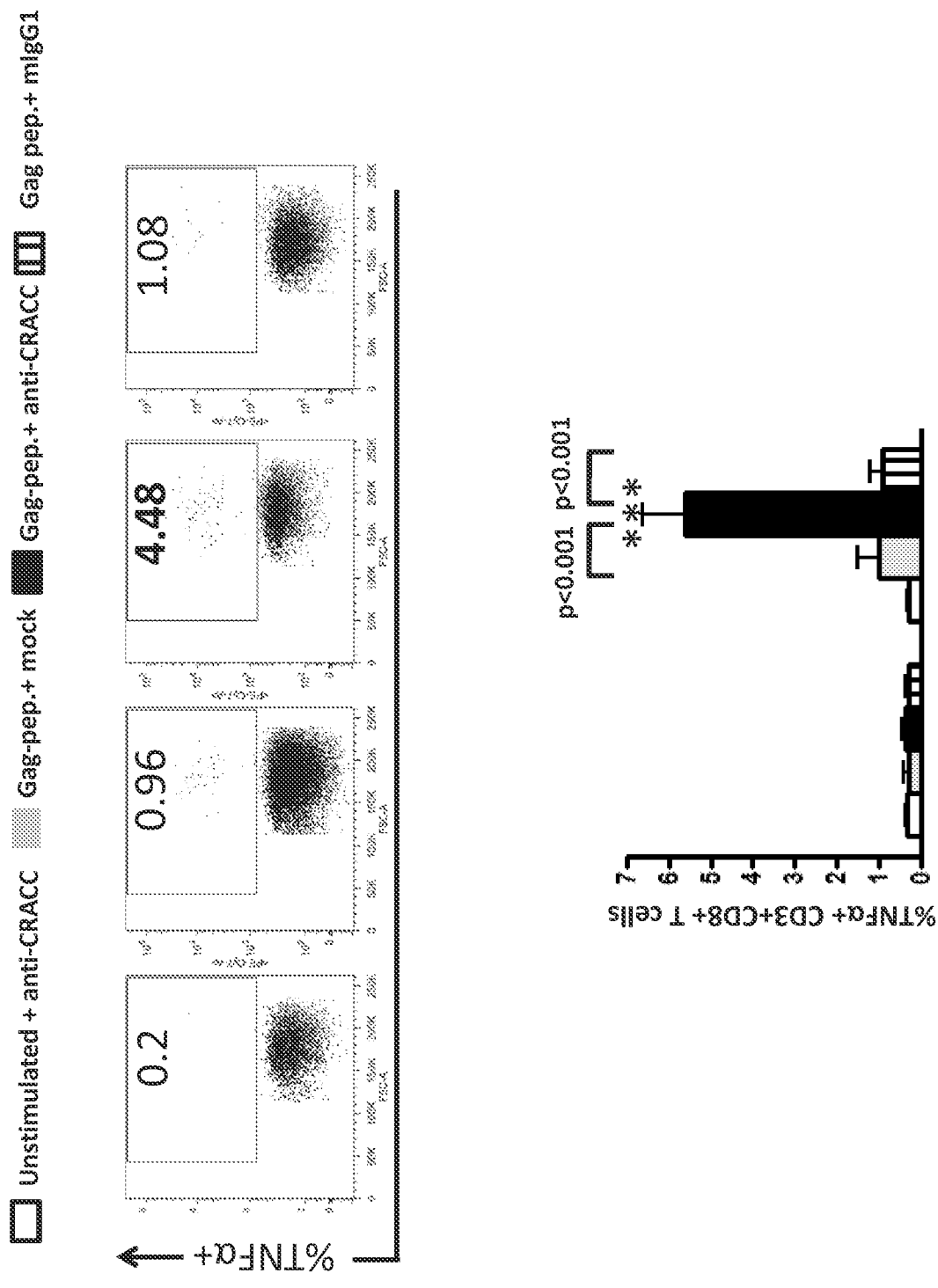
Fig.: 13B

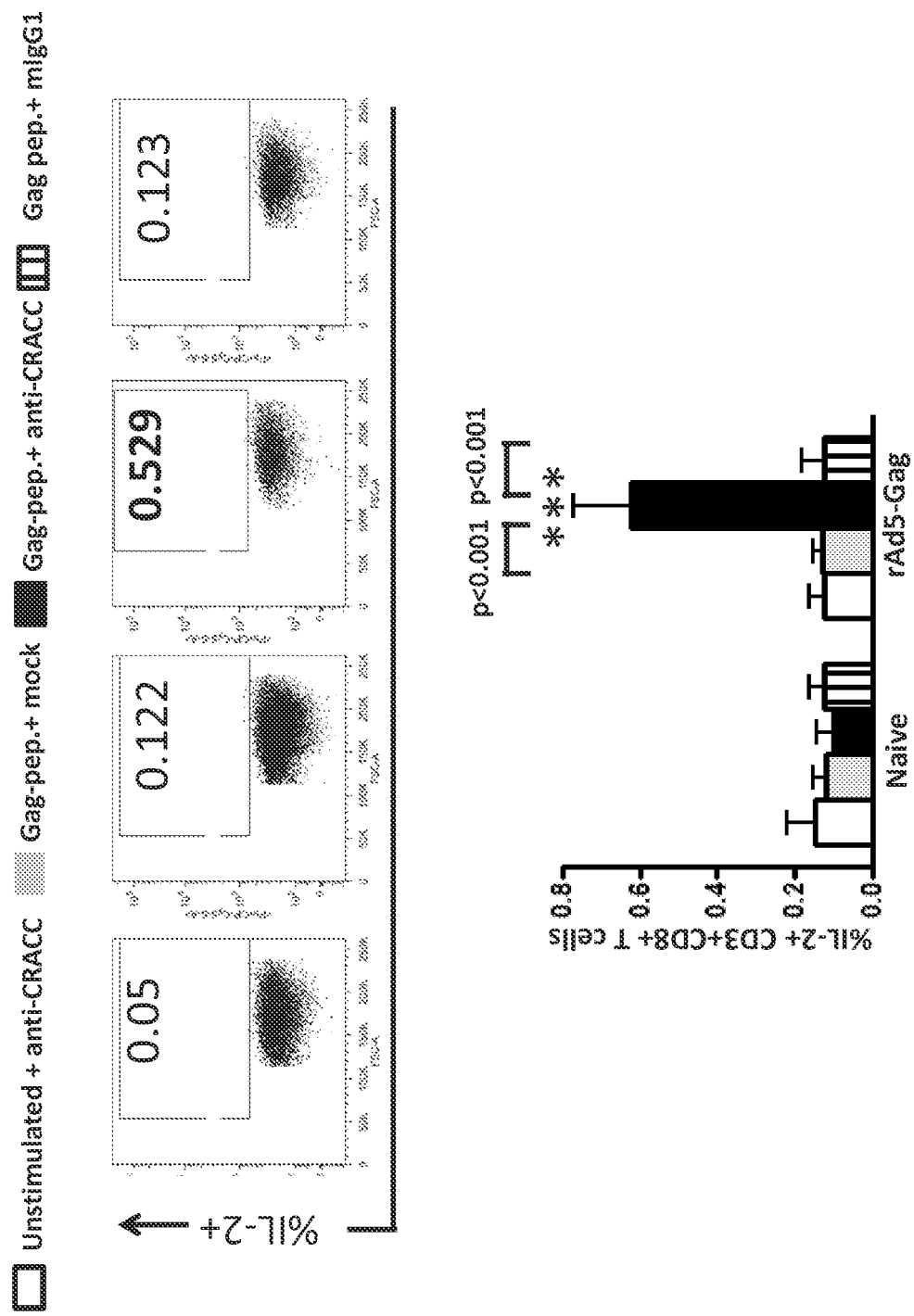
Fig.: 13C

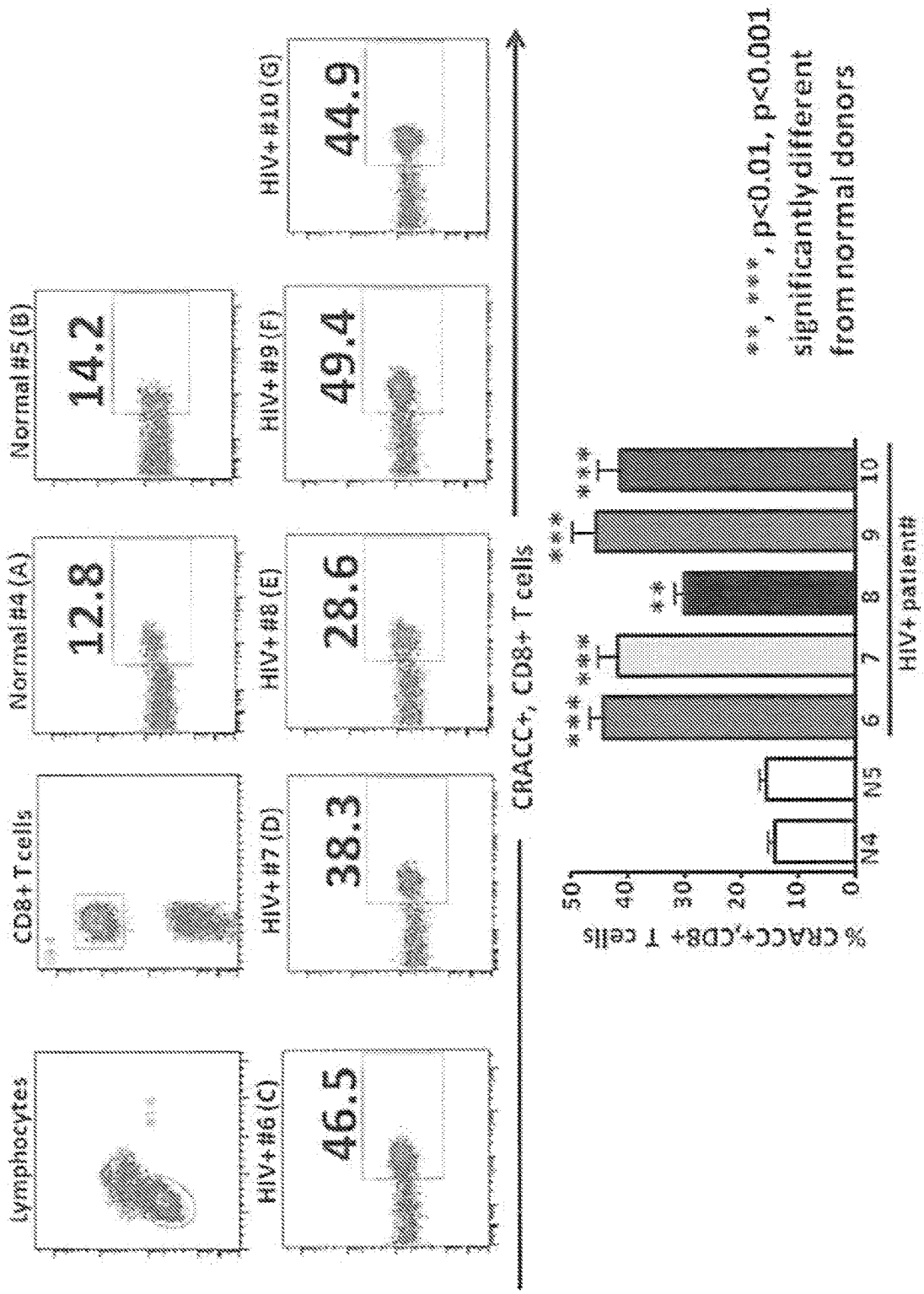
Fig.: 14

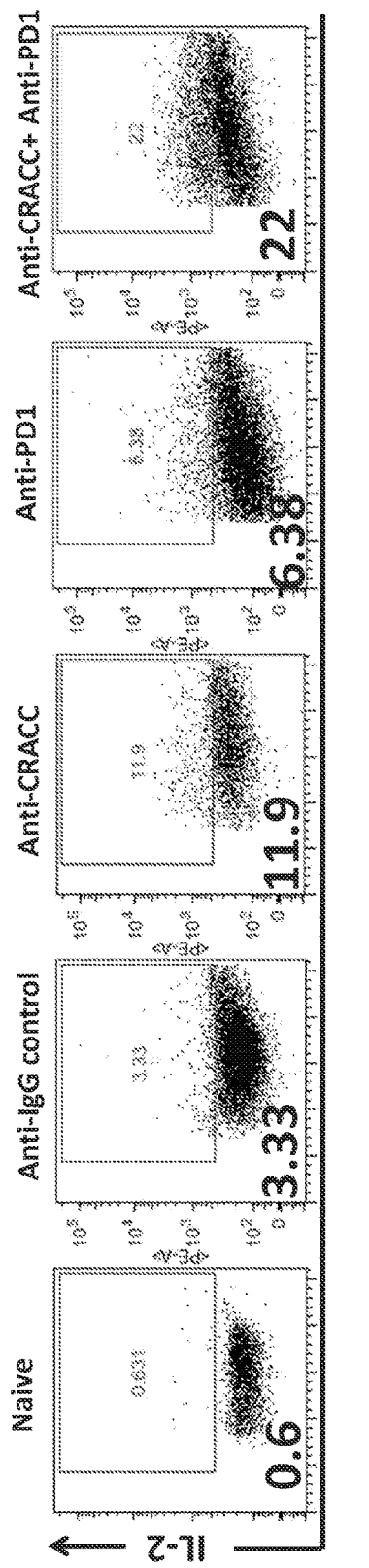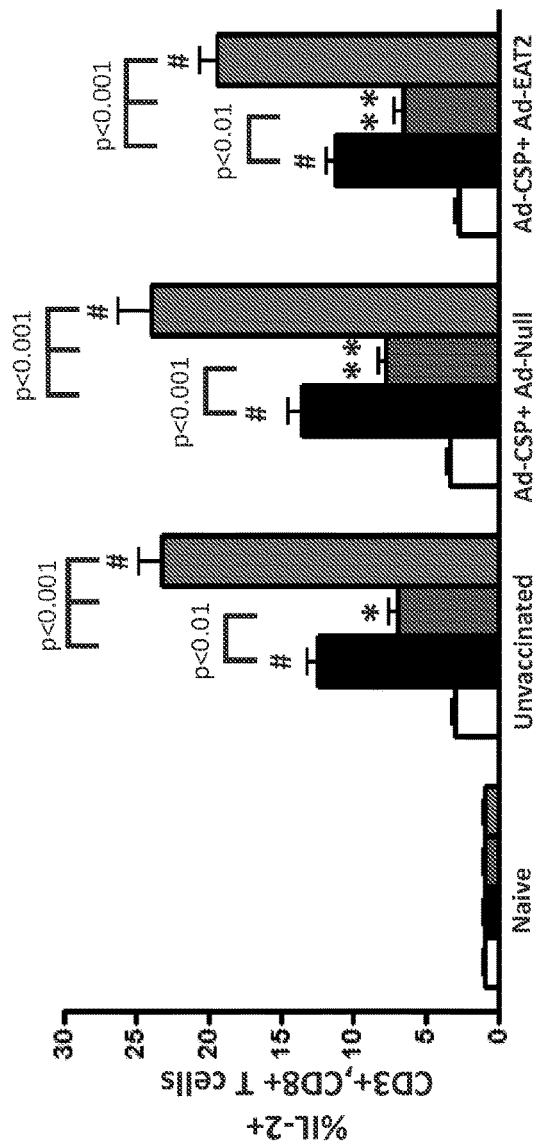
Fig. 18

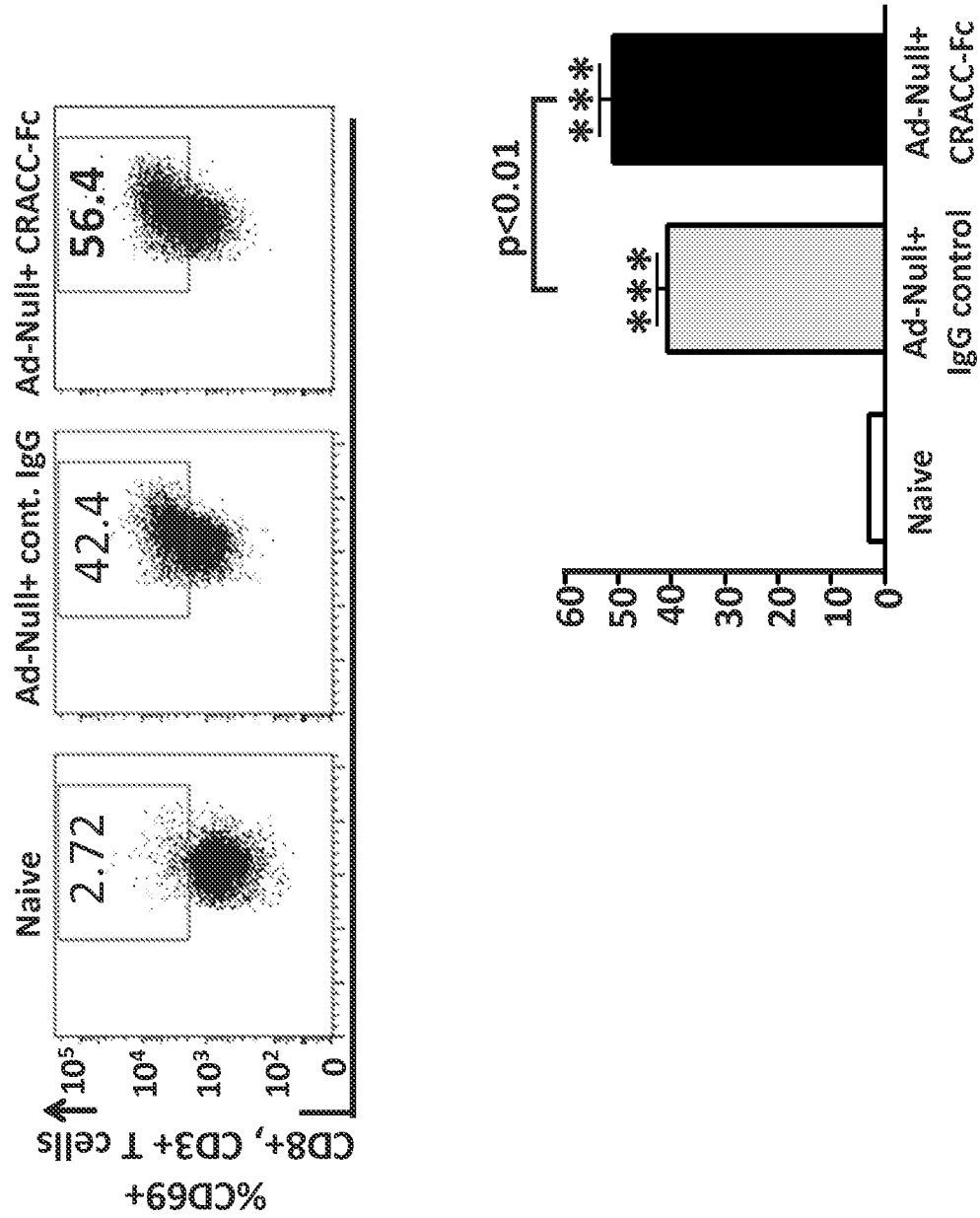

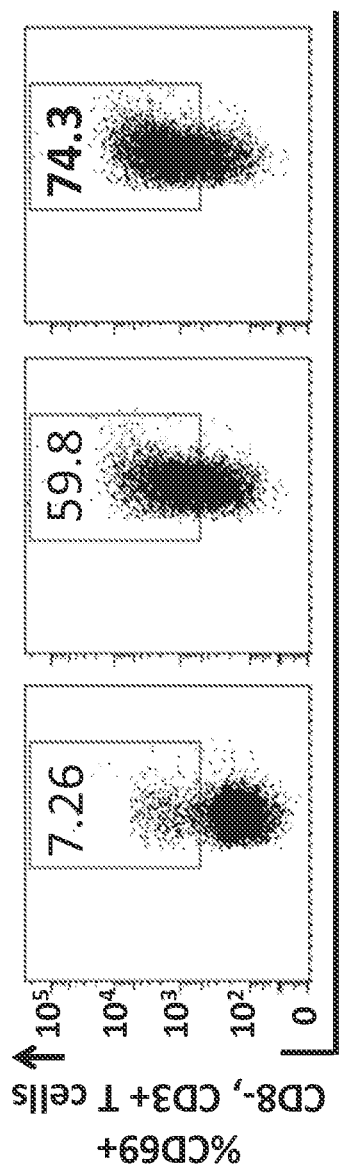
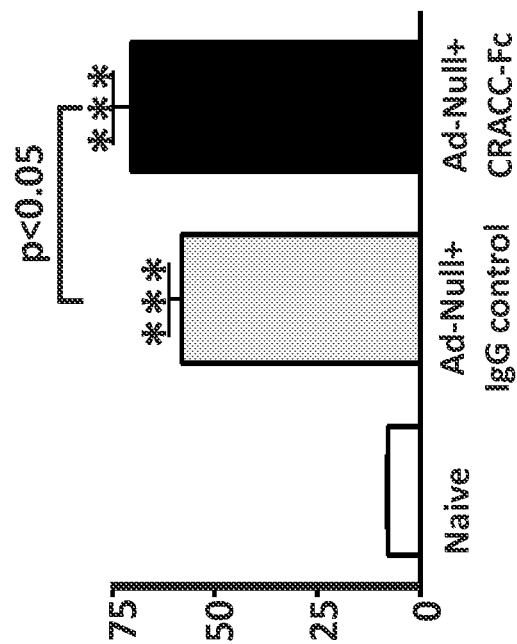
Fig. 21B

COMPOSITIONS COMPRISING FUSION PROTEINS USEFUL FOR MODULATING AN IMMUNE RESPONSE

RELATED APPLICATIONS

This application is a 371 National Stage Application of PCT/US15/051442, filed Sep. 22, 2015, which claims priority to U.S. Provisional Patent Application No. 62/054,133 filed Sep. 23, 2014, which is herein incorporated by reference in their entirety.

SEQUENCE LISTING

The instant application contains a Sequence Listing which has been submitted electronically in ASCII format and is hereby incorporated by reference in its entirety. Said ASCII copy, created on Dec. 1, 2015, is named MSS-007.25 (31742.00725)_SL.txt and is 65,562 bytes in size.

BACKGROUND

Several strategies have been utilized to improve the efficacy of vaccines targeting cancers and infectious diseases (Barouch and Deeks (2014) *Science* 345:169-174; Coffman et al., supra; and Koff et al. (2013) *Science* 340(6136): 1232910). Blockade of inhibitory pathways to boost immune responses, such as via the inhibition of the co-stimulatory molecules PD-1 and PD-L1, has been studied for the treatment of human cancer and chronic infectious diseases (Ha et al. (2008) *J Exp Med* 205:543-555; and Pardoll et al. (2012) *Nat Rev Cancer* 12:252-264. For example, several studies in murine models, non-human primates, and human clinical trials have shown that preventing interaction of PD-1 receptor and its ligand, PD-L1 and PD-L2, with a blocking antibody (either alone or in combination with other blocking antibodies toward other T cell co-inhibitory molecules) resulted in improved T cell function and reduction in viral loads (Brahmer et al. (2010) *J Clin Oncol* 28:3167-3175; Porichis et al. (2011) *Blood* 118:965-974; and Zhang et al. (2007) *Blood* 109:4671-4678). Therefore, manipulation of costimulotory pathways offers great potential to modulate immune responses in humans.

SUMMARY

The disclosure is based, at least in part, on the discovery that inhibiting the homophilic interaction between a CRACC protein expressed on the surface of T cell and a CRACC protein expressed on the surface of an antigen presenting cell (APC) can enhance activation of the T cell by a given antigen of interest. Inhibition of the CRACC-CRACC interaction enhances both antigen-specific T cells responses (e.g., the magnitude and breadth of the immune response to antigens) as well as innate immune responses. Among other things, these discoveries indicate that inhibiting CRACC-CRACC interactions in the context of antigen delivery (vaccination) can serve to enhance the efficacy of vaccines.

Accordingly, in one aspect, the disclosure features an agent that inhibits the homophilic interaction between two CRACC proteins for use in modulating (e.g., enhancing) activation of an immune cell, or for use in modulating (e.g., enhancing) an immune response, to an antigen of interest. Also featured are pharmaceutical compositions comprising such an agent and a pharmaceutically acceptable carrier or excipient. The agent and composition can also be for use in conjunction with an antigen (e.g., a vaccine). Suitable agents and antigens are elaborated on herein. In some embodiments, the agent is an antibody or antigen-binding fragment thereof that binds to a CRACC polypeptide (e.g., a human CRACC polypeptide, e.g., human CRACC extracellular domain (ECD)) and inhibits the interaction between two CRACC polypeptides. In some embodiments, the agent is a fusion protein comprising a CRACC ECD polypeptide (e.g., a human CRACC ECD) or a biologically-active fragment thereof that inhibits the interaction between two CRACC polypeptides. In some embodiments, the agent is monovalent. For example, the agent can be a monovalent antigen-binding fragment of an antibody (e.g., an scFv or Fab fragment), a single domain antibody, or a non-antibody scaffold protein.

In other aspect, the disclosure features compositions, e.g., pharmaceutical compositions, comprising an antigen (e.g., an effective amount or dose of an antigen) and an agent that inhibits the homophilic interaction between two CRACC proteins (e.g., an effective amount or dose of the agent). The compositions can be for use in enhancing an immune response to the antigen in a mammal or for enhancing activation of an immune cell to the antigen. In some embodiments, the agent is an antibody or antigen-binding fragment thereof that binds to a CRACC polypeptide (e.g., a human CRACC polypeptide, e.g., human CRACC extracellular domain (ECD)) and inhibits the interaction between two CRACC polypeptides. In some embodiments, the agent is a fusion protein comprising a CRACC ECD polypeptide (e.g., a human CRACC ECD) or a biologically-active fragment thereof that inhibits the interaction between two CRACC polypeptides. In some embodiments, the agent is monovalent. For example, the agent can be a monovalent antigen-binding fragment of an antibody (e.g., an scFv or Fab fragment), a single domain antibody, or a non-antibody scaffold protein.

In another aspect, the disclosure features a method for modulating activation of an immune cell. The method comprises, in the presence of an antigen, contacting the immune cell with an effective amount of an agent that inhibits the interaction between a first CRACC protein and a second CRACC protein, whereby activation of the immune cell is modulated. In yet another aspect, the disclosure features a method for enhancing activation of an immune cell. The method comprises, in the presence of an antigen, contacting the immune cell with an effective amount of an agent that inhibits the interaction between a first CRACC protein and a second CRACC protein, whereby activation of the immune cell is enhanced.

In another aspect, the disclosure features a method for modulating activation of an immune cell. The method comprises, in the presence of an antigen, contacting a plurality of immune cells (e.g., comprising a T cell and an antigen presenting cell) with an effective amount of an agent that inhibits the interaction between a first CRACC protein and a second CRACC protein, whereby activation of one or more immune cells in the plurality is modulated. In yet another aspect, the disclosure features a method for enhancing activation of an immune cell. The method comprises, in the presence of an antigen, contacting a plurality of immune cells (e.g., comprising a T cell and an antigen presenting cell) with an effective amount of an agent that inhibits the interaction between a first CRACC protein and a second CRACC protein, whereby activation of one or more immune cells in the plurality is enhanced. The plurality can be, e.g., splenocytes or peripheral blood mononuclear cells obtained from a mammal, e.g., a human. The mammal (e.g., human) can be one who has a cancer or an infection with a pathogenic microorganism. For example, the mammal can be a human patient infected with HIV-1.

In some embodiments, activation is modulated or enhanced by at least 10 (e.g., at least 15, 20, 25, 30, 35, 40, 45, 50, 55, 60, 65, 70, 75, 80, 85, 90, 95, 100, or more than 100) %, as compared to the activation of the immune cell by the antigen in the absence of the agent. In some embodiments, activation is modulated or enhanced by at least 1.5 (e.g., at least 2, 3, 4, 5, 10, 15, 20, 25, 30, 40, 50, 100, 500, or 1000) times the level of activation of the immune cell by the antigen in the absence of the agent. The method can also include contacting the immune cell with the antigen.

In some embodiments of any of the methods described herein, the immune cell is a T cell (e.g., a naïve T cell, a $CD3^+$ T cell, a $CD8^+$ T cell, or a $CD3^+CD8^+$ T cell). In some embodiments of any of the methods described herein, the immune cell is a natural killer cell (NK cell). In some embodiments of any of the methods described herein, the immune cell is a dendritic cell.

In some embodiments of any of the methods described herein, the contacting of the immune cell with the agent occurs in vitro. In some embodiments of any of the methods described herein, the contacting of the immune cell with the agent occurs in vivo.

In some embodiments of any of the methods described herein, the contacting of the immune cell with the agent occurs in the presence of more than one (e.g., two, three, four, five, six, seven, eight, nine, 10, 11, 12, 13, 14, 15, 16, 17, 18, 19, or 20) antigens. In some embodiments of any of the methods described herein, the contacting of the immune cell with the agent occurs in the presence of an antigen presenting cell (APC, e.g., a dendritic cell or a macrophage), for example, where the immune cell is a T cell.

In some embodiments of any of the methods described herein, the methods can include, following the contacting, determining the level of activation of the immune cell. The determining can comprise, e.g., detecting expression of a cytokine or chemokine by the immune cell. The cytokine can be, e.g., IL-2, IFNγ, or TNFα. In some embodiments, more than one cytokine is detected.

In some embodiments, any of the methods described herein can further comprise contacting the immune cell with an agent that: (i) binds to PD-1, PD-L1, or PD-L2 and (ii) inhibits the interaction between PD-1 and one of its natural ligands (e.g., PD-L1). Such an agent can be, e.g., an antibody or an antigen-binding fragment thereof that binds to PD-1, PD-L1, or PD-L2.

In yet another aspect, the disclosure features a method for modulating an immune response to an antigen by a mammal, the method comprising administering to a mammal an effective amount of an antigen and an effective amount of an agent that inhibits the interaction between a first CRACC protein and a second CRACC protein, wherein the immune response to the antigen by the mammal is modulated in the presence of the agent. In another aspect, the disclosure features a method for enhancing an immune response to an antigen by a mammal, the method comprising administering to a mammal an effective amount of an antigen and an effective amount of an agent that inhibits the interaction between a first CRACC protein and a second CRACC protein, wherein the immune response to the antigen by the mammal is enhanced in the presence of the agent.

In another aspect, the disclosure features a method for enhancing an immune response to an antigen by a mammal, the method comprising administering to a mammal an effective amount of an agent that inhibits the interaction between a first CRACC protein and a second CRACC protein, wherein the mammal has been exposed, or will be exposed, to an antigen, and wherein the immune response to the antigen by the mammal is enhanced in the presence of the agent. In some embodiments, the mammal was exposed to the antigen less than 30 (e.g., less than 29, 28, 27, 26, 25, 24, 23, 22, 21, 20, 19, 18, 17, 16, 15, 14, 13, 12, 11, 10, 9, 8, 7, 6, 5, 4, 3, 2, or 1) day(s) prior to the administering of the agent. In some embodiments, the mammal was exposed to the antigen less than 48 (e.g., 40, 36, 30, 24, 20, 18, 12, 6, 4, 3, 2, or 1) hour(s) prior to the administering of the agent. In some embodiments, the mammal will be exposed to the antigen within 30 (e.g., within 29, 28, 27, 26, 25, 24, 23, 22, 21, 20, 19, 18, 17, 16, 15, 14, 13, 12, 11, 10, 9, 8, 7, 6, 5, 4, 3, 2 or 1) day(s) after the administering of the agent. In some embodiments, the mammal will be exposed to the antigen (e.g., the antigen will be administered to the mammal by the same medical professional or a different medical professional) within 48 (e.g., 36, 30, 24, 20, 18, 12, 6, 5, 4, 3, 2, or 1) hour(s) after the administering of the agent.

In some embodiments, the immune response to the antigen is modulated or enhanced by at least 10 (e.g., at least 15, 20, 25, 30, 35, 40, 45, 50, 55, 60, 65, 70, 75, 80, 85, 90, 95, 100, or more than 100) %, as compared to the immune response to the antigen in the absence of the agent. In some embodiments, the immune response is modulated or enhanced by at least 1.5 (e.g., at least 2, 3, 4, 5, 10, 15, 20, 25, 30, 40, 50, 100, 500, or 1000) times the level of the immune response to the antigen in the absence of the agent.

In some embodiments, any of the methods herein can include administering to the mammal more than one (e.g., two, three, four, five, six, seven, eight, nine, 10, 11, 12, 13, 14, 15, 16, 17, 18, 19, or 20 or more) antigen(s). In some embodiments of any of the methods herein, the mammal has been exposed, or will be exposed, to more than one (e.g., two, three, four, five, six, seven, eight, nine, 10, 11, 12, 13, 14, 15, 16, 17, 18, 19, or 20 or more) antigen(s).

In some embodiments, the immune response is an innate response. In some embodiments, the immune response is a T cell memory response. In some embodiments, the immune response is a humoral immune response.

In some embodiments of any of the methods described herein, the agent is administered to the mammal prior to the antigen. In some embodiments of any of the methods described herein, the agent is administered to the mammal after the antigen. In some embodiments of any of the methods described herein, the agent is administered to the mammal concurrently with the antigen. In some embodiments of any of the methods described herein, the agent and antigen are administered to the mammal by the same route of administration. In some embodiments, the agent and antigen are administered to the mammal by different routes of administration. In some embodiments, the antigen is administered to the mammal by way of intramuscular injection.

In some embodiments of any of the methods described herein: (i) the antigen is administered more than one time to the mammal; (ii) the agent is administered more than one time to the mammal; and/or (iii) the agent and the antigen are each administered more than one time to the mammal.

Any of the methods described herein can further include administering to the mammal an effective amount of a compound that: (i) binds to PD-1, PD-L1, or PD-L2 and (ii) inhibits the interaction between PD-1 and one of its natural ligands (e.g., PD-L1). The compound can be, e.g., an antibody or antigen-binding fragment thereof that binds to PD-1, PD-L1, or PD-L2.

In some embodiments, any of the methods described herein can include the step of administering to the mammal an effective amount of a multispecific antibody (e.g., a bispecific antibody) that: (1) binds to a CRACC polypeptide and inhibits CRACC-CRACC homophilic interactions; and (2) binds to PD-1, PD-L1, or PD-L2 and inhibits the interaction between PD-1 and one of its natural ligands (e.g., PD-L1 or PD-L2).

In some embodiments of any of the methods described herein, the mammal is a human.

In some embodiments of any of the methods described herein, the mammal was exposed to the antigen at least once (e.g., at least twice, three times, four times, or even five times) prior to administration of the agent and/or the antigen. In some embodiments, the mammal was exposed to an effective amount of an antigen at least once (e.g., at least twice, three times, four times, or even five times) prior to administration of the agent and/or the antigen. In some embodiments, the mammal developed a measurable immune response to the antigen at least once (e.g., at least twice, three times, four times, or even five times) prior to administration of the agent and/or the antigen.

In some embodiments of any of the methods described herein, the mammal has an infection or a cancer. The infection can be, e.g., a viral infection, a bacterial infection, a fungal infection, or a parasitic infection. For example, the mammal can be infected with a retrovirus, picornavirus, a herpes virus, or a papillomavirus. The virus can be a human immunodeficiency virus (HIV), e.g., HIV-1.

In some embodiments of any of the methods described herein, the agent is a small molecule, a macrocycle compound, a polypeptide, a nucleic acid, a nucleic acid analog. In some embodiments of any of the methods described herein, the agent inhibits: (i) the expression of an mRNA encoding a CRACC protein or (ii) the stability of the mRNA. For example, the agent can be, e.g., a small interfering RNA (siRNA).

In some embodiments of any of the methods described herein, the agent binds to a CRACC protein (e.g., a human CRACC protein, a non-human primate CRACC protein, or a rodent CRACC protein). For example, the agent can be an antibody or an antigen-binding fragment thereof. In some embodiments, the agent (e.g., the antibody or antigen-binding fragment thereof) is cross-reactive with a human CRACC protein and a CRACC protein from a non-human primate (e.g., Rhesus or Cynomolgus macaque). The antigen-binding fragment can be any of those described herein. In some embodiments, the antibody or antigen-binding fragment thereof comprises an immunoglobulin Fc region that exhibits reduced ADCC activity, reduced CDC activity, or reduced ADCC and CDC activity, as compared to an Fc region from an IgG1 immunoglobulin molecule.

In some embodiments of any of the methods described herein, the agent comprises a soluble form of a CRACC protein. In some embodiments, the agent comprises the extracellular domain (ECD) of a CRACC protein or a fragment of the ECD, wherein the fragment inhibits the interaction between a first CRACC protein and a second CRACC protein. In some embodiments, the agent comprising a CRACC ECD polypeptide comprising the amino acid sequence depicted in SEQ ID NO:2.

In some embodiments, the agent comprises a human CRACC ECD polypeptide. In some embodiments, the agent comprises a CRACC ECD polypeptide from a non-human primate. In some embodiments, the agent comprises a CRACC ECD polypeptide from a rodent species (e.g., mouse or rat).

In some embodiments, the agent comprises a variant CRACC ECD polypeptide comprising an amino sequence that is at least 90 (e.g., at least 91, 92, 93, 94, 95, 96, 97, 98, or 99) % identical to the amino acid sequence depicted in SEQ ID NO:2.

In some embodiments, the agent comprises a variant CRACC ECD polypeptide comprising an amino acid sequence that has one or more amino acid substitutions, insertions, or deletions, relative to the amino acid sequence depicted in SEQ ID NO:2. In some embodiments, the variant CRACC ECD polypeptide has at least two (e.g., at least three, four, five, six, seven, eight, nine, 10, 11, 12, 13, 14, 15, 16, 17, 18, 19, 20, 21, 22, 23, 24, 25, 30, 35, 40, 45, or 50) amino acid substitutions, insertions, or deletions relative to the amino acid sequence depicted in SEQ ID NO:2. In some embodiments, the variant CRACC ECD polypeptide has no more than 60 (e.g., no more than 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, insertions or deletions, relative to the amino acid sequence depicted in SEQ ID NO:2.

In some embodiments, the variant CRACC polypeptide retains at least 10 (e.g., at least 15, 20, 25, 30, 35, 40, 45, 50, 55, 60, 65, 70, 75, 80, 85, 90, 95, 99, or 100) % of the ability of the full length, wild-type CRACC ECD from which the variant was derived to inhibit the CRACC-CRACC homophilic interaction.

In some embodiments of any of the methods described herein, the agent comprises a moiety that increases its serum half-life. In some embodiments, the moiety binds to neonatal Fc receptor (FcRn). In some embodiments, the moiety is an Fc region of an immunoglobulin molecule. In some embodiments, the moiety is a serum albumin protein or a fragment thereof. In some embodiments, the moiety comprises polyethylene glycol (PEG).

In some embodiments, the agent is a protein comprising the amino acid sequence depicted in SEQ ID NO:9. In some embodiments, the agent is a protein comprising the amino acid sequence depicted in SEQ ID NO:2. In some embodiments, the agent is a protein comprising the amino acid sequence depicted in SEQ ID NO:170. In some embodiments, the agent is a protein comprising the amino acid sequence depicted in SEQ ID NO:171.

In some embodiments of any of the methods described herein, the antigen comprises a viral protein, a bacterial protein, a fungal protein, a parasite protein, or an antigenic fragment of any of the foregoing. The viral protein can be a viral coat protein, e.g., an HIV-1 gag protein or an HIV-1 gp120 protein. In some embodiments, the parasite protein is a protozoan protein, such as CSP. In some embodiments, the antigen is a cancer antigen.

The instant disclosure also provides the discovery that a higher percentage of T cells from patients infected with a virus express CRACC polypeptide, relative to T cells from non-infected individuals. While the disclosure is not bound by any particular theory or mechanism of action, it is believed that expression of CRACC by the T cells may suppress the capacity of the cells to mount or sustain an immune response against the virus. Inhibition of CRACC-CRACC homophilic interactions in such patients is thus expected to alleviate the suppression of the immune response to the virus, or enhance an immune response to the virus, in such patients. Therefore, in yet another aspect, the disclosure features a method for enhancing an immune response in a mammal afflicted with a cancer or an infection. The method comprises administering to the mammal an effective amount of an agent that inhibits the interaction between a first CRACC protein and a second CRACC protein to thereby enhance an immune response by the mammal against the cancer or infection. The methods can also include determining whether CRACC protein is expressed by immune cells (e.g., T cells, such as CD8$^+$ T cells) obtained from the mammal, relative to the expression of CRACC by immune cells of the same histological type from a healthy mammal of the same species. In some embodiments, the immune cell is a T cell.

In some embodiments, the mammal is afflicted with a viral infection. In some embodiments, the viral infection is HIV.

In yet another aspect, the disclosure features a multispecific antibody (e.g., a bispecific antibody) that: (1) binds to a CRACC polypeptide and inhibits CRACC-CRACC homophilic interactions; and (2) binds to PD-1, PD-L1, or PD-L2 and inhibits the interaction between PD-1 and one of its natural ligands (e.g., PD-L1 or PD-L2).

In some embodiments of any of the methods described above, the agent that inhibits the interaction between two CRACC polypeptides (e.g., and binds to a CRACC polypeptide) is monovalent. For example, the agent can be a monovalent antigen-binding fragment of an antibody (e.g., an scFv or Fab fragment), a single domain antibody, or a non-antibody scaffold protein. In some embodiments, the monovalent agent is a fusion protein comprising a CRACC ECD, wherein the agent is a monomer.

Also provided are methods for inhibiting an immune response or inhibiting activation of an immune cell by increasing or enhancing the interaction between two CRACC proteins. Thus, in another aspect, the disclosure features an agent that enhances the homophilic interaction between two CRACC proteins for use in inhibiting activation of an immune cell, or for use in inhibiting an immune response, to an antigen of interest. Also featured are pharmaceutical compositions comprising such an agent and a pharmaceutically acceptable carrier or excipient. In some embodiments, the agent is an antibody or antigen-binding fragment thereof that binds to a CRACC polypeptide (e.g., a human CRACC polypeptide, e.g., human CRACC extracellular domain (ECD)) and enhances the interaction between two CRACC polypeptides.

In another aspect, the disclosure features a method for inhibiting activation of an immune cell. The method comprises, in the presence of an antigen, contacting the immune cell with an effective amount of an agent that enhances the interaction between a first CRACC protein and a second CRACC protein, whereby activation of the immune cell is inhibited. In yet another aspect, the disclosure features a method for inhibiting activation of an immune cell. The method comprises, in the presence of an antigen, contacting the immune cell with an effective amount of an agent that enhances the interaction between a first CRACC protein and a second CRACC protein, whereby activation of the immune cell is inhibited.

In another aspect, the disclosure features a method for inhibiting activation of an immune cell. The method comprises, in the presence of an antigen, contacting a plurality of immune cells (e.g., comprising a T cell and an antigen presenting cell) with an effective amount of an agent that enhances the interaction between a first CRACC protein and a second CRACC protein, whereby activation of one or more immune cells in the plurality is inhibited. In yet another aspect, the disclosure features a method for inhibiting activation of an immune cell. The method comprises, in the presence of an antigen, contacting a plurality of immune cells (e.g., comprising a T cell and an antigen presenting cell) with an effective amount of an agent that enhances the interaction between a first CRACC protein and a second CRACC protein, whereby activation of one or more immune cells in the plurality is inhibited. The plurality can be, e.g., splenocytes or peripheral blood mononuclear cells obtained from a mammal, e.g., a human. The mammal (e.g., human) can be one who has an autoimmune or inflammatory disease. For example, the mammal can be a human patient with: rheumatoid arthritis; juvenile chronic arthritis; a spondyloarthropathy, such as ankylosing spondylitis, psoriatic arthritis, or arthritis associated with inflammatory bowel disease; vasculitis, such as polyarteritis nodosa, Wegener's granulomatosis, giant cell arteritis, Henoch-Schoenlein purpura, and microscopic vasculitis of the kidneys; Sjogren's syndrome; systemic lupus erythematosus; inflammatory bowel disease, including Crohn's disease and ulcerative colitis; chronic active hepatitis; primary biliary cirrhosis; cryptogenic fibrosing alveolitis and other fibrotic lung diseases; uveitis; multiple sclerosis; myasthenia gravis; hemolytic anemia; scleroderma; graft versus host disease; allergy; and transplantation of kidneys, liver, heart, lungs, bone marrow, skin, or of other organs.

In yet another aspect, the disclosure features a method for inhibiting an immune response to an antigen by a mammal, the method comprising administering to a mammal in need thereof an effective amount of an agent that enhances the interaction between a first CRACC protein and a second CRACC protein, wherein the immune response to an antigen by the mammal is inhibited in the presence of the agent. The mammal (e.g., human) can be one who has an autoimmune or inflammatory disease, such as any of such conditions known in the art or described herein. In some embodiments, the method is to be performed in conjunction with a transplant procedure, e.g., administering the agent to a transplant recipient before or following the transplant of an organ or tissue. The method can further include, optionally, administering one or more anti-inflammatory drugs (e.g., steroids, non-steroidal anti-inflammatory drugs (NSAIDs), an anti-TNFα compound (e.g., adalimumab, infliximab, or entanercept)). In some embodiments, the agent is an antibody or antigen-binding fragment thereof that binds to a CRACC polypeptide (e.g., a human CRACC polypeptide, e.g., human CRACC extracellular domain (ECD)) and enhances the interaction between two CRACC polypeptides.

In yet another aspect, the disclosure features a method for identifying a compound that modulates the activation of an immune cell. The method comprises: (i) in the presence of an antigen, contacting an immune cell with a test compound that binds to a CRACC protein and (ii) detecting activation of the immune cell in the presence of the test compound and antigen. A change in the level or duration of activation by the immune cell in the presence of the test compound, as compared to the level or duration of activation in the absence of the test compound, indicates that the test compound is a compound that modulates the activation of an immune cell by the antigen. In some embodiments, the test compound enhances activation of the immune cell. In some embodiments, the method further comprises contacting the immune cell with the antigen.

In some embodiments, the immune cell is a T cell, e.g., a naïve T cell or a CD8$^+$ T cell. In some embodiments, the immune cell is a dendritic cell (and the test compound modulates the maturation or differentiation of the dendritic cell). In some embodiments, the immune cell is a NK cell.

In some embodiments, the contacting occurs in the presence of more than one (e.g., at least two, three, four, five, six, seven, eight, nine, 10, 11, 12, 13, 14, 15, 16, 17, 18, 19, or 20 or more) antigen(s).

In some embodiments, the contacting occurs in the presence of an antigen presenting cell (APC). The APC can be a macrophage or a dendritic cell.

In some embodiments, the detecting comprises measuring the expression of a cytokine or chemokine by the immune cell. The cytokine can be, e.g., IL-2, IFNγ, or TNFα.

In another aspect, the disclosure features a therapeutic kit comprising: (a) an antigen and (b) an agent that inhibits the interaction between a first CRACC protein and a second CRACC protein. The agent can be any of those described herein. The antigen can be any of those described herein or known in the art. The kit can also include, optionally, a compound that: (i) binds to PD-1, PD-L1, PD-L2 and (ii) inhibits the interaction between PD-1 and one its natural ligands (e.g., PD-L1 or PD-L2), e.g., an anti-PD-1 or anti-PD-L1 antibody or antigen-binding fragment thereof. In some embodiments, the kit comprises a multispecific (e.g., a bispecific) antibody that: (1) binds to a CRACC polypeptide and inhibits CRACC-CRACC homophilic interactions; and (2) binds to PD-1, PD-L1, or PD-L2 and inhibits the interaction between PD-1 and PD-L1.

In another aspect, the disclosure features a composition comprising: (a) an antigen and (b) an agent that inhibits the interaction between a first CRACC protein and a second CRACC protein. The agent can be any of those described herein. The antigen can be any of those described herein or known in the art.

In another aspect, the disclosure features a therapeutic kit comprising: (i) an agent that enhances (agonizes) the interaction between a first CRACC protein and a second CRACC protein, e.g., an anti-CRACC antibody. The therapeutic kit is useful for, among other things, treating a human afflicted with an inflammatory or autoimmune disorder. The kit can also include, optionally, one or more anti-inflammatory drugs.

"Polypeptide," "peptide," and "protein" are used interchangeably and mean any peptide-linked chain of amino acids, regardless of length or post-translational modification. As noted below, the polypeptides described herein can be, e.g., wild-type proteins, functional fragments of the wild-type proteins, or variants of the wild-type proteins or fragments. Variants, in accordance with the disclosure, can contain amino acid substitutions, deletions, or insertions. The substitutions can be conservative or non-conservative. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST software. Appropriate parameters for measuring alignment, including any algorithms needed to achieve maximal alignment over the full-length of the sequences being compared can be determined by known methods.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for modulating an immune response to an antigen in a mammal, will be apparent from the following description, the examples, and from the claims.

BRIEF DESCRIPTION OF THE SEQUENCES

SEQ ID NO:1 is an exemplary amino acid sequence for a full-length, human CRACC polypeptide.

SEQ ID NO:2 is an exemplary amino acid sequence for the extracellular domain (ECD) of human CRACC.

SEQ ID NO:3 is an exemplary amino acid sequence for a full-length CRACC polypeptide expressed by Rhesus macaque.

SEQ ID NO:4 is an exemplary amino acid sequence for a full-length CRACC polypeptide expressed by Chimpanzee.

SEQ ID NO:5 is an exemplary amino acid sequence for a full-length, murine CRACC polypeptide.

SEQ ID NO:6 is an exemplary amino acid sequence for the FLAG epitope tag.

SEQ ID NO:7 is an exemplary amino acid sequence for a polyhistidine epitope tag.

SEQ ID NO:8 is an exemplary amino acid sequence for a hemagglutinin epitope tag.

SEQ ID NO:9 is an exemplary amino acid sequence for the extracellular domain of murine CRACC.

SEQ ID NO:10 is an exemplary amino acid sequence for a full-length, human PD-1 polypeptide.

SEQ ID NO:11 is a peptide from HIV-1 Gag protein.

SEQ ID NO:12 is an exemplary amino acid sequence for murine EAT-2 protein.

SEQ ID NOs:13-40 (Table 1) correspond to exemplary primer nucleotide sequences.

SEQ ID NOs:41-169 (Table 2) correspond to exemplary HIV-1 Gag peptide amino acid sequences.

SEQ ID NO:170 is an exemplary amino acid sequence for a fusion protein comprising human CRACC ECD and a human IgG4 Fc constant region.

SEQ ID NO:171 is an exemplary amino acid sequence for a fusion protein comprising murine CRACC ECD and a murine IgG1 Fc constant region.

SEQ ID NO:172 is an exemplary amino acid sequence for an human IL-12 signal peptide.

BRIEF DESCRIPTION OF THE DRAWINGS

FIG. 1A depicts quantitative RT-PCR analysis for SLAM family of receptor gene expression at 6 hours post-infection. FIG. 1B depicts the results of a time course analysis for CRACC gene expression in RAW264.7 cells following rAd5-EAT2 or rAd5-Null infection. FIG. 1C depicts a gene expression analysis for immune response genes following rAd5-EAT2 or rAd5-Null infection. Data are representative of four independent experiments with similar results. Samples were plated in quadruplicate and are expressed as mean±SD. *, **, denotes $p<0.05$, $p<0.001$, statistically different from mock treated cells.

(FIG. 8A) IFNγ expressing NK cells, (FIG. 8B) CD80, (FIG. 8C) CD86, and (FIG. 8D) MHC-II$^+$ expression by CD11c+CD11b$^+$ dendritic cells. *** denotes p<0.001 statistically different from naive animals.

FIGS. 11A, 11B, and 11C are each a series of flow cytometry dot plots, and associated bar graphs summarizing the results set forth in the dot plots, depicting the differential activation of adaptive immune cells following CRACC-Fc vaccination. Male C57BL/6 mice (n=5) were mock injected or I.P. injected with a mixture of rAd5-Null (2×10$^{10}$ vps/mouse) and either CRACC-Fc fusion protein or control IgG antibodies (200 μg/mouse) (prepared in a 200 μl 1× sterile PBS). After 12 hours, mice were sacrificed and splenocytes were obtained. Multiparametric flow cytometry analysis for CD69 expression on CD8$^+$CD3$^+$ T cells (FIG. 11A), CD8$^-$CD3$^+$ T cells (FIG. 11B), and CD19$^+$CD3$^-$NK1.1$^-$ cells (FIG. 11C) was performed. *** denotes p<0.001, statistically different from naive animals.

FIG. 12A depicts a flow cytometry analysis for the percentages of CD8$^+$CD3$^+$ T cells (left histograms and center bar graph) and CD8$^-$CD3$^+$ T cells (right bar graph). FIG. 12B depicts the percentages of CD19$^+$CD3$^-$ B cells, 12 days following rAd5-Null and either CRACC-Fc or control IgG co-administration.

FIGS. 13A, 13B, and 13C are each a series of flow cytometry histograms, and associated bar graphs summarizing the results set forth in the dot plots, depicting the enhancement of antigen-specific memory CD8$^+$ T cell responses following CRACC-CRACC inhibition. Splenocytes were isolated from C57BL/6 mice 14 days after injection of the mice with rAd5-Gag. Ex vivo, the splenocytes were contacted with a Gag antigen in the presence of an antagonist anti-CRACC antibody or an IgG control antibody (which does not bind to CRACC). The total frequency of splenic CD8$^+$ T cells derived from naïve or vaccinated mice expressing IFNγ (FIG. 13A), TNFα (FIG. 13B), and IL-2 (FIG. 13C) is shown as indicated. Data are representative of two independent experiments with similar results. The percentage of cytokine expressing cells is indicated in each dot plot. FSC refers to forward scatter in the dot plots. *, , * denotes p<0.05, p<0.01, p<0.001 statistically different from mock injected animals.

FIG. 14 is a series of flow cytometry histograms, and an associated bar graph summarizing the results set forth in the dot plots, depicting the percentage of CD8$^+$ cells expressing CRACC polypeptide. The cells were PBMCs obtained from patients infected with HIV or non-infected patients ("normal"). The percentage of CRACC positive cells is indicated in each dot plot. , * denotes p<0.05, p<0.01, p<0.001 statistically different from normal donors.

FIG. 18 is a series of flow cytometry histograms, and an associated bar graph summarizing the results set forth in the dot plots, depicting the percentage of IL-2-expressing CD3$^+$ CD8$^+$ T cells following exposure to CSP peptide (CSP pep.) in the presence or absence of an anti-CRACC antibody. Splenocytes obtained from mice infected with malaria or non-infected mice were contacted ex vivo with a CSP peptide (CSP pep.) and with an anti-CRACC antibody, an anti-PD-1 antibody, or a control IgG antibody that does not bind to CRACC. The percentage of splenic CD3$^+$CD8$^+$ T cells expressing IL-2 is shown as indicated. ** denotes p<0.01 and # denotes p<0.001 statistically different from mock injected animals.

FIGS. 21A and 21B are each a series of flow cytometry dot plots, and associated bar graphs summarizing the results set forth in the dot plots, depicting the CD69 expression profiles of CD3$^+$CD8$^+$ T cells, or CD3$^+$CD8$^-$ T cells, from mice vaccinated with rAd5-Null and CRACC-Fc fusion protein or naïve mice. The percentage of splenic of CD3$^+$CD8$^+$ T cells (FIG. 23A) or CD3$^+$CD8$^-$ T cells (FIG. 29B) expressing CD69 is shown as indicated. *** denotes p<0.001, statistically different from naive animals.

FIG. 22A depicts the percentage of CD3$^-$CD19$^+$ positive B cells in splenocyte populations obtained from the different mouse cohorts. FIG. 22B depicts the percentage of CD69 expressing-CD3$^-$ CD19$^+$ B cells in splenocyte populations from each mouse cohort. *** denotes p<0.001, statistically different from naive animals.

DETAILED DESCRIPTION

Figure 1:
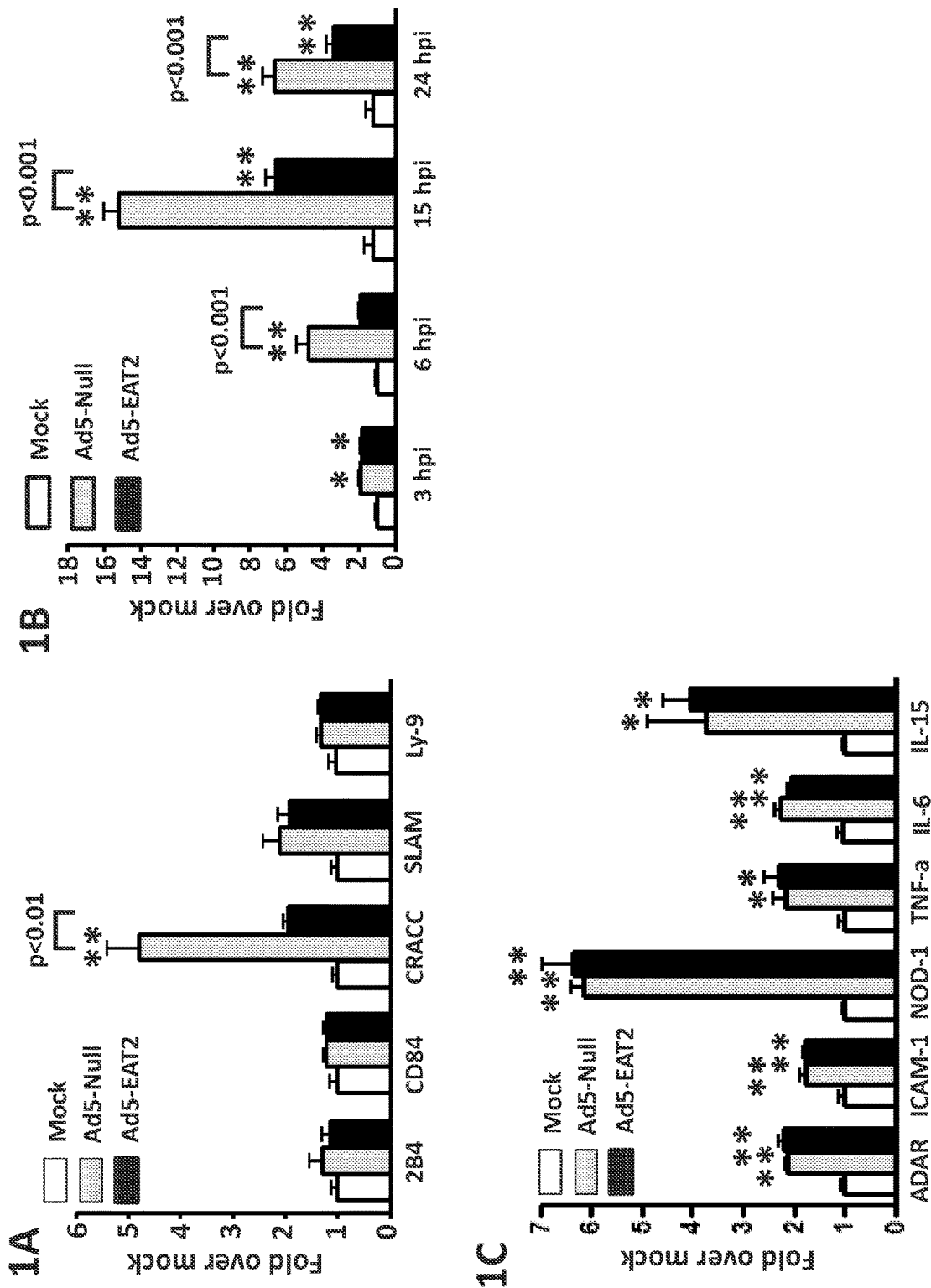
FIGS. 1A, 1B, and 1C are a set of bar graphs depicting the effects of EAT2 overexpression-mediated CRACC inhibition. RAW264.7 cells (300,000 cells/well) were mock-infected (white bars) or infected (at a multiplicity of infection of 20,000 virus particles/cell) with rAd5-Null (gray bars) or rAd5-EAT2 (black bars).

The present disclosure provides, among other things, agents (e.g., antagonist anti-CRACC antibodies or fusion proteins that comprise the CRACC ECD or fragments thereof) that inhibit the homophilic interaction between two CRACC proteins. Also provided are applications, such as therapeutic and diagnostic methods, in which the agents are useful. While in no way intended to be limiting, exemplary agents, compositions (e.g., pharmaceutical compositions and formulations), and methods for preparing and using these agents and compositions are elaborated on below.

Agents that Inhibit CRACC

The disclosure features agents that inhibit the interaction between two CRACC proteins (e.g., a first CRACC protein expressed on the surface of an antigen presenting cell and a second CRACC protein expressed on the surface of a T cell). Inhibition of the interaction between two CRACC proteins can be inhibition of: (i) the transcription of a CRACC coding sequence, (ii) the translation of a CRACC-encoding mRNA, (iii) the stability of a CRACC-encoding mRNA, (iv) the intracellular trafficking of a CRACC protein, (v) the stability of a CRACC protein, (vi) the homophilic interaction between two CRACC proteins, and/or (vii) the ability of a CRACC protein to bind to one or more cytosolic adapter proteins (e.g., EAT-2). In some embodiments, the agent binds to a CRACC polypeptide and inhibits the homophilic interaction between two CRACC polypeptides. The agent inhibitor can be, e.g., a small molecule, a nucleic acid or nucleic acid analog, a peptidomimetic, a polypeptide, a macrocycle compound, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA (siRNA), locked nucleic acid inhibitors, and peptide nucleic acid inhibitors. In some embodiments, an agent may be a protein or protein fragment.

As used herein, the term "inhibiting" and grammatical equivalents thereof refer to a decrease, limiting, and/or blocking of a particular action, function, or interaction. In one embodiment, the term refers to reducing the level of a given output or parameter to a quantity (e.g., the background level of homophilic interaction between CRACC proteins) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter.

As used herein, the term "interaction", when referring to an interaction between two molecules, refers to the physical contact (e.g., binding) of the molecules with one another. Generally, such an interaction results in an activity (which produces a biological effect) of one or both of said molecules. A homophilic interaction is the interaction between two like proteins (e.g., two CRACC proteins). To inhibit such an interaction results in the disruption of the activity of one or more molecules involved in the interaction.

"Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566). It is within the scope of this application that such a library may be used to screen for inhibitors of human CRACC proteins. There are numerous commercially available compound libraries, such as the Chembridge DIVERSet. Libraries are also available from academic investigators, such as the Diversity set from the NCI developmental therapeutics program. Rational drug design may also be employed.

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of humans or animals. It should be noted that peptidomimetics may or may not have similar two-dimensional chemical structures, but share common three-dimensional structural features and geometry. Each peptidomimetic may further have one or more unique additional binding elements.

Nucleic acid inhibitors can be used to decrease expression of an endogenous gene encoding a CRACC polypeptide (e.g., a human CRACC polypeptide). The nucleic acid antagonist can be, e.g., an siRNA, a dsRNA, a ribozyme, a triple-helix former, an aptamer, or an antisense nucleic acid. siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. The siRNA sequences can be, in some embodiments, exactly complementary to the target mRNA. dsRNAs and siRNAs in particular can be used to silence gene expression in mammalian cells (e.g., human cells). See, e.g., Clemens et al. (2000) *Proc Natl Acad Sci USA* 97:6499-6503; Billy et al. (2001) *Proc Natl Acad Sci USA* 98:14428-14433; Elbashir et al. (2001) *Nature* 411:494-8; Yang et al. (2002) *Proc Natl Acad Sci USA* 99:9942-9947, and U.S. Patent Application Publication Nos. 20030166282, 20030143204, 20040038278, and 20030224432. Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding a. human CRACC protein) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by aritisense oligonucleotide hybridization to the RNA. Exemplary antisense compounds include DNA or RNA sequences that specifically hybridize to the target nucleic acid, e.g., the mRNA encoding a CRACC polypeptide (e.g., a human CRACC polypeptide). The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as $C_5$-propynylcytosine and $C_5$-propynyluracil. Other suitable modified nucleobases include, e.g., 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. See, e.g., U.S. Pat. Nos. 4,987,071; 5,116,742; and U.S. Pat. No. 5,093,246; "Antisense RNA and DNA," D. A. Melton, Ed., Cold Spring Harbor Laboratory, Cold Spring Harbor, N.Y. (1988); Haselhoff and Gerlach (1988) *Nature* 334:585-59; Helene, C. (1991) *Anticancer Drug D* 6:569-84; Helene (1992) *Ann NY Acad Sci* 660:27-36; and Maher 11992) *Bioassays* 14:807-15.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacal* 173:305-326).

Agents Comprising a CRACC Polypeptide or Fragment Thereof

In some embodiments, the agent comprises, or consists of, all or a portion of a CRACC polypeptide (e.g., the extracellular domain of a CRACC polypeptide), wherein the portion retains the ability to inhibit the interaction between two CRACC polypeptides. The following is an exemplary amino acid sequence for a full-length human CRACC protein:

(UniProt identifier: Q9NQ25)

(SEQ ID NO: 1)

MAGSPTCLTLIYILWQLTGSAASGPVKELVGSVGGAVTFPLKSKVKQ

VDSIVWTFNTTPLVTIQPEGGTIIVTQNRNRERVDFPDGGYSLKLSK

LKKNDSGIYYVGIYSSSLQQPSTQEYVLHVYEHLSKPKVTMGLQSNK

NGTCVTNLTCCMEHGEEDVIYTWKALGQAANESHNGSILPISWRWGE

SDMTFICVARNPVSRNFSSPILARKLCEGAADDPDSSM*VLLCLLLVP*

*LLLSLFVLGLFLWF*LKRERQEEYIEEKKRVDICRETPNICPHSGENT

EYDTIPHTNRTILKEDPANTVYSTVEIPKKMENPHSLLTMPDTPRLF

AYENVI.

The signal sequence of the protein consists of the first 22 amino acids and is underlined. The extracellular domain (ECD) of the human CRACC protein (amino acids 23-226) is in bold. The protein also includes a transmembrane domain, amino acids 227-247, the amino acid sequence of which is in italics. The remaining amino acids (248-335) constitute the cytoplasmic domain of this exemplary CRACC protein sequence. An exemplary amino acid for the human CRACC ECD is as follows:

(SEQ ID NO: 2)
SGPVKELVGSVGGAVTFPLKSKVKQVDSIVWTFNTTPLVTIQPEGGT

IIVTQNRNRERVDFPDGGYSLKLSKLKKNDSGIYYVGIYSSSLQQPS

TQEYVLHVYEHLSKPKVTMGLQSNKNGTCVTNLTCCMEHGEEDVIYT

WKALGQAANESHNGSILPISWRWGESDMTFICVARNPVSRNFSSPIL

ARKLCEGAADDPDSSMAANESHNGSILPISWRWGESDMTFICVARNP

VSRNFSSPILARKLCEGAADDPDSSM.

The following is an exemplary amino acid sequence for a full-length CRACC protein from Rhesus macaque:

(UniProt identifier: F7HQ72)
(SEQ ID NO: 3)
MAGSPTCFTFIYILWQLTGSTASGSVKELVGSIGGAVTFPLKSEVKQ

VDSIVWTFNTTTLVTIQPEGGPMIVTQNRNKERVHFPDGGYSLKLSK

LKKNDSGIYNVEIYSSSLQDPFTRKYVLRVYEHLSKPKVTMGLQSNK

NGTCVTNLTCHMEHGEEDVIYTWKALGQAVNESHNGSILPISWRWGE

SDMTFICTVRNPVSSNSSSPILARKLCEGAADDSDSSM*VLLCLLLVP*

*LLLSLFVLGLFLWF*LKRETQEESIEEKKRADICRETPNICPYSGENT

EYDTIPYTNRTIPMEDAANTLYSTVEIPKKIENPHSLLTMPDTPRLF

AYENVI.

The signal sequence of the protein is underlined. The extracellular domain (ECD) of the rhesus CRACC protein (amino acids 23-226) is in bold. The protein also includes a transmembrane domain, amino acids 227-247, the amino acid sequence of which is in italics. The remaining amino acids constitute the cytoplasmic domain of this exemplary CRACC protein sequence.

The following is an exemplary amino acid sequence for a full-length CRACC protein from chimpanzee:

(UniProt identifier: H2Q0F0)
(SEQ ID NO: 4)
MAGSPTCLTLIYILWQLTGSAASGPVRELVGSVGGAVTFPLKSKVKQ

VDSIVWTFNTTPLVTIQPEGGTIIVTQNRNKERVDFPDGGYSLKLSK

LKKNDSGIYYVGIYSSSLQQPSTQKYVLHVYEHLSKPKVTMGLQSNK

NGTCVTNLTCCMEHGEEDVIYTWKALGQAANESHNGSILPISWRWGE

SDMTFICVARNPVSSNFSSPILARKLCEGAADDPDSSM*VLLCLLLVP*

*LLLSLFVLGLFLWF*LKRERQEESIEEKKRADICRETPNICPHSGENT

EYDTIPHTNRTILKEDPANTVYSTVEIPKKMENPHSLLTMPDTPRLF

AYENVI.

The signal sequence of the protein is underlined. The extracellular domain (ECD) of the chimpanzee CRACC protein (amino acids 23-226) is in bold. The protein also includes a transmembrane domain, amino acids 227-247, the amino acid sequence of which is in italics. The remaining amino acids constitute the cytoplasmic domain of this exemplary CRACC protein sequence.

The following is an exemplary amino acid sequence for a full-length, murine CRACC protein:

(UniProt identifier: Q8BHK6)
(SEQ ID NO: 5)
MARFSTYIIFTSVLCQLTVTAASGTLKKVAGALDGSVTFTLNITEIK

VDYVVWTFNTFFLAMVKKDGVTSQSSNKERIVFPDGLYSMKLSQLKK

NDSGAYRAEIYSTSSQASLIQEYVLHVYKHLSRPKVTIDRQSNKNGT

CVINLTCSTDQDGENVTYSWKAVGQGDNQFHDGATLSIAWRSGEKDQ

ALTCMARNPVSNSFSTPVFPQKLCEDAATDLTSLRG*ILYILCFSAVL*

*ILFAVLLTIF*HTTWIKKGKGCEEDKKRVDRHQEMPDLCPHLEENADY

DTIPYTEKRRPEEDAPNTFYSTVQIPKVVKSPSSLPAKPLVPRSLSF

ENVI.

The signal sequence of the protein is underlined. The extracellular domain (ECD) of the murine CRACC protein (amino acids 23-224) is in bold. The protein also includes a transmembrane domain, amino acids 225-245, which are in italics. The remaining amino acids constitute the cytoplasmic domain of this exemplary murine CRACC protein sequence. An exemplary amino acid sequence for a murine CRACC ECD is as follows:

(SEQ ID NO: 9)
SGTLKKVAGALDGSVTFTLNITEIKVDYVVWTFNTFFLAMVKKDGVT

SQSSNKERIVFPDGLYSMKLSQLKKNDSGAYRAEIYSTSSQASLIQE

YVLHVYKHLSRPKVTIDRQSNKNGTCVINLTCSTDQDGENVTYSWKA

VGQGDNQFHDGATLSIAWRSGEKDQALTCMARNPVSNSFSTPVFPQK

LCEDAATDLTSLEG.

In some embodiments, the agent comprises a variant CRACC ECD polypeptide comprising an amino sequence that is at least 90 (e.g., at least 91, 92, 93, 94, 95, 96, 97, 98, or 99) % identical to the amino acid sequence depicted in SEQ ID NO:2.

In some embodiments, the agent comprises a variant CRACC ECD polypeptide comprising an amino acid sequence that has one or more amino acid substitutions, insertions, or deletions, relative to the amino acid sequence depicted in SEQ ID NO:2. In some embodiments, the variant CRACC ECD polypeptide has at least two (e.g., at least three, four, five, six, seven, eight, nine, 10, 11, 12, 13, 14, 15, 16, 17, 18, 19, 20, 21, 22, 23, 24, 25, 30, 35, 40, 45, or 50) amino acid substitutions, insertions, or deletions relative to the amino acid sequence depicted in SEQ ID NO:2. In some embodiments, the variant CRACC ECD polypeptide has no more than 60 (e.g., no more than 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, insertions or deletions, relative to the amino acid sequence depicted in SEQ ID NO:2. The substitutions can be conservative, non-conservative, or a mixture of both.

In some embodiments, an inhibitory portion of a CRACC polypeptide retains at least 10 (e.g., at least 15, 20, 25, 30, 35, 40, 45, 50, 55, 60, 65, 70, 75, 80, 85, 90, 95, or 100) % of the ability of the full-length, wild-type CRACC ECD from the same species from which the portion was derived to inhibit an interaction between two CRACC polypeptides. Methods for measuring the interaction between two polypeptides, as well as inhibition of that interaction, are well known in the art. For example, a first CRACC protein can be bound to a solid surface (the surface of a well in an assay plate or a chip) and then contacted with a detectably-labeled second CRACC protein in the presence or absence of an agent. The surface is then, optionally, washed to remove unbound material. Detection of the signal produced by the detectably-labeled second CRACC protein bound to the first CRACC protein follows. Decreased binding of the second CRACC protein (as a function of a reduction in signal from the detectable label) in the presence of the agent as compared to binding of the second CRACC protein in the absence of the agent indicates the agent inhibits the interaction between the CRACC proteins. Suitable methods for detecting or measuring the interaction between two CRACC proteins are described herein.

In some embodiments, the agents described herein can be modified. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the agents can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO:6)), polyhistidine (6-His; HHHHHH (SEQ ID NO:7), hemagglutinin (HA; YPYDVP-DYA (SEQ ID NO:8)), glutathione-S-transferase (GST), or maltose-binding protein (MBP)) for use in purifying a polypeptide. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-ALEXA FLUOR® 700, CyS, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an agent containing a portion of a CRACC polypeptide and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of a protein agent. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) J Nucl Med 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the agents can be modified, e.g., with a moiety that improves the stabilization and/or retention of the antibodies in circulation, e.g., in blood, serum, or other tissues. For example, an agent comprising the ECD of a CRACC polypeptide can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the agent by at least 1.5 (e.g., at least 2, 5, 10, 15, 20, 25, 30, 40, or 50 or more) fold.

Fusion Proteins

In some embodiments, the agents described herein are fusion proteins comprising all or part of a CRACC ECD (see above) and a heterologous moiety. The heterologous moiety can be, or include, for example, the Fc portion of an immunoglobulin, i.e., the carboxyl-terminal portion of an immunoglobulin heavy chain constant region, or an analog or portion thereof capable of binding an Fe receptor. Each immunoglobulin heavy chain constant region comprises four or five domains. The domains are named sequentially as follows: CM-hinge-CH2-CH3, and optionally, CH4. CH4 is present in IgM, which has no hinge region. The immunoglobulin heavy chain constant region useful in the practice of the invention can comprise an immunoglobulin hinge region, and preferably also includes a CH3 domain. The immunoglobulin heavy chain constant region can comprise an immunoglobulin hinge region, a CH2 domain and a CH3 domain. As used herein, the term. immunoglobulin "hinge region" is understood to mean an entire immunoglobulin hinge region or at least a portion of the immunoglobulin hinge region sufficient to form one or more disulfide bonds with a second immunoglobulin hinge region.

Fc regions may be derived from antibodies belonging to each of the immunoglobulin classes referred to as IgA, IgD, IgE, IgG (e.g., subclasses IgG1, IgG2, IgG3, and IgG4), and IgM. The choice of appropriate Fe regions is discussed in detail in U.S. Pat. Nos. 5,541,087, and 5,726,044, the disclosures of which are incorporated herein by reference in their entirety.

In some embodiments, the fusion protein comprises the following amino acid sequence:

(SEQ ID NO: 171)
SGTLKKVAGALDGSVTFTLNITEIKVDYVVWTFNTFFLAMVKKDGVT

SQSSNKERIVFPDGLYSMKLSQLKKNDSGAYRAEIYSTSSQASLIQE

YVLHVYKHLSRPKVTIDRQSNKNGTCVINLTCSTDQDGENVTYSWKA

VGQGDNQFHDGATLSIAWRSGEKDQALTCMARNPVSNSFSTPVFPQK

LCEDAATDLTSLRGGCLPCICTVPEVSSVFIFPPKPKDVLTITLTPK

VTCVVVDISKDDPEVQFSWFVDDVEVHTAQTQPREEQFNSTFRSVSE

LPIMHQDWLNGKEFKCRVNSAAFPAPIEKTISKTKGRPKAPQVYTIP

PPKEQMAKDKVSLTCMMITDFFPEDITVEWQWNGQPAENYKNTQPIM

DTDGSYFVYSKLNVQKSNWEAGNTFTCSVLHEGLHNHHTEKSLSHSP

GK.

The murine ECD portion of the polypeptide is in bold. The remaining amino acid sequence corresponds to the murine IgG1 Fc portion of the fusion protein.

In some embodiments, the fusion protein is a fusion of two human protein components and comprises the following amino acid sequence:

(SEQ ID NO: 170)
SGPVKELVGSVGGAVTFPLKSKVKQVDSIVWTFNTTPLVTIQPEGGT

IIVTQNRNRERVDFPDGGYSLKLSKLKKNDSGIYYVGIYSSSLQQPS

TQEYVLHVYEHLSKPKVTMGLQSNKNGTCVTNLTCCMEHGEEDVIYT

WKALGQAANESHNGSILPISWRWGESDMTFICVARNPVSRNFSSPIL

ARKLCEGAADDPDSSMESKYGPPCPPCPAPEFEGGPSVFLFPPKPKD

TLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQP

REPQVYTLPPSQEEMTKNQVSLTCLVKGFYPSDIAVEWESNQGPENN

YKTTPPVLDSDGSFFLYSRLTVDKSRWQEGNVFSPSVMHEALHNHYT

QKSLSLSLGK.

The human ECD portion of the polypeptide is in bold. The remaining amino acid sequence corresponds to the human IgG4 Fc portion of the fusion protein, wherein the Fe constant regions comprises two substitutions: S228P and L235E.

It is understood that a fusion protein described herein can contain a signal peptide, e.g., an IL-12 signal peptide having the amino acid sequence:

(SEQ ID NO: 172)
MYRMQLLSCIALSLALVTNS.

It may be useful, in some circumstances, to modify the immunoglobulin heavy chain constant region, for example, by mutation, deletion or other changes mediated by genetic engineering or other approaches, so that certain activities, such as complement fixation or stimulation of antibody-dependent cell-mediated cytotoxicity (ADCC) are reduced or eliminated, while preferably preserving the Fc regions' ability to bind an Fe receptor (e.g., FcRn). In some embodiments, the Fe constant region can be altered in a way such that it does not homodimerize with another Fc constant region.

In some embodiments, the Fc region (including those of an antibody or antigen-binding fragment described herein) can be an altered Fc constant region having reduced (or no) effector function relative to its corresponding unaltered constant region. Effector functions involving the Fc constant region may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent. For example, an altered Fc constant region that displays modulated ADCC and/or CDC activity may exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the Fc constant region. An altered Fc region described herein may exhibit reduced or no measurable ADCC and/or CDC activity.

In certain embodiments, the altered constant region has at least one amino acid substitution, insertion, and/or deletion, compared to a native sequence constant region or to the unaltered constant region, e.g. from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that results in altered post-translational modifications, including, for example, an altered glycosylation pattern (e.g., the addition of one or more sugar components, the loss of one or more sugar components, or a change in composition of one or more sugar components relative to the unaltered constant region).

Altered Fc constant regions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2$^{nd}$ Edition," Cold Spring Harbor Laboratory Press, Cold Spring Harbor, N.Y.; PCT publication no. WO 06/53301; and U.S. Pat. No. 7,704,497, the disclosures of each of which are incorporated herein by reference in their entirety.

Altered Fc constant regions having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. According to these embodiments, the Fc constant region comprises a substitution to an alanine at position 234 or a mutation to an alanine at position 235. Additionally, the altered constant region may contain a double mutation: a mutation to an alanine at position 234 and a second mutation to an alanine at position 235. In one embodiment, the Fc constant region comprises an IgG4 framework, wherein the Ala-Ala mutation would describe a mutation(s) from phenylalanine to alanine at position 234 and/or a mutation from leucine to alanine at position 235. In another embodiment, the Fc constant region comprises an IgG1 framework, wherein the Ala-Ala mutation would describe a mutation(s) from leucine to alanine at position 234 and/or a mutation from leucine to alanine at position 235. An Fc constant region may alternatively or additionally carry other mutations, including the point mutation K322A in the CH2 domain (Hezareh et al. (2001) *J Virol* 75:12161-12168).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an altered Fc constant region (e.g., an altered human Fc constant region) can bind to neonatal Fc receptor (FcRn) with greater affinity than that of the native Fc constant region from which the altered or variant Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. See, e.g., Hinton et al. (2004) *J Biol Chem* 279:6213-6216 and Datta-Mannan et al. (2007) *Drug Metab Dispos* 35:1-9. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., Datta-Mannan et al. (2007) *J Biol Chem* 282(3): 1709-1717; International Publication No. WO 98/23289; International Publication No. WO 97/34631; and U.S. Pat. No. 6,277,375, the disclosures of each of which are incorporated herein by reference in their entirety.

Substitutions that enhance the binding affinity of an antibody Fc constant region for FcRn are known in the art and include, e.g., (1) the M252Y/S254T/TT256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments, the altered or variant Fc constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine, or histidine for aspartic acid at position 312;
lysine, or arginine for leucine at position 314; alanine, or histidine for asparagine at position 315;
alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380;
alanine for glutamic acid at position 382; alanine for asparagine or serine at position 384;
aspartic acid, or histidine for glycine at position 385; proline for glutamine at position 386;
glutamic acid for proline at position 387; alanine, or serine for asparagine at position 389;
alanine for serine at position 424;
alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

Expression and Purification of Recombinant Proteins

A recombinant polypeptide (e.g., fragments or fusion proteins) can be produced using a variety of techniques known in the art of molecular biology and protein chemistry. For example, a nucleic acid encoding a fusion protein can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of recombinant polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include CaPO4 precipitation, liposome fusion, cationic liposomes, electroporation, viral infection, dextran-mediated transfection, polybrene-mediated transfection, protoplast fusion, and direct microinjection.

Appropriate host cells for the expression of recombinant proteins include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, a recombinant protein can be expressed in, and purified from, transgenic animals (e.g., transgenic mammals). For example, a recombinant protein can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

A fusion protein can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, proteins expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. A fusion protein described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the recombinant proteins can be isolated. The term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryotic or eukaryotic cell expressing the proteins. Typically, a polypeptide is purified when it constitutes at least 60 (e.g., at least 65, 70, 75, 80, 85, 90, 92, 95, 97, or 99) %, by weight, of the total protein in a sample.

The recombinant proteins can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column) Ultrafiltration and diafiltration techniques, in conjunction with protein concentration, are also useful. See, e.g., Scopes (1994) "Protein Purification, 3' edition," Springer-Verlag, New York City, N.Y. The degree of purification necessary will vary depending on the desired use. In some instances, no purification of the expressed proteins will be necessary.

Methods for determining the yield or purity of a purified protein are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the protein preparations. Methods for removing endotoxin from a protein sample are known in the art and exemplified in the working examples. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Minus), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated.

Antibodies

In some embodiments, the agent that modulates (e.g., inhibits) the interaction between two CRACC proteins is an antibody or antigen-binding fragment thereof that binds to a CRACC protein (e.g., the ECD of a CRACC protein). As used herein, the term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to an target antigen (e.g., human CRACC protein and modulate (e.g., inhibit) the activity of the antigen (e.g., modulate its interaction with another CRACC protein). Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1): 47-66; Hudson and Kortt (1999) *J Immunol Methods* 231 (1):177-189; Poljak (1994) *Structure* 2(12):1121-1123; Rondon and Marasco (1997) *Annual Review of Microbiology* 51:257-283, the disclosures of each of which are incorporated herein by reference in their entirety. Bispecific antibodies (including DVD-Ig antibodies; see below) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

Suitable methods for producing an antibody, or antigen-binding fragments thereof, in accordance with the disclosure are known in the art and described herein. For example, monoclonal antibodies may be generated using cells that express a target antigen of interest, a target antigen (e.g., a polypeptide) of interest itself, or an antigenic fragment of the target antigen, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to the target antigen. The amino acid sequences for exemplary CRACC polypeptides (e.g., CRACC ECDs) are known in the art and described herein. Amino acid sequences for PD-1, PD-1L, and PD-L2 (e.g., human proteins) are well known in the art. For example, an exemplary amino acid sequence for human PD-1 is as follows:

(UniProt ID: Q15116)
(SEQ ID NO: 10)
MQIPQAPWPVVWAVLQLGWRPGWFLDSPDRPWNPPTFSPALLVVTEG

DNATFTCSFSNTSESFVLNWYRMSPSNQTDKLAAFPEDRSQPGQDCR

FRVTQLPNGRDFHMSVVRARRNDSGTYLCGAISLAPKAQIKESLRAE

LRVTERRAEVPTAHPSPSPRPAGQFQTLVVGVVGGLLGSLVLLVWVL

AVICSRAARGTIGARRTGQPLKEDPSAVPVFSVDYGELDFQWREKTP

EPPVPCVPEQTEYATIVFPSGMGTSSPARRGSADGPRSAQPLRPEDG

HCSWPL.

The signal peptide of the molecule is underlined above.

Moreover, antibodies derived from recombinant libraries ("phage antibodies") may be selected using target antigen-expressing cells, or polypeptides derived therefrom, as bait to isolate the antibodies or polypeptides on the basis of target specificity. The production and isolation of non-human and chimeric antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g., *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J Biol Chem* 263:4318-4322; U.S. Pat. Nos. 5,403,484; 5,223,409; WO88/06630; WO92/15679; U.S. Pat. Nos. 5,780,279; 5,571,698; 6,040,136; Davis et al. (1999) *Cancer Metastasis Rev* 18(4):421-5; Taylor et al. (1992) *Nucleic Acids Res* 20: 6287-6295; and Tomizuka et al. (2000) *Proc Natl Acad Sci*

USA 97(2): 722-727, the contents of each of which are incorporated herein by reference in their entirety.

The cell culture supernatants are screened for the desired antibodies, e.g., by immunofluorescent staining of target antigen-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a target antigen-expressing cell line, or with Protein-A or -G.

Another embodiment provides a process for the preparation of a bacterial cell line secreting antibodies directed against a target antigen in a suitable mammal. For example, a rabbit is immunized with pooled samples from target antigen-expressing tissue or cells or the target antigen itself (or fragments thereof). A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a target antigen of interest. In that process, a suitable mammal, for example a Balb/c mouse, is immunized with, e.g., a target antigen of interest (or an antigenic fragment thereof) as described. Antibody-producing cells of the immunized mammal are grown briefly in culture or fused with cells of a suitable myeloma cell line. The hybrid cells obtained in the fusion are cloned, and cell clones secreting the desired antibodies are selected. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally an immunogenic composition several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human) Chimeric antibodies can be produced with mouse variable regions of desired specificity spliced onto human constant domain gene segments (for example, U.S. Pat. No. 4,816,567). In this manner, non-human antibodies can be modified to make them more suitable for human clinical application (e.g., methods for treating or preventing an immune associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321: 522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc Natl Acad Sci USA* 90:2551; Jakobovits et al. (1993) *Nature* 362:255-258; Bruggemann et al. (1993) *Year in Immunol* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target antigen to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227:381; Marks et al. (1991) *J Mol Biol* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132; 6,680,209; and 4,634,666, and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156 and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 20030229905 A1, 20040010810 A1, 20040093622 A1, 20060040363 A1, 20050054055 A1, 20050076395 A1, and 20050287630 A1. See also International Patent Application Publication Nos. WO 94/02602, WO 96/34096, and WO 98/24893, and European Patent No. EP 0 463 151 B 1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B 1, International Patent Application Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5:647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *Int Immunol* 6: 579-591; Tuaillon et al. (1995) *J Immunol* 154: 6453-65; Fishwild et al. (1996) *Nature Biotechnol* 14: 845; and Tuaillon et al. (2000) *Eur J Immunol* 10: 2998-3005, the disclosures of each of which are hereby incorporated by reference in their entirety.

In certain embodiments, de-immunized antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human) De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, and artificially selected antibodies), synthetic antibodies and semi-synthetic antibodies.

In some embodiments, a recombinant DNA comprising an insert coding for a heavy chain variable domain and/or for a light chain variable domain of an antibody is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of antibodies can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or the CDRs of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided. Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an antibody or antigen-binding fragment (e.g., Fab, Fv, single-chain (scFv), Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA*, 78:2072-2076) or Tn5 neo (Southern and Berg (1982) *J Mol Appl Genet* 1:327-341). The selectable marker gene can be either linked to the DNA gene sequences to be expressed, or introduced into the same cell by co-transfection (Wigler et al. (1979) *Cell* 16:777-785). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147-7151), polyoma virus (Deans et al. (1984) *Proc Natl Acad Sci USA* 81:1292-1296), or SV40 virus (Lusky and Botchan (1981) *Nature* 293:79-81).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280-289; Cepko et al. (1984) *Cell* 37:1053-1062; and Kaufman (1985) *Proc Natl Acad Sci USA* 82:689-693.

As is evident from the disclosure, the antibodies can be used in therapies (e.g., therapies for an immune associated disorder), including combination therapies.

The disclosure also provides camelid or dromedary antibodies (e.g., antibodies derived from *Camelus bactrianus, Calelus dromaderius*, or *lama paccos*). Such antibodies, unlike the typical two-chain (fragment) or four-chain (whole antibody) antibodies from most mammals, generally lack light chains. See U.S. Pat. No. 5,759,808; Stijlemans et al. (2004) *J Biol Chem* 279:1256-1261; Dumoulin et al. (2003) *Nature* 424:783-788; and Pleschberger et al. (2003) *Bioconjugate Chem* 14:440-448. Engineered libraries of camelid antibodies and antibody fragments are commercially available, for example, from Ablynx (Ghent, Belgium). As with other antibodies of non-human origin, an amino acid sequence of a camelid antibody can be altered recombinantly to obtain a sequence that more closely resembles a human sequence, i.e., the nanobody can be "humanized" to thereby further reduce the potential immunogenicity of the antibody.

In the therapeutic embodiments of the present disclosure, bispecific antibodies are contemplated (e.g., a bispecific antibody that binds to a CRACC protein and to PD-1, PD-L1, or PD-L2). Bispecific antibodies are monoclonal, preferably human or humanized, antibodies that have binding specificities for at least two different epitopes. Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods Enzymol* 121:210-228; PCT Publication No. WO 96/27011; Brennan et al. (1985) *Science* 229:81-83; Shalaby et al. *J Exp Med* (1992) 175:217-225; Kostelny et al. (1992) *J Immunol* 148(5): 1547-1553; Hollinger et al. (1993) *Proc Natl Acad Sci USA* 90:6444-6448; Gruber et al. (1994) *J Immunol* 152:5368-5474; and Tutt et al. (1991) *J Immunol* 147:60-69. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl *Acad Sci* USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 1152:5368-5374. Alternatively, the antibodies can be "linear antibodies" as described in, e.g., Zapata et al. (1995) *Protein Eng* 8(10): 1057-1062. Briefly, these antibodies comprise a pair of tandem Fd segments ($V_H$-$C_H$1-$V_H$-$C_H$1) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. The light chain is paired to a corresponding heavy chain containing the VH regions from the parent antibodies. Methods for generating DVD-Ig molecules from two parent antibodies are further described in, e.g., PCT Publication Nos. WO 08/024188 and WO 07/024715, the disclosures of each of which are incorporated herein by reference in their entirety.

In some embodiments, an antibody, or antigen-binding fragment thereof, described herein can comprise an altered or variant Fc constant region (as discussed above), e.g., one which has reduced or no ADCC/CDC activity or increased affinity for FcRn.

In some embodiments, an antibody specifically binds to a protein of interest (e.g., the human CRACC ECD protein having the amino acid sequence depicted in SEQ ID NO:2). The terms "specific binding," "specifically binds," and like grammatical terms, as used herein, refer to two molecules forming a complex that is relatively stable under physiologic conditions. Typically, binding is considered specific when the association constant ($k_a$) is higher than $10^6$ $M^{-1}s^{-1}$. Thus, an antibody can specifically bind to a protein with a $k_a$ of at least (or greater than) 106 (e.g., at least or greater than $10^7$, $10^8$, $10^9$, $10^{10}$, $10^{11}$, $10^{12}$, $10^{13}$, $10^{14}$, or $10^{15}$ or higher) $M^{-1}s^{-1}$. In some embodiments, an antibody described herein has a dissociation constant ($k_d$) of less than or equal to $10^{-3}$ (e.g., $8\times10^{-4}$, $5\times10^{-4}$, $2\times10^{-4}$, $10^{-4}$, or $10^{-5}$) $s^{-1}$.

In some embodiments, an antibody described herein has a $K_D$ of less than $10^{-8}$, $10^{-9}$, $10^{-10}$, $10^{-11}$, or $10^{-12}$ M. The equilibrium constant $K_D$ is the ratio of the kinetic rate constants—$k_d/k_a$. In some embodiments, an antibody described herein has a $K_D$ of less than $1\times10^{-9}$ M.

Methods for determining whether an antibody binds to a target antigen and/or the affinity for an antibody to a target antigen are known in the art. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) *J. Immunol. Meth.* 160:191-198; Jonsson et al. (1993) *Ann. Biol. Clin.* 51:19-26; and Jonsson et al. (1991) *Biotechniques* 11:620-627. See also, U.S. Pat. No. 6,355,245.

In some embodiments, an antibody can crossblock binding of another antibody that binds to an epitope within, or overlapping with, a target antigen of interest (e.g., a human CRACC protein). In some embodiments, the anti-CRACC antibody can crossblock binding of an antibody that binds to an epitope within, or overlapping with, a peptide fragment of a CRACC protein. As used herein, the term "crossblocking antibody" refers to a first antibody that lowers the amount of binding of a second antibody to an epitope of a target antigen relative to the amount of binding of the second antibody to the epitope in the absence of the first antibody. Suitable methods for determining whether a first antibody crossblocks binding of a second antibody to an epitope are known in the art. For example, crossblocking antibodies can be identified by comparing the binding of a known anti-CRACC antibody in the presence and absence of a test antibody. Decreased binding of the known antibody in the presence of the test antibody as compared to binding of the known antibody in the absence of the test antibody indicates the test antibody is a crossblocking antibody.

Methods for identifying the epitope to which a particular antibody binds are also known in the art. For example, the binding epitope of an anti-CRACC antibody can be identified by measuring the binding of the antibody to several (e.g., three, four, five, six, seven, eight, nine, 10, 15, 20, or 30 or more) overlapping peptide fragments of a CRACC protein. Each of the different overlapping peptides is then bound to a unique address on a solid support, e.g., separate wells of a multi-well assay plate. Next, the anti-CRACC antibody is interrogated by contacting it to each of the peptides in the assay plate for an amount of time and under conditions that allow for the antibody to bind to its epitope. Unbound anti-CRACC antibody is removed by washing each of the wells. Next, a detectably-labeled secondary antibody that binds to the anti-CRACC antibody, if present in a well of the plate, is contacted to each of the wells, and unbound secondary antibody is removed by washing steps. The presence or amount of the detectable signal produced by the detectably-labeled secondary antibody in a well is an indication that the anti-CRACC antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J. Immunol. Methods* 160:20191-8).

In some embodiments, the inhibitor molecule is a non-antibody, scaffold protein. These proteins are, generally, obtained through combinatorial chemistry-based adaptation of pre-existing antigen-binding proteins. For example, the binding site of human transferrin for human transferrin receptor can be modified using combinatorial chemistry to create a diverse library of transferrin variants, some of which have acquired affinity for different antigens. Ali et al. (1999) *J Biol Chem* 274:24066-24073. The portion of human transferrin not involved with bind the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest. Hey et al. (2005) *TRENDS Biotechnol* 23(10):514-522.

One of skill in the art would appreciate that the scaffold portion of the non-antibody scaffold protein can include, e.g., all or part of: the Z domain of *S. aureus* protein A, human transferrin, human tenth fibronectin type III domain, kunitz domain of a human trypsin inhibitor, human CTLA-4, an akyrin repeat protein, a human lipocalin, human crystallin, human ubiquitin, or a trypsin inhibitor from *E. elaterium*. Id.

In some embodiments, an antibody or antigen-binding fragment thereof described herein is cross-reactive. The term "cross-reactive antibody," as used herein, refers to an antibody capable of binding to a cross-reactive antigenic determinant. In some embodiments, an antibody or antigen-binding fragment thereof is cross-reactive for CRACC polypeptides of different species. For example, an anti-CRACC antibody can bind to a human CRACC protein and a CRACC protein from a non-human primate, such as Rhesus or Cynomolgus macaque. In some embodiments, an antibody or antigen-binding fragment thereof described herein can bind to a CRACC polypeptide from human and rodent (e.g., mouse or rat) origin.

Test Compounds and Methods for Screening

The disclosure also features methods for identifying a compound that modulates the activation of an immune cell. The methods comprise: (i) in the presence of an antigen, contacting an immune cell with a test compound and (ii) detecting activation of the immune cell in the presence of the test compound and antigen, wherein a change in the level or duration of activation by the immune cell in the presence of the test compound and antigen, as compared to the level or duration of activation in the presence of the antigen and absence of the test compound, indicates that the test compound is a compound that modulates the activation of an immune cell by the antigen. The test compound can be one that binds to a CRACC polypeptide and/or inhibits the homophilic interaction between two CRACC polypeptides.

A test compound described herein can be, e.g., a small molecule, a protein, a protein fragment, a polypeptide, a peptide, a polypeptide analog, a peptidomimetic, a nucleic acid, a nucleic acid analog, a macrocyle compound, an aptamer including but not limited to an RNA aptamer including an L-RNA aptamer, a spiegelmer, a locked nucleic acid (LNA), a peptide nucleic acid (PNA), or an antibody. In some embodiments, the small molecule can be a non-antibody antigen-binding protein, e.g., one of the antibody-related scaffold protein constructs as described in Hey et al. (2005) *TRENDS in Biotechnology* 23(1):514-522.

Methods for determining whether a compound binds to a target protein and/or the affinity for an agent for a target protein are known in the art (it is understood that such methods are also useful for measuring the interaction between two CRACC polypeptides, and inhibition thereof). For example, the binding of an agent to a target protein can be detected and/or quantified using a variety of techniques such as, but not limited to, BioLayer Interferometry (BLI), Western blot, dot blot, surface plasmon resonance method (SPR), enzyme-linked immunosorbent assay (ELISA), AlphaScreen® or AlphaLISA® assays, or mass spectrometry based methods.

In some embodiments, binding can be assayed using any SPR-based assays known in the art for characterizing the kinetic parameters of the interaction of the compound with a CRACC protein. Any SPR instrument commercially available including, but not limited to, BIAcore Instruments (Biacore AB; Uppsala, Sweden); 1Asys instruments (Affinity Sensors; Franklin, Massachusetts); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) *Methods* 22: 77-91; Dong et al. (2002) *Reviews in Mol Biotech* 82: 303-323; Fivash et al. (1998) *Curr Opin Biotechnol* 9: 97-101; and Rich et al. (2000) *Curr Opin Biotechnol* 11: 54-61.

In some embodiments, the biomolecular interactions between a compound and a CRACC protein can be assayed using BLI on an Octet (ForteBio Inc.). BLI is a label-free optical analytical technique that senses binding between a ligand (such as a CRACC polypeptide) that is immobilized on a biosensor tip and an analyte (such as a test compound) in solution by measuring the change in the thickness of the protein layer on the biosensor tip in real-time.

In some embodiments, AlphaScreen (PerkinElmer) assays can be used to characterize binding of compounds to CRACC proteins. The acronym ALPHA stands for Amplified Luminescent Proximity Homogeneous Assay. AlphaScreen is a bead-based proximity assay that senses binding between molecules (such as a CRACC polypeptide and a test compound) attached to donor and acceptor beads by measuring the signal produced by energy transfer between the donor and acceptor beads. (See e.g., Eglen et al. (2008) *Curr Chem Genomics* 1:2-10).

In some embodiments, AlphaLISA® (PerkinElmer) assays can be used to characterize binding of compounds to CRACC polypeptides. AlphaLISA is modified from the AlphaScreen assay described above to include europium-containing acceptor beads and functions as an alternative to traditional ELISA assays. (See, e.g., Eglen et al. (2008) *Curr Chem Genomics* 1:2-10.)

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA) and microparticle enzyme immunoassay (MEIA), furthermore capillary electrophoresis immunoassays (CEIA), radio-immunoassays (RIA), immunoradiometric assays (IRMA), fluorescence polarization immunoassays (FPIA) and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of protein/antibody complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

In some embodiments, binding of test compounds to CRACC polypeptides can be assayed using thermodenaturation methods involving differential scanning fluorimetry (DSF) and differential static light scattering (DSLS).

In some embodiments, binding of test compounds to CRACC polypeptides can be assayed using a mass spectrometry based method such as, but not limited to, an affinity selection coupled to mass spectrometry (AS-MS) platform. This is a label-free method where the protein and test compound are incubated, unbound molecules are washed away and protein-ligand complexes are analyzed by MS for ligand identification following a decomplexation step.

In some embodiments, binding of test compounds to CRACC polypeptides can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled CRACC polypeptide or test compound, by immunoassay, or by chromatographic detection.

In some embodiments, the present invention contemplates the use of fluorescence polarization assays and fluorescence resonance energy transfer (FRET) assays in measuring, either directly or indirectly, the degree of interaction between a CRACC polypeptide and a test compound.

The screening assays may also involve detecting and/or measuring the biological activity or activation (e.g., modulation of the activation) of an immune cell, e.g., a T cell, an NK cell, or a dendritic cell (e.g., dendritic cell maturation). Methods for detecting or measuring the biological activity and activation state of immune cells are known in the art, described herein, and exemplified in the working examples. Biological activities can include, for example, the induction of proliferation, the induction of signaling, the induction of expression of activation markers, the induction of cytokine secretion, and/or the induction of lysis of target cells. In some embodiments, the biological activity detected or measured is the production of one or more cytokines selected from the group consisting of IL-2, IFNγ, and TNFα. Methods for detecting and/or measuring the expression of such cytokines by immune cells are exemplified in the working examples. Such methods include, e.g., intracellular staining coupled FACS.

All of the above embodiments are suitable for development into high-throughput platforms. Methods for further characterizing the CRACC-inhibitory activity of compounds identified using the above methods are described herein and are known in the art.

Biological Samples and Sample Collection

Suitable biological samples for use in the methods described herein include, e.g., any biological fluid. A biological sample can be, for example, a specimen obtained from a subject (e.g., a mammal such as a human) or can be derived from such a subject. A biological sample can also be a biological fluid such as urine, whole blood or a fraction thereof (e.g., plasma or serum), saliva, semen, sputum, cerebrospinal fluid, tears, or mucus. A biological sample can be further fractionated, if desired, to a fraction containing particular analytes (e.g., proteins) of interest. For example, a whole blood sample can be fractionated into serum or into fractions containing particular types of proteins. If desired, a biological sample can be a combination of different biological samples from a subject such as a combination of two different fluids.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, a cancer or an infection (e.g., a viral infection). Any suitable methods for obtaining the biological samples can be employed, although exemplary methods include, e.g., phlebotomy, swab (e.g., buccal swab), lavage, or fine needle aspirate biopsy procedure. Biological samples can also be obtained from bone marrow or spleen.

In some embodiments, a protein extract may be prepared from a biological sample. In some embodiments, a protein extract contains the total protein content. Methods of protein extraction are well known in the art. See, e.g., Roe (2001) "Protein Purification Techniques: A Practical Approach", 2nd Edition, Oxford University Press. Numerous different and versatile kits can be used to extract proteins from bodily fluids and tissues, and are commercially-available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of Methods in molecular biology, Humana Press; Masters (2000) "Animal cell culture: a practical approach," volume 232 of Practical approach series, Oxford University Press; and Jones (1996) "Human cell culture protocols," volume 2 of Methods in molecular medicine, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Pharmaceutical Compositions and Formulations

The compositions described herein can be formulated as a pharmaceutical solution, e.g., for administration to a subject for modulating (e.g., enhancing) an immune response to an antigen. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filtered sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions described herein are administered in an aqueous solution by parenteral injection. The disclosure features pharmaceutical compositions comprising an effective amount of the agent (or more than one agent) and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid. sodium metabisulfite), and preservatives (e.g., thimersol, benzyl alcohol) and bulking substances (e.g., lactose, mannitol). The formulations may be sterilized, e.g., using filtration, incorporating sterilizing agents into the compositions, by irradiating the compositions. or by heating the compositions.

As described above, relatively high concentration compositions can be made. For example, the compositions can be formulated at a concentration of the active agent of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, Drugs and the Pharmaceutical Sciences, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc. Natl. Acad. Sci. USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In some embodiments, compositions can be formulated with one or more additional therapeutic agents, e.g., additional agents for stimulating an immune response in a subject, e.g., adjuvants and excipients. In some embodiments, the compositions can be formulated with an inhibitor of the interaction between PD-1 and one its natural ligands, such as PD-L1 or PD-L2. Exemplary PD-1/PD-L1 inhibitors (e.g., anti-PD-1 and/or anti-PD-L1 antibodies) are known in the art and described in, e.g., International Patent Application Publication Nos. WO 2010036959 and WO 2013/079174, as well as U.S. Pat. Nos. 8,552,154 and 7,521,051, the disclosures of each of which as they relate to the antibody descriptions are incorporated herein by reference in their entirety.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

Applications

The agents (e.g., anti-CRACC antibodies and fusion proteins comprising all or part of the CRACC ECD) can be used in a number of in vitro, ex vivo, and in vivo applications. For example, the agents described herein can be used to detect CRACC polypeptides, e.g., the expression of a CRACC polypeptide by a cell of interest. In some embodiments, the agents can be contacted to cultured cells in vitro or in vivo, or administered to a subject (e.g., a mammal, such as a human) to modulate the activation of an immune cell and/or modulate an immune response to an antigen of interest. For example, in the presence of an antigen of interest (or more than one antigen of interest), contacting an immune cell with an effective amount of an agent (that inhibits an interaction between two CRACC polypeptides) to thereby modulate activation of the immune cell by the antigen. The effective amount of the agent is the amount required to modulate the activation of the immune cell by the antigen, that is, to produce an enhanced or reduced activation level in response to the antigen as compared to the level of activation produced by the immune cell in response to the antigen in the absence of the agent.

As used herein, the term "immune cell" refers to cells that play a role in the immune response Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the immune cell is a T cell (e.g., a $CD8^+$ T cell, a $CD3^+CD8^+$ T cell, a naïve T cell, or an NK cell). In some embodiments, the immune cell is a macrophage or a dendritic cell. Naïve T cells are mature T cells which have not yet encountered their cognate antigen within the periphery.

As used herein, the term "immune response" refers to the biological functions of immune cells (including macromolecules produced by such immune cells or the liver, such as antibodies, cytokines, and complement proteins) that result in selective damage to, destruction of, or elimination from the human body of invading pathogens, cells or tissues infected with pathogens, cancerous cells, or, in cases of autoimmunity or pathological inflammation, normal human cells or tissues. In some embodiments, the immune response is an innate immune response. In some embodiments, the immune response is a T cell response, e.g., a memory T cell response. In some embodiments, the immune response is a humoral immune response.

Immune cell activation (e.g., T cell activation) or like grammatical terms refers to one or more cellular responses of the subject immune cell, such as proliferation, maturation, differentiation, cytokine secretion, cytotoxic effector molecule release, cytotoxic activity, and expression of activation or differentiation markers. Suitable methods to measure activation of an immune cell (e.g., T cell activation, NK activation, or dendritic cell maturation) are known in the art and described in the working examples.

An antigen is any substance that will induce a detectable (or measurable) immune response (e.g., humoral and/or cellular) when administered to a mammal. For example, an antigen may be capable of inducing a measurable antibody response by the mammal to which the antigen is administered. An effective amount of an antigen is one that is sufficient to activate an immune cell in culture and/or, in the in viva setting, capable of inducing a measurable immune response by a mammal to the antigen. Representative antigens include peptides, proteins, polysaccharides, saccharides, lipids, nucleic acids, or combinations thereof. The antigen can be derived from a tumor or from a transformed cell such as a cancer or leukemic cell and can be a whole cell or immunogenic component thereof, e.g., cell wall components or molecular components thereof.

Suitable antigens are known in the art and are available from commercial sources. The antigens may be purified or partially purified polypeptides derived from tumors or other sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. An antigen can have one or more epitopes, each of which being capable of inducing an immune response. In some embodiments, the antigen is an attenuated or killed microorganism, or a protein (or antigenic fragment thereof) derived from a microorganism. While in no way limiting, exemplary antigens can include proteins, carbohydrates, or lipids from any one of the following: viruses (e.g., HIV, rotavirus, influenza, parainfluenza, herpes (e.g., VZV, HSV-1, HAV-6, CMV, and Epstein Barr virus) Chicken pox, small pox, rabies, polio, Hepatitis A, Hepatitis B, Hepatitis C, measles, Dengue, mumps, Coxsackie virus, flaviviruses, adenoviruses, distemper, reovirus, respiratory syncytial virus, ebola, hanta virus, papillomavirus, and parvovirus), bacteria (e.g., *Bordetella pertussis, Brucella abortis, Escherichia coli, Salmonella* species, *Streptococci, Cholera, Shigella, Pseudomonas, Tuberculosis, Pertussis*, pneumonococci, meningococci, *Klebsiella proteus, legionella*, anthrax, leptospirosis), parasites (e.g., *Plasmodium. falciparum, P. vivax, P. malariae, Entamoeba histolytica, Balantidium coli, Naegleria fowleri, Acanthamoeba* sp., *Giardia Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*), or *Candida* (e.g., *albicans, krusei, glabrata*, or *tropicalis*), *Cryptococcus neoformans, Aspergillus* (e.g., *fumigants* or *niger*), *Mucorales* (e.g., *mucor, absidia, rhizophus*), *Sporothrix schenkii, Blastomyces dermataidis, Paracoccidioides brasiliensis, Coccidioides immitis*, or *Histoplasma capsulatum*). Antigens also include *Sporozoan antigens, Plasmodium* antigens, such as all or a portion of Circumsporozoite protein, a Sporozoite surface protein, a liver stage antigen, an apical membrane associated protein, or a Merozoite surface protein. It is understood that a mammal described herein can, in some embodiments, be one infected with any of the foregoing microorganisms.

In some embodiments, the antigen is a tumor antigen, including: alpha-actinin-4, Bcr-Abl, Casp-8, beta-catenin, cdc27, cdk4, cdkn2a, coa-1, dek-can, EF2, ETV6-AML1, LDLR-fucosyltransferaseAS, HLA-A2, HLA-All, hsp70-2, KIAAO205, Mart2, Mum-1, 2, and 3, neo-PAP, myosin class I, OS-9, pm1-RARα, PTPRK, K-ras, N-ras, Triosephosphate isomerase, Bage-1, Gage 3,4,5,6,7, GnTV, Herv-K-me1, Lage-1, Mage-A1,2,3,4,6,10,12, Mage-C2, NA-88, NY-Eso-1/Lage-2, SP17, SSX-2, and TRP2-Int2, MelanA (MART-1), gp100 (Pmel 17), tyrosinase, TRP-L TRP-2, MAGE-1, MAGE-3, BAG, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein/cyclophilin C-associated protein), TAAL6, TAG72, TLP, and TPS.

In some embodiments, the agent can be contacted to a plurality of immune cells, which plurality comprises T cells (e.g., $CD8^+$ T cells) and antigen presenting cells. For example, the plurality can be a population of splenocytes or peripheral blood mononuclear cells (PBMCs). The contacting can occur in the presence of one or more antigens of interest.

In some embodiments, the immune cell or plurality of immune cells is obtained from a mammal who has been exposed to the antigen or antigens of interest prior to the cells being obtained and, optionally, such prior exposure to the antigen resulted in the production of a measurable immune response to the antigen or antigens, e.g., the production of antibodies against the antigen or antigens. In some embodiments, the immune cell or plurality of cells is obtained from a patient known to be infected with a virus, such as HIV-1. In some embodiments, the immune cell or plurality of immune cells is obtained from a patient with a cancer (e.g., a colon, brain, stomach, liver, pancreatic, skin, ocular, stomach, lung, esophageal, or hematologic cancer).

In some embodiments, the contacting can occur in the further presence of an agent that interferes with the interaction between PD-1, PD-L1, and PD-L2. Such agents are known in the art and discussed supra.

Methods for Modulating an Immune Response

The above-described compositions are also useful to modulate (e.g., enhance) an immune response in a mammal. For example, an effective amount of an antigen and an effective amount of an agent can be administered to a mammal, wherein the immune response to the antigen by the mammal is enhanced in the presence of the agent. In some embodiments, the agent is administered first in time and the antigen is administered second in time. In some embodiments, the antigen is administered first in time and the agent is administered second in time. In some embodiments, the agent and antigen are administered to the mammal by different medical professionals. In some embodiments, the agent and the antigen are administered to the mammal by the same medical professional (e.g., at the same time). In some embodiments, the agent and the antigen are administered to the mammal at different times (optionally by different routes of administration), but not more than 30 (e.g., not more than 29, 28, 27, 26, 25, 24, 23, 22, 21, 20, 19, 18, 17, 16, 15, 14, 13, 12, 11, 10, 9, 8, 7, 6, 5, 4, 3, 2, or 1) day(s) apart. In some embodiments, the agent and antigen are administered at different times, but within 48 (e.g., 40, 36, 30, 24, 20, 18, 16, 14, 12, 11, 10, 9, 8, 7, 6, 5, 4, 3, 2, or 1) hour(s) of each other.

In some embodiments, more than one dose of the agent is administered to the mammal. In some embodiments, more than one dose of the antigen is administered to the mammal. In some embodiments, more than one dose of the agent and more than one dose of the antigen are administered to the mammal.

In some embodiments, the antigen and agent can be administered to the mammal using different routes of administration. For example, the antigen can be administered subcutaneously or intramuscularly and the agent can be administered intravenously.

As used herein, a mammal can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant).

As used herein, a subject mammal "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (e.g., vaccination with an antigen of interest in conjunction with an agent that inhibits the interaction between two CRACC proteins).

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition. Preventing also includes reducing the likelihood of becoming productively infected by a microorganism against which the subject was immunized (e.g., by administration of an antigen from the microorganism in conjunction with an agent that inhibits an interaction between two CRACC proteins).

In some embodiments, the mammal is one who has, is suspected of having, or is at risk for developing a cancer or an infection.

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer a genetic predisposition to develop a cancer such as a mutation in a tumor suppressor gene (e.g., mutation in BRCA1, p53, RB, or APC) or has been exposed to conditions that can result in the condition. Thus, a subject can be one "at risk of developing a cancer when the subject has been exposed to mutagenic or carcinogenic levels of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

Similarly, a mammal at risk for developing an infection is one having one or more risk factors that increase the likelihood of exposure to a pathogenic microorganism.

A subject "suspected of having" a cancer or an infection is one having one or more symptoms of the cancer or infection. It should be understood that mammal at risk for developing, or suspected of having, a cancer or an infection does not include all mammals within the species of interest.

In some embodiments, the methods include determining whether the subject mammal has a cancer or an infection.

In some embodiments, the mammal is afflicted with a persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In addition, bacterial, fungal and other pathogenic infections are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinbaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague),

*Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus enterotoxin* B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium*.

As described in the working examples, the inventors have discovered that patients afflicted with a viral infection (e.g., HIV-1 infection) have a higher concentration of CRACC-expressing immune cells than non-infected humans Thus, the disclosure also features methods for enhancing an immune response in mammals afflicted with an infection (e.g., a viral, bacterial, or parasitic infection) or cancer (or in mammals at risk of developing a cancer or an infection, e.g., a viral infection, such as HIV-1, herpes, papillomavirus, or hepatitis infection) by administering to the mammal an effective amount of an agent that inhibits the interaction between a first and second CRACC protein. Suitable agents are described herein and include, e.g., an anti-CRACC siRNA, an anti-CRACC antibody, or antigen-binding fragment thereof, and a fusion protein comprising all or part of a CRACC ECD.

In some embodiments, T cells (e.g., CD8$^+$ T cells) from the infected (or cancer-carrying) mammals express higher levels of a CRACC polypeptide than T cells of the same histological type from a mammal that is not infected (or cancer carrying). In some embodiments, the cells express at least 5 (e.g., at least 10, 15, 20, 25, 30, 35, 40, 45, 50, 60, 70, 80, 90, or 100) % greater levels of a CRACC polypeptide, relative to cells of the same histological type from a healthy mammal of the same species. In some embodiments, the immune cells express at least 2 (e.g., at least 3, 4, 5, 6, 7, 8, 9, 10, 15, 20, 25, 30, 50, or 100) times the amount of a CRACC polypeptide relative to cells of the same histological type from a healthy mammal of the same species. In some embodiments, the methods can include measuring the level of expression (e.g., mRNA or protein expression) of a CRACC polypeptide by cells from the subject mammal. In some embodiments, the methods include administering the agent to a mammal afflicted with an infection or cancer, wherein the mammal is one who has immune cells that overexpress a CRACC polypeptide. Suitable methods for measuring the expression level of an mRNA or protein are well known in the art.

In some embodiments, the mammal is infected with HIV-1.

In some embodiments, the methods can include monitoring a mammal (e.g., a human patient) for modulation (e.g., enhancement) of an immune response to an antigen of interest. In some embodiments, for example, embodiments in which the mammal has an infection or a cancer, the methods can include evaluating the mammal for a change in a disease parameter, e.g., an improvement in one or more symptoms of a given disorder. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer or an infection.

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen. The precise dosage will vary according to a variety of factors such as subject-dependent variables (e.g., age, immune system health, etc.), the disease, and the treatment being effected. Therapeutically effective amounts of the agents disclosed herein enhance an immune response by a mammal to a target antigen.

Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of cancer, vaccination, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibits a high therapeutic index are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, an agent can be administered to a mammal in conjunction with one or more additional therapeutic agents (e.g., therapeutic agents for treating an infection or treating cancer).

The following examples are intended to illustrate, not to limit, this disclosure.

EXAMPLES

Example 1. Materials and Methods

Vector Construction

The following adenovirus constructs were used in the experiments described herein: rAd5-Null (an adenovirus construct encoding no additional exogenous protein and used as a control in the experiments), rAd5-EAT2 (a recombinant adenovirus construct further encoding murine EAT-2 protein), and rAd5-HIV/Gag (a recombinant adenovirus construct further encoding the HIV-1 clade B Gag protein). Methods for expression and purification of these recombinant viruses are described, in, among other references, Aldhamen et al. (2011) *J Immunol* 186:722-732; Aldhamen et al. (2012) *J Immunol* 189:1349-1359; and Aldhamen et al. (2013) *Cancer Gene Ther* 20:564-575. Construction of these viruses involved inserting a nucleotide sequence encoding HXB2 Gag (nucleotides 790-2292 of the nucleotide sequence set forth in Genbank accession no. K03455) or EAT-2 [(Genbank accession No. NP_036139.3)

(SEQ ID NO: 12)
MDLPYYHGCLTKRECEALLLKGGVDGNFLIRDSESVPGALCLCVSFK

KLVYSYRIFREKHGYYRIETNAHTPRTIFPNLQELVSKYGKPGQGLV

VHLSNPIMRNNLCQRGRRMELELNVYENTDKEYVDVLP]

into the EcoRV site of pShuttle-CMV (Agilent Technologies, Santa Clara, Calif.) using standard molecular biology techniques. Sequence integrity and correct orientation of the nucleotide sequences within the vectors were confirmed by restriction digests and sequencing (pShuttle-CMV-Gag and pShuttle-CMV-EAT-2). The resulting shuttle plasmids were linearized using the PmeI restriction enzyme and homologously recombined with the pAdEasyI Ad5 vector genome, resulting in the pAd-Gag and pAd-EAT2 constructs (see a description of the pAdEasy system in, e.g., He et al. (1998) *Proc Natl Acad Sci USA* 95:2509-2514). HEK293 cells were transfected with PacI linearized plasmid and viable virus titers were amplified by several rounds of expanding infection. Viruses were purified from culture medium using a cesium chloride ($CsCl_2$) gradient as described in Ng and Graham (2002) *Methods Mol Med* 69:389-414. Gag expression was verified by Western blot. All viral preparations were found to be free of replication competent virus (RCA) both by RCA polymerase chain reaction (PCR) (through adenovirus E1 region amplification) and direct sequencing methods as described in Seregin et al. (2009) *Mol Ther* 17:685-696. The preparations were further tested for the presence of bacterial endotoxin as described in Seregin et al. (supra) and were found to contain <0.15 EU per ml. The infectivity of all recombinant adenoviruses used was confirmed by infectious units (50% tissue culture infective dose ($TCID_{50}$)) and transducing units titer assays. The vp/TCID was similar between all the recombinant virus preparations. Viral particle (VP) titers were further quantified by spectrophotometry and validated using sodium dodecyl sulfate polyacryrlamide gel electrophoresis (SDS-PAGE) of purified Ads followed by silver staining and/or Western blotting.

Construction, Expression, and Purification of CRACC-ECD/mIgG1-Fc Fusion Protein

A fusion protein comprising the murine CRACC ECD fused in frame with a murine IgG1-Fc constant region was constructed using standard molecular biology techniques. The amino acid sequence for the fusion protein is as follows:

(SEQ ID NO: 173)
MYRMQLLSCIALSLALVTNSSGTLKKVAGALDGSVTFTLNITEIKVD

YVVWTFNTFFLAMVKKDGVTSQSSNKERIVFPDGLYSMKLSQLKKND

SGAYRAEIYSTSSQASLIQEYVLHVYKHLSRPKVTIDRQSNKNGTCV

INLTCSTDQDGENVTYSWKAVGQGDNQFHDGATLSIAWRSGEKDQAL

TCMARNPVSNSFSTPVFPQKLCEDAATDLTSLRGGCKPCICTVPEVS

SVFIFPPKPKDVLTITLTPKVTCVVVDISKDDPEVQFSWFVDDVEVH

TAQTQPREEQFNSTFRSVSELPIMHQDWLNGKEFKCRVNSAAFPAPI

EKTISKTKGRPKAPQVYTIPPPKEQMAKDKVSLTCMITDFFPEDITV

EWQWNGQPAENYKNTQPIMDTDGSYFVYSKLNVQKSNWEAGNTFTCS

VLHEGLHNHHTEKSLSHSPGK.

Figure 2:
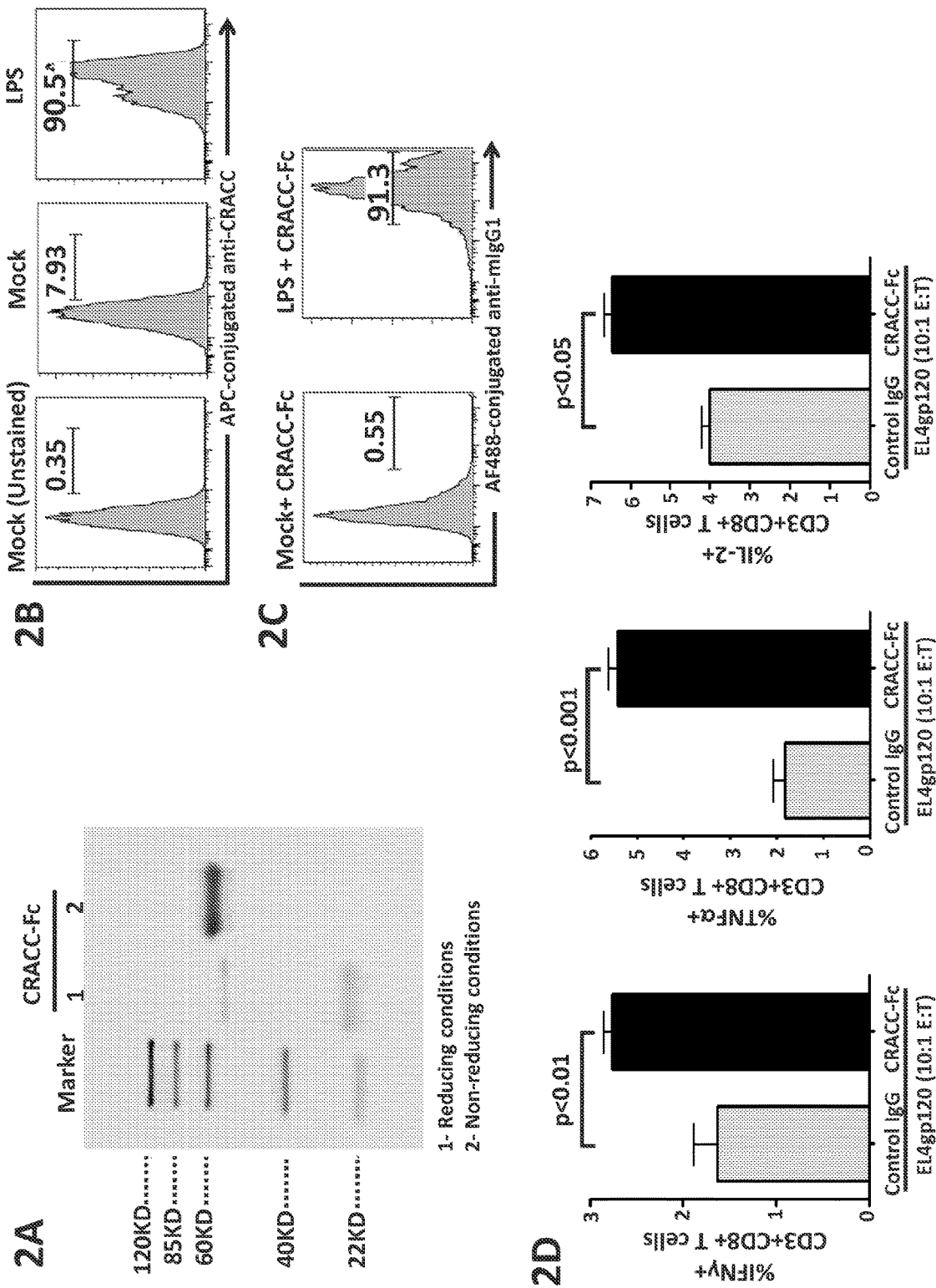
FIG. 2A is a photograph of a western blot depicting purified mouse CRACC-ECD/mIgG1-Fc fusion protein (see working examples). The molecular weight in kD is indicated at the left of the photograph. The isolated protein was subjected to SDS-PAGE under reducing (1) and non-reducing (2) conditions.
FIG. 2B is series of flow cytometry histograms depicting the level of expression of CRACC by RAW264.7 cells. Cells, either stimulated with lipoprotein polysaccharide (LPS) or mock stimulated, were contacted with APC-conjugated anti-CRACC antibody. Cells not contacted with the APC-conjugated antibody are shown in the left histogram. The percentage of cells staining positive for CRACC is shown in each histogram.
FIG. 2C is a pair of histograms depicting the binding of a murine CRACC-ECD/mIgG1-Fc fusion protein to RAW264.7 cells. Cells, either stimulated with lipoprotein polysaccharide (LPS) or mock stimulated, were contacted with the fusion protein and an ALEXA FLUOR®-488-conjugated anti-mouse IgG1 antibody. The percentage of cells staining positive for the fusion protein is shown in each histogram.
FIG. 2D is a series of bar graphs depicting the effect of a murine CRACC-ECD/mIgG1-Fc fusion protein on antigen-dependent cytokine production. The percentage of gp120-specific $CD8^+$ T cells staining positive for IFNγ, TNFα, and IL-2, as compared to IgG treated controls, is shown in each histogram.

Briefly, human embryonic kidney HEK293-6E cells were grown in serum-free FreeStyle™ 293 expression medium (Invitrogen, Carlsbad, Calif.). The cells were maintained in Erlenmeyer Flasks (Corning Inc., Acton, Mass.) at 37° C. with 5% $CO_2$ on an orbital shaker (VWR Scientific, Chester, Pennsylvania). The cells were seeded in the flasks one day before transfection. On the day of transfection, an expression vector [which expression vector] encoding the CRACC-Fc protein and polyethylenimine (PEI; Polysciences, Eppelheim, Germany) were mixed and then added into the media in which the cells were cultured. The supernatant was collected on day six (6) and, from the supernatant, the fusion protein was purified. The supernatant was centrifuged, followed by microfiltration using a 5 mL HITRAP™ MABSELECT column (GE Healthcare, Uppsala, Sweden) at a flow rate of 1.0 mL/minute. After washing the column, fractions were eluted and then subsequently neutralized using 1M Tris-HCl, pH 9.0. The purified protein was analyzed by SDS-PAGE and Western blot (FIG. 2A) using a goat anti-CRACC antibody (Genscript™, Piscataway, N.J.; catalogue number: A00166). The CRACC-Fc fusion protein had an observed molecular weight of approximately 55 kDa (FIG. 2A).

Animal Procedures

Figure 9:
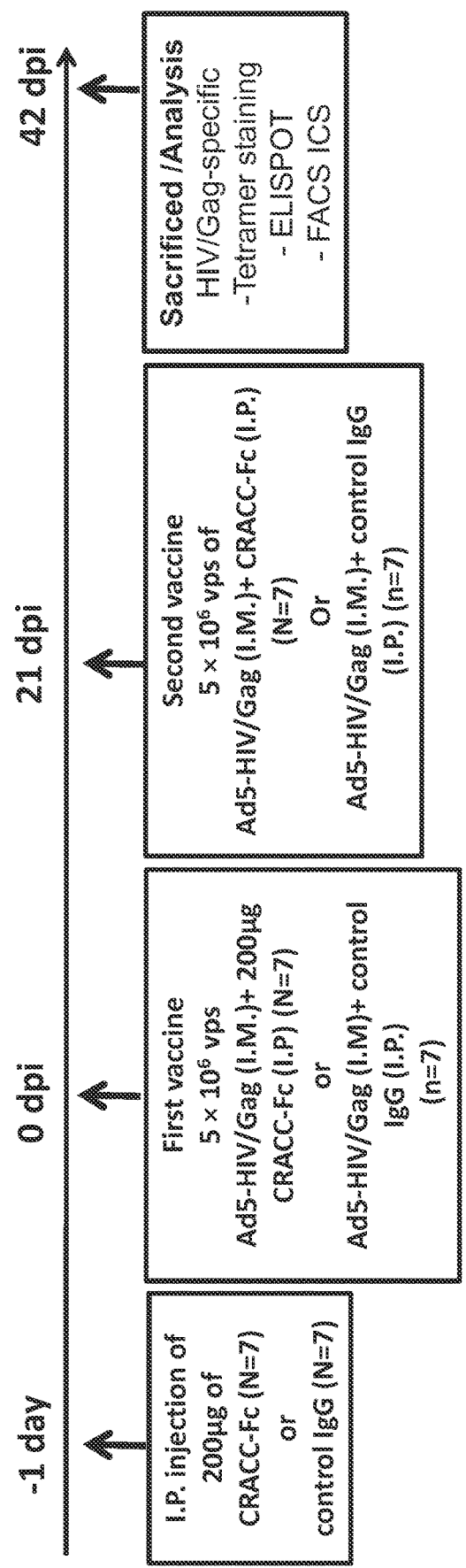
FIG. 9 depicts a vaccination scheme for mice.

All animal procedures were approved by the Michigan State University Institutional Animal Care and Use Committee (IACUC). Care for mice was provided in accordance with U.S. Public Health Service (PHS) and Association for Assessment and Accreditation of Laboratory Animal Care International (AAALAC) standards. Adult male wild type (WT) BALB/cj and C57BL/6 mice were purchased from Taconic™ (Hudson, N.Y.). For innate immune cell responses, C57BL/6 mice (6-8 weeks old) were injected intramuscularly (i.m.; into the tibialis anterior of the right hindlimb) with 25 µl of a phosphate-buffered saline solution (PBS, pH 7. 4), containing $2 \times 10^{10}$ total virus particles of rAd5-Null. Concurrent with rAd5-Null injection, mice were intraperitoneally (i.p.) injected with 200 µg (prepared in 150 µl of sterile PBS) of either the CRACC-Fc fusion protein or the control rat IgG (Sigma, St. Louis, Mo.) antibody as described in Butler et al. (2012) *Nat Immunol* 13:188-195. For Gag-specific adaptive immune response studies, BALB/cj mice received i.p. injections of 200 µg of CRACC-Fc or control rat IgG. Approximately 24 hours after the initial injection, rAd5-HIV/Gag ($5 \times 10^6$ total viral particles (vps)) was i.m. injected into the mice along with a second dose of 200 µg of CRACC-Fc or control rat IgG. Twenty one days after the initial i.m. injection with virus, the mice received an additional 200 µg dose of CRACC-Fc or control rat IgG, concurrently with yet another i.m. injection of virus (as above) (FIG. 9). The mice were sacrificed at 42 days after the initial infection.

Isolation of Splenocytes

Splenocytes from individual mice were harvested and processed as follows: spleen tissues were physically disrupted (by passage through a 40 um sieve), followed by lysis of red blood cells (RBCs) using 2 ml of ACK Lysing Buffer (Invitrogen, Carlsbad, Calif.) per homogenized spleen. Splenocytes were subsequently washed two times with RPMI medium 1640 (Invitrogen) supplemented with 10% fetal bovine serum (FBS), 2 mM L-glutamine, and 1% PSF (penicillin, streptomycin, and fungizone) solution, then resuspended and counted.

Cell Culture

Bone marrow cells were extracted from the femurs and tibias of male 8-12 week old BALB/cj mice and rinsed with ACK lysis buffer to remove RBCs. Bone marrow cells were cultured in Dulbecco modified Eagle medium (DMEM) supplemented with 10% FBS and 30% supernatant derived from confluent L929 cell cultures. At day 7, immature macrophages were collected and plated into 12-well plates for 24 hours. This procedure yields a pure population of macrophage colony-stimulating, factor-dependent, adherent macrophages. Murine RAW264.7 macrophages (ATCC TIB71) were maintained in DMEM supplemented with 10% FBS, penicillin, and streptomycin. Suspensions of $3 \times 10^5$ cells were seeded into each well of 12-well plates. The cells were then incubated with 600 µl culture medium alone, or with medium containing rAd5-EAT2 or controls at 20,000 multiplicity of infection (MOI) for 72 hours. For CRACC receptor induction, RAW264.7 cells were stimulated with LPS (1 µg/ml) for 24 hours and CRACC expression was evaluated using the APC-conjugated CRACC antibody (R&D Systems, Minneapolis, Minn.; catalogue number: FAB4628A). To confirm the specificity of the CRACC-Fc interaction with CRACC, LPS stimulated RAW264.7 cells were pre-incubated with 10 µl of CRACC-Fc (5 µg/ml) fusion protein and then stained with an ALEXA FLUOR® 488-conjugated anti-mouse IgG1 antibody.

Quantitative RT-PCR

To determine relative levels of SLAM receptors, $3 \times 10^5$ RAW264.7 cells were mock infected or infected with rAd5-EAT2 virus or control virus at the indicated time points and RNA was harvested using TRIzol® reagent (Invitrogen) as described in the manufacturer's protocol. Following RNA isolation, reverse transcription was performed on 0.2-1.0 µg of total RNA using SuperScript® III (Invitrogen) reverse transcriptase (RT) kit. RT reactions were diluted to a total volume of 60 and 2 µl per sample was used as the template in the subsequent PCR reactions. Primers were designed using Primer Bank web-based software (as described in Spandidos et al. (2010) *Nucleic Acids Res* 38:D792-799). A pair of Forward (For) and Reverse (Rev) primers is provided for every transcript tested by qRT-PCR based methods. The length of resulted PCR products produced using the primer pairs was 100-160 nucleotides. The primers that were used are listed in Table 1 below.

TABLE 1

| Genes | Primers used for qRTPCR | SEQ ID NO: |
|---|---|---|
| ADAR | ADAR-Mm-For 5'-AGGA TTGGTGAGCTCGTCAG | SIN: 13 |
|  | ADAR-Mm-Rev 5'-GCCCT GTTTCTTGCTGTGTG | SIN: 14 |
| GAPDH | GAPDH-Mm-For 5'-AGAA CATCATCCCTGCATCC | SIN: 15 |
|  | GAPDH-Mm-Rev 5'-CACA TTGGGGGTAGGAACAC | SIN: 16 |
| ICAM-1 | ICAM1-Mm-For 5'-GGCA TTGTTCTCTAATGTCTCCG | SIN: 17 |
|  | ICAM1-Mm-Rev 5'-GCTC CAGGTATATCCGAGCTTC | SIN: 18 |
| NOD-1 | NOD1-Mm-For 5'-CCCCT TCCCAGCTCATTCG | SIN: 19 |
|  | NOD1-Mm-Rev 5'-TGTGT CCATATAGGTCTCCTCCA | SIN: 20 |
| TNFa | TNFα-Mm-For 5'-CCCTC ACACTCAGATCATCTTCT | SIN: 21 |
|  | TNFα-Mm-Rev 5'-GCTAC GACGTGGGCTACAG | SIN: 22 |
| IL-6 | IL6-Mm-For 5'-TAGTCC TTCCTACCCCAATTTCC | SIN: 23 |
|  | IL6-Mm-Rev 5'-TTGGTC CTTAGCCACTCCTTC | SIN: 24 |
| IL-15 | IL15-Mm-For 5'-TCTCC CTAAAACAGAGGCCAA | SIN: 25 |
|  | IL15-Mm-Rev 5'-TGCAA CTGGGATGAAAGTCAC | SIN: 26 |
| EAT-2 | EAT-2-Mm-For 5'-CTGG GACTGATCTCAGGGTG | SIN: 27 |
|  | EAT-2-Mm-Rev 5'-GAAG GGAACGGGAGAATGGG | SIN: 28 |
| CRACC | CRACC-Mm-For 5'-CCGA CTTGTGCCCTCACTTAG | SIN: 29 |
|  | CRACC-Mm-Rev 5'-GAGC TGGGACTCTTTACCACT | SIN: 30 |

TABLE 1-continued

| Genes | Primers used for qRTPCR | SEQ ID NO: |
|---|---|---|
| 2B4 | 2B4-Mm-For 5'-CTCGGG GCCATCATTTGTTTC | SIN: 31 |
|  | 2B4-Mm-Rev 5'-GCTAGA AGGGAGCTGAACATCA | SIN: 32 |
| SLAM | SLAM-Mm-For 5'-AAATC AGGGGTACGTTCTATGCC | SIN: 33 |
|  | SLAM-Mm-Rev 5'-TCCTG TGCGAAATATGACAGAC | SIN: 34 |
| Ly108 | LY108-Mm-For 5'-TCTC CAGGGAACACTGTGTATG | SIN: 35 |
|  | LY108-Mm-Rev 5'-GGTT GGTTATAGCCGGTTAAAGC | SIN: 36 |
| Ly9 | LY9-Mm-For 5'-TCAGGG ATGCTAGGGGGTTC | SIN: 37 |
|  | LY9-Mm-Rev 5'-TTCGCT GACTTTGAGTCTGCC | SIN: 38 |
| CD84 | CD84-Mm-For 5'-TTATT CTCATTCCGATGTTGGCA | SIN: 39 |
|  | CD84-Mm-Rev 5'-GTGGG TTGAGCATTTCTTGAAAC | SIN: 40 |

Quantitative PCR (qPCR) was carried out on an ABI 7900HT Fast Real-Time PCR System using SYBR® Green PCR Mastermix (Applied Biosystems) in a 15 µl reaction. Thermocycling of the PCR reactions was performed as follows: 95.0 C.° for 10 minutes followed by 40 cycles of 95.0 C.° for 15 seconds followed by 60.0 C.° for 1 minute. The comparative $C_t$ method (see, e.g., Schmittgen and Livak (2008) *Nature Protocols* 3:1101-1108) was used to determine relative gene expression using GAPDH to standardize expression levels across all samples. Relative expression changes were calculated based on comparing experimental levels of a respective transcript to those quantified in samples derived from mock injected animals.

ELISPOT Analysis

Splenocytes were harvested from individual mice and RBCs were lysed using ACK lysis buffer (Invitrogen). 96-well Multiscreen high protein binding ImmobilonTMP membrane plates (Millipore, Billerica, Mass.) were pre-treated with ethanol, coated with mouse anti-IFNγ capture antibody, incubated overnight, and blocked prior to the addition of $5 \times 10^5$ splenocytes/well. Ex vivo stimulation included the incubation of splenocytes in 100 µL of media alone (unstimulated) or media containing 2 µg/ml of Gag specific peptide (Gag-AMQMLKETI (SEQ ID NO:11) constructed by Genscript, Piscataway, N.J.) or a pool of peptides spanning the entire Gag protein (obtained from QBI (Gaithersburg, Md.) through the Vaccine Research and Development Branch, Division of AIDS, National Institute of Allergy and Infectious Diseases, National Institutes of Health (NIAID, NIH)). The amino acid sequences for these peptides are set forth in Table 2 below.

TABLE 2

| Peptide Name and Sequence | SEQ ID NO. |
|---|---|
| HIV-1 M con gag peptide (15-mer) MGARASVLSGGKLDA | 41 |
| HIV-1 M con gag peptide (15-mer) ASVLSGGKLDAWEKI | 42 |
| HIV-1 M con gag peptide (15-mer) SGGKLDAWEKIRLRP | 43 |
| HIV-1 M con gag peptide (15-mer) LDAWEKIRLRPGGKK | 44 |
| HIV-1 M con gag peptide (15-mer) EKIRLRPGGKKKYRL | 45 |
| HIV-1 M con gag peptide (15-mer) LRPGGKKKYRLKHLV | 46 |
| HIV-1 M con gag peptide (15-mer) GKKKYRLKHLVWASR | 47 |
| HIV-1 M con gag peptide (15-mer) YRLKHLVWASRELER | 48 |
| HIV-1 M con gag peptide (15-mer) HLVWASRELERFALN | 49 |
| HIV-1 M con gag peptide (15-mer) ASRELERFALNPGLL | 50 |
| HIV-1 M con gag peptide (14-mer) LERFALNPGLLETS | 51 |
| HIV-1 M con gag peptide (15-mer) FALNPGLLETSEGCK | 52 |
| HIV-1 M con gag peptide (15-mer) PGLLETSEGCKQIIG | 53 |
| HIV-1 M con gag peptide (15-mer) ETSEGCKQIIGQLQP | 54 |
| HIV-1 M con gag peptide (15-mer) GCKQIIGQLQPALQT | 55 |
| HIV-1 M con gag peptide (13-mer) IIGQLQPALQTGS | 56 |
| HIV-1 M con gag peptide (15-mer) GQLQPALQTGSEELR | 57 |
| HIV-1 M con gag peptide (15-mer) PALQTGSEELRSLYN | 58 |
| HIV-1 M con gag peptide (15-mer) TGSEELRSLYNTVAT | 59 |
| HIV-1 M con gag peptide (15-mer) ELRSLYNTVATLYCV | 60 |
| HIV-1 M con gag peptide (15-mer) LYNTVATLYCVHQRI | 61 |
| HIV-1 M con gag peptide (14-mer) VATLYCVHQRIEVK | 62 |
| HIV-1 M con gag peptide (14-mer) LYCVHQRIEVKDTK | 63 |
| HIV-1 M con gag peptide (14-mer) VHQRIEVKDTKEAL | 64 |
| HIV-1 M con gag peptide (14-mer) RIEVKDTKEALEKI | 65 |
| HIV-1 M con gag peptide (15-mer) VKDTKEALEKIEEEQ | 66 |
| HIV-1 M con gag peptide (15-mer) KEALEKIEEEQNKSQ | 67 |

TABLE 2-continued

| Peptide Name and Sequence | SEQ ID NO. |
|---|---|
| HIV-1 M con gag peptide (15-mer) EKIEEEQNKSQQKTQ | 68 |
| HIV-1 M con gag peptide (15-mer) EEQNKSQQKTQQAAA | 69 |
| HIV-1 M con gag peptide (15-mer) KSQQKTQQAAADKGN | 70 |
| HIV-1 M con gag peptide (15-mer) KTQQAAADKGNSSKV | 71 |
| HIV-1 M con gag peptide (15-mer) AAADKGNSSKVSQNY | 72 |
| HIV-1 M con gag peptide (15-mer) KGNSSKVSQNYPIVQ | 73 |
| HIV-1 M con gag peptide (15-mer) SKVSQNYPIVQNLQG | 74 |
| HIV-1 M con gag peptide (15-mer) SQNYPIVQNLQGQMV | 75 |
| HIV-1 M con gag peptide (15-mer) PIVQNLQGQMVHQAI | 76 |
| HIV-1 M con gag peptide (15-mer) NLQGQMVHQAISPRT | 77 |
| HIV-1 M con gag peptide (15-mer) GQMVHQAISPRTLNA | 78 |
| HIV-1 M con gag peptide (15-mer) HQAISPRTLNAWVKV | 79 |
| HIV-1 M con gag peptide (15-mer) SPRTLNAWVKVIEEK | 80 |
| HIV-1 M con gag peptide (15-mer) LNAWVKVIEEKAFSP | 81 |
| HIV-1 M con gag peptide (15-mer) VKVIEEKAFSPEVIP | 82 |
| HIV-1 M con gag peptide (15-mer) EEKAFSPEVIPMFSA | 83 |
| HIV-1 M con gag peptide (15-mer) FSPEVIPMFSALSEG | 84 |
| HIV-1 M con gag peptide (15-mer) VIPMFSALSEGATPQ | 85 |
| HIV-1 M con gag peptide (15-mer) FSALSEGATPQDLNT | 86 |
| HIV-1 M con gag peptide (15-mer) SEGATPQDLNTMLNT | 87 |
| HIV-1 M con gag peptide (15-mer) TPQDLNTMLNTVGGH | 88 |
| HIV-1 M con gag peptide (15-mer) LNTMLNTVGGHQAAM | 89 |
| HIV-1 M con gag peptide (15-mer) LNTVGGHQAAMQMLK | 90 |
| HIV-1 M con gag peptide (15-mer) GGHQAAMQMLKDTIN | 91 |
| HIV-1 M con gag peptide (15-mer) AAMQMLKDTINEEAA | 92 |
| HIV-1 M con gag peptide (15-mer) MLKDTINEEAAEWDR | 93 |
| HIV-1 M con gag peptide (15-mer) TINEEAAEWDRLHPV | 94 |
| HIV-1 M con gag peptide (15-mer) EAAEWDRLHPVHAGP | 95 |
| HIV-1 M con gag peptide (15-mer) WDRLHPVHAGPIPPG | 96 |
| HIV-1 M con gag peptide (14-mer) HPVHAGPIPPGQMR | 97 |
| HIV-1 M con gag peptide (15-mer) HAGPIPPGQMREPRG | 98 |
| HIV-1 M con gag peptide (15-mer) IPPGQMREPRGSDIA | 99 |
| HIV-1 M con gag peptide (15-mer) GQMREPRGSDIAGTT | 100 |
| HIV-1 M con gag peptide (15-mer) EPRGSDIAGTTSTLQ | 101 |
| HIV-1 M con gag peptide (15-mer) SDIAGTTSTLQEQIA | 102 |
| HIV-1 M con gag peptide (15-mer) GTTSTLQEQIAWMTS | 103 |
| HIV-1 M con gag peptide (15-mer) TLQEQIAWMTSNPPI | 104 |
| HIV-1 M con gag peptide (15-mer) EQIAWMTSNPPIPVG | 105 |
| HIV-1 M con gag peptide (15-mer) WMTSNPPIPVGEIYK | 106 |
| HIV-1 M con gag peptide (15-mer) NPPIPVGEIYKRWII | 107 |
| HIV-1 M con gag peptide (15-mer) PVGEIYKRWIILGLN | 108 |
| HIV-1 M con gag peptide (15-mer) IYKRWIILGLNKIVR | 109 |
| HIV-1 M con gag peptide (15-mer) WIILGLNKIVRMYSP | 110 |
| HIV-1 M con gag peptide (15-mer) GLNKIVRMYSPVSIL | 111 |
| HIV-1 M con gag peptide (15-mer) IVRMYSPVSILDIRQ | 112 |
| HIV-1 M con gag peptide (14-mer) YSPVSILDIRQGPK | 113 |
| HIV-1 M con gag peptide (15-mer) VSILDIRQGPKEPFR | 114 |
| HIV-1 M con gag peptide (14-mer) DIRQGPKEPFRDYV | 115 |
| HIV-1 M con gag peptide (15-mer) RQGPKEPFRDYVDRF | 116 |
| HIV-1 M con gag peptide (15-mer) KEPFRDYVDRFFKTL | 117 |

TABLE 2-continued

| Peptide Name and Sequence | SEQ ID NO. |
|---|---|
| HIV-1 M con gag peptide (15-mer) RDYVDRFFKTLRAEQ | 118 |
| HIV-1 M con gag peptide (14-mer) DRFFKTLRAEQATQ | 119 |
| HIV-1 M con gag peptide (15-mer) FKTLRAEQATQDVKN | 120 |
| HIV-1 M con gag peptide (14-mer) RAEQATQDVKNWMT | 121 |
| HIV-1 M con gag peptide (15-mer) EQATQDVKNWMTDTL | 122 |
| HIV-1 M con gag peptide (15-mer) TQDVKNWMTDTLLVQ | 123 |
| HIV-1 M con gag peptide (15-mer) KNWMTDTLLVQNANP | 124 |
| HIV-1 M con gag peptide (15-mer) TDTLLVQNANPDCKT | 125 |
| HIV-1 M con gag peptide (15-mer) LVQNANPDCKTILKA | 126 |
| HIV-1 M con gag peptide (15-mer) ANPDCKTILKALGPG | 127 |
| HIV-1 M con gag peptide (14-mer) CKTILKALGPGATL | 128 |
| HIV-1 M con gag peptide (15-mer) ILKALGPGATLEEMM | 129 |
| HIV-1 M con gag peptide (15-mer) LGPGATLEEMMTACQ | 130 |
| HIV-1 M con gag peptide (15-mer) ATLEEMMTACQGVGG | 131 |
| HIV-1 M con gag peptide (15-mer) EMMTACQGVGGPGHK | 132 |
| HIV-1 M con gag peptide (15-mer) ACQGVGGPGHKARVL | 133 |
| HIV-1 M con gag peptide (15-mer) VGGPGHKARVLAEAM | 134 |
| HIV-1 M con gag peptide (15-mer) GHKARVLAEAMSQVT | 135 |
| HIV-1 M con gag peptide (15-mer) RVLAEAMSQVTNAAI | 136 |
| HIV-1 M con gag peptide (15-mer) EAMSQVTNAAIMMQR | 137 |
| HIV-1 M con gag peptide (15-mer) SQVTNAAIMMQRGNF | 138 |
| HIV-1 M con gag peptide (15-mer) NAAIMMQRGNFKGQR | 139 |
| HIV-1 M con gag peptide (15-mer) MMQRGNFKGQRRIIK | 140 |
| HIV-1 M con gag peptide (14-mer) GNFKGQRRIIKCFN | 141 |
| HIV-1 M con gag peptide (14-mer) KGQRRIIKCFNCGK | 142 |
| HIV-1 M con gag peptide (15-mer) RRIIKCFNCGKEGHI | 143 |
| HIV-1 M con gag peptide (14-mer) KCFNCGKEGHIARN | 144 |
| HIV-1 M con gag peptide (15-mer) NCGKEGHIARNCRAP | 145 |
| HIV-1 M con gag peptide (15-mer) EGHIARNCRAPRKKG | 146 |
| HIV-1 M con gag peptide (14-mer) ARNCRAPRKKGCWK | 147 |
| HIV-1 M con gag peptide (14-mer) CRAPRKKGCWKCGK | 148 |
| HIV-1 M con gag peptide (15-mer) PRKKGCWKCGKEGHQ | 149 |
| HIV-1 M con gag peptide (13-mer) GCWKCGKEGHQMK | 150 |
| HIV-1 M con gag peptide (14-mer) WKCGKEGHQMKDCT | 151 |
| HIV-1 M con gag peptide (15-mer) GKEGHQMKDCTERQA | 152 |
| HIV-1 M con gag peptide (15-mer) HQMKDCTERQANFLG | 153 |
| HIV-1 M con gag peptide (15-mer) DCTERQANFLGKIWP | 154 |
| HIV-1 M con gag peptide (15-mer) RQANFLGKIWPSNKG | 155 |
| HIV-1 M con gag peptide (15-mer) FLGKIWPSNKGRPGN | 156 |
| HIV-1 M con gag peptide (15-mer) IWPSNKGRPGNFLQS | 157 |
| HIV-1 M con gag peptide (15-mer) NKGRPGNFLQSRPEP | 158 |
| HIV-1 M con gag peptide (15-mer) PGNFLQSRPEPTAPP | 159 |
| HIV-1 M con gag peptide (15-mer) LQSRPEPTAPPAESF | 160 |
| HIV-1 M con gag peptide (14-mer) PEPTAPPAESFGFG | 161 |
| HIV-1 M con gag peptide (15-mer) TAPPAESFGFGEEIT | 162 |
| HIV-1 M con gag peptide (15-mer) AESFGFGEEITPSPK | 163 |
| HIV-1 M con gag peptide (15-mer) GFGEEITPSPKQEPK | 164 |
| HIV-1 M con gag peptide (15-mer) EITPSPKQEPKDKEP | 165 |
| HIV-1 M con gag peptide (15-mer) SPKQEPKDKEPPLTS | 166 |
| HIV-1 M con gag peptide (15-mer) EPKDKEPPLTSLKSL | 167 |

TABLE 2-continued

| Peptide Name and Sequence | SEQ ID NO. |
|---|---|
| HIV-1 M con gag peptide (14-mer) KEPPLTSLKSLFGN | 168 |
| HIV-1 M con gag peptide (16-mer) PLTSLKSLFGNDPLS | 169 |

Plates were then incubated for 24 hours at 37° C. and 5% $CO_2$. Staining of plates was completed per the manufacturer's protocol. Spots were counted and photographed by an automated ELISPOT reader system (Cellular Technology, Cleveland, Ohio). Detection of mouse interferon gamma was performed using the Mouse IFN gamma Ready-set Go!® ELISpot kit (eBioscience, San Diego, Calif.).

Cell Staining and Flow Cytometry

To evaluate the intracellular cytokine responses following rAd5-Gag virus and CRACC-Fc co-vaccination, cells were either unstimulated or stimulated for 6 hours with Gag immunodominant peptides in the presence of the protein transport inhibitor, BD Golgi Plug™ (BD Biosciences, San Diego, Calif.). Intracellular staining was then performed as previously described (Aldhamen et al. (2011), supra; Aldhamen et al. (2012), supra). Briefly, cells were surface stained with APC-Cy7-CD3, ALEXA FLUOR® 700-CD8a, and CD16/32 Fc-block antibodies, fixed with 2% formaldehyde (Polysciences, Warrington, Pa.), permeabilized with 0.2% saponin (Sigma-Aldrich, St. Louis, Mo.), and stained for intracellular cytokines with PE-Cy7-TNFα, APC-Granzyme B, PE-Perforin, FITC-IFNγ (2 µg/ml) (all obtained from BD Biosciences, San Diego, Calif.), and PerCp-Cy5.5-IL2 (BioLegend, San Diego, Calif.). We included the violet fluorescent reactive dye (ViViD, Invitrogen) as a viability marker to exclude dead cells from the analysis (see Perfetto et al. (2006) J Immunol Methods 313:199-208). For innate immune cell activation studies, splenocytes were stained with various combinations of the following antibodies: PE-CD69, (2 µg/ml), APC-CD3, ALEXA FLUOR® 700-CD8a, PE-Cy7-NK1.1, CD11c-PE-Cy7, and CD11b-APC-Cy7 (2 µg/ml) (all obtained from BD Biosciences). Cells were incubated on ice with the appropriate antibodies for 30 minutes, washed, and data were collected using an LSR II instrument and analyzed using FlowJo software. For tetramer staining, blood was isolated by retro-orbital bleeds and PBMCs were isolated using Lympholyte-Mammal (Cedarlane, Burlington, N.C.). Tetramer staining was completed using a PE conjugated MHC-I tetramer folded with the AMQMLKETI (SEQ ID NO:11) peptide generated at the NIH Tetramer Core Facility.

Elicitation of Splenocytes with DC2.4$_{gp120}$ Cells

The in vitro induction of CTLs by CRACC-Fc was performed, exactly as previously described (Chen et al. (2012) J Leukoc Biol 92:1093-1102). Briefly, DC2.4$_{gp120}$ cells were X-ray irradiated (35 gray) to prevent proliferation, washed three times, and adjusted to 1×10$^6$ cells/ml. Splenocytes (1×10$^7$ cells/me were treated with CRACC-Fc or control IgG antibody (5, 10, and 20 µg) for 30 mM and then co-cultured with DC2.4$_{gp120}$ cells (100 µl each cell type in 96 U-bottom plates) for 5 days of elicitation in 5% FBS CTL media (RPMI plus 5% BCS, Pen/Strep, 2 mM MEM NEAA, 2 mM sodium pyruvate, 2 mM L-glutamine, and 50 µM 2-mercaptoethanol (2-ME)), supplemented with 5 ng/ml mouse rIL-12 were used (R&D Systems, Minneapolis, Minn., USA). In the effector phase, 1 ng/ml mouse rIL-12 was substituted in the CTL media. After 5 days of co-culture, elicited effector splenocytes (2×10$^7$ cells/ml) were re-stimulated with EL4$_{gp120}$ or parental EL4 target cells (1×10$^6$ cells/ml) in 2% FBS CTL media. Effectors and targets (50µl each) were plated in 96-well plate overnight. A CTL-only group (no target restimulation) was included as a control to assess background, nonspecific CTL activity. BD Golgi Plug™ (BD Biosciences) was added at the last 4 hours. FACS ICS analysis was performed as described in Aldhamen et al. (2013) Cancer Gene Ther 20:564-575.

Statistical Analysis

Statistically significant differences in toxicities associated with innate immune responses were determined using One Way ANOVA with a Student-Newman-Keuls post-hoc test (p value <0. 05, deemed statistically significant). For ELISPOT analysis, a two way ANOVA was used followed by Bonferroni post hoc test. For flow cytometry, a One Way ANOVA with a Student-Newman-Keuls post-hoc test was used. For in vitro CTL assay, a One Way ANOVA with a Student-Newman-Keuls post-hoc test was used. Statistical analyses were performed using GraphPad Prism® (GraphPad Software, Inc.).

Example 2. EAT-2 Overexpression Inhibits Ad5-Mediated Induction of the SLAM Family Member CRACC A series of experiments using a transformed mouse macrophage cell line RAW264.7 were performed to study the effects of EAT-2 overexpression on SLAM family member proteins. RAW264.7 cells were mock infected or infected with rAd5-EAT2 virus or a control rAd5-Null virus and the expression levels of SLAM family members: SLAM, 2B4, CRACC, CD84, and Ly-9 were analyzed by quantitative RT-PCR, six hours post-infection (hpi) with the viruses. The expression of the additional SLAM family member Ly108 was not detectable in these cells; a result that is consistent with previously published studies (Zhong and Veillette (2008) J Biol Chem 283:19255-19264. Infection of these cells with adenovirus alone significantly (p<0.001) induced the expression of the SLAM family member CRACC, but not other members of the SLAM family (FIG. 1A). In contrast, infection of these cells with rAd5-EAT2 virus significantly reduced the induction of CRACC gene expression (p<0.001) observed with rAd5-Null virus (FIG. 1A).

At 3 hpi, the expression level of CRACC by the RAW267.4 cells was significantly and equivalently induced (p<0.01) by both the rAd5-EAT2 virus and rAd5-Null virus (FIG. 1B). However, at later time points (e.g., 6, 15, and 24 hpi), when EAT-2 protein levels are increased following infection with the virus (Aldhamen et al. (2004) Int Immunol 26:291-303), infection with the rAd5-Null adenovirus continued to significantly (p<0.001) induce CRACC expression, whereas infection associated with EAT-2 overexpression (by way of the rAd5-EAT2 virus) significantly (p<0.001) reduced CRACC expression at these same time points (FIG. 1B). To confirm the specificity of CRACC modulation by EAT-2, the expression level of several other innate immune genes 15 hours following rAd5-EAT2 infection was measured. Both rAd5-EAT2 and rAd5-Null viruses induced similar expression levels of multiple genes (e.g. ADAR, ICAM-1, NOD-1, TNF-α, IL-6, and IL-15) (FIG. 1C). EAT-2 transcript levels were also measured at the time points tested. Minimal induction of EAT-2 (two fold over mock) was observed following rAd5-Null virus infection, suggesting minor activation of SLAM signaling pathways following adenoviral infection. In contrast, significant increases (over 100 fold) in EAT-2 transcript were detected in rAd5-EAT2 transduced cells; due to high level EAT-2 gene expression from the rAd5-EAT2 virus. While the disclosure is not limited by any particular theory or mechanism of action, taken together these results suggest that EAT-2 overexpression specifically represses the SLAM family member CRACC, following adenoviral infection of RAW264.7 macrophages.

Example 3. Blocking CRACC-CRACC Homophilic Interactions Enhances the Functionality of Antigen-Specific CD8+ T Cells In Vitro To determine the significance of CRACC receptor down-modulation following EAT-2 overexpression, the impact of inhibiting the homophilic interaction of CRACC on CD8+ T cells responses was evaluated. To prevent CRACC-CRACC interactions, a CRACC extracellular domain (ECD)-targeting Fc fusion protein was constructed (see above). Plasmid encoding CRACC-ECD/mIgG1-Fc was transiently transfected into 100 mL suspension HEK 293-6E cell culture. CRACC-Fc protein was captured from the cell culture supernatant by HITRAP™ MABSELECT 5 mL column and followed by buffer exchange. Western blot analysis was used to confirm that the fusion protein of the ~55 kDa protein was expressed and secreted from 293 cells, and purified to homogeneity (FIG. 2A).

To investigate if CRACC-Fc protein can specifically bind to CRACC receptor, FACS analysis of LPS-treated RAW264.7 cells was performed. Briefly, RAW264.7 cells (300,000 cells/well) were mock treated or treated with LPS (1 μg/ml). After 24 hours, cells were harvested stained with APC-conjugated CRACC antibody. CRACC expression was evaluated by flow cytometry (FIG. 2B). To determine if the CRACC-Fc fusion protein bound to CRACC expressed by cells, LPS-treated RAW264.7 cells were pre-incubated for one hour with 4 μg of CRACC-Fc protein. After 1 hour, cells were washed and stained with ALEXA FLUOR® 488-conjugated anti-mouse IgG1 antibody. As shown in FIG. 2C, CRACC-Fc fusion protein can specifically bind to CRACC receptor.

To demonstrate the impact of CRACC-CRACC interaction during antigen presentation on the elicited antigen-specific CD8+ T cell response, the following experiments were performed using the DC2.4gp120 in vitro CTL system as described in Chen et al. (2012) *J Leukoc Biol* 92:1093-1102. For these studies, splenocytes derived from C57BL/6 mice were co-cultured for five days with the DC2.4gp120 cells in the presence of 10 μg/ml of CRACC-Fc or a control IgG antibody. After 5 days, cells were re-stimulated with gp120 expressing EL-4 cells at a ratio of 1:4 (EL4:RAW). Golgi Plug™ was added to the cells 4 hours prior to FACS analysis to identify IFNγ-, TNFα-, and IL-2-expressing CD8+ T cells. Addition of CRACC-Fc resulted in significant increases in the number of IFNγ ($p<0.01$), TNFα ($p<0.001$), and IL-2 ($p<0.05$) expressing, gp120-specific CD8+ T cells, as compared to IgG treated controls (FIG. 2D). These data suggest that blocking CRACC-CRACC interaction during the initial stage of CD8+ T cell memory response, improves the magnitude of the elicited antigen-specific CD8+ T cell response.

Figure 3:
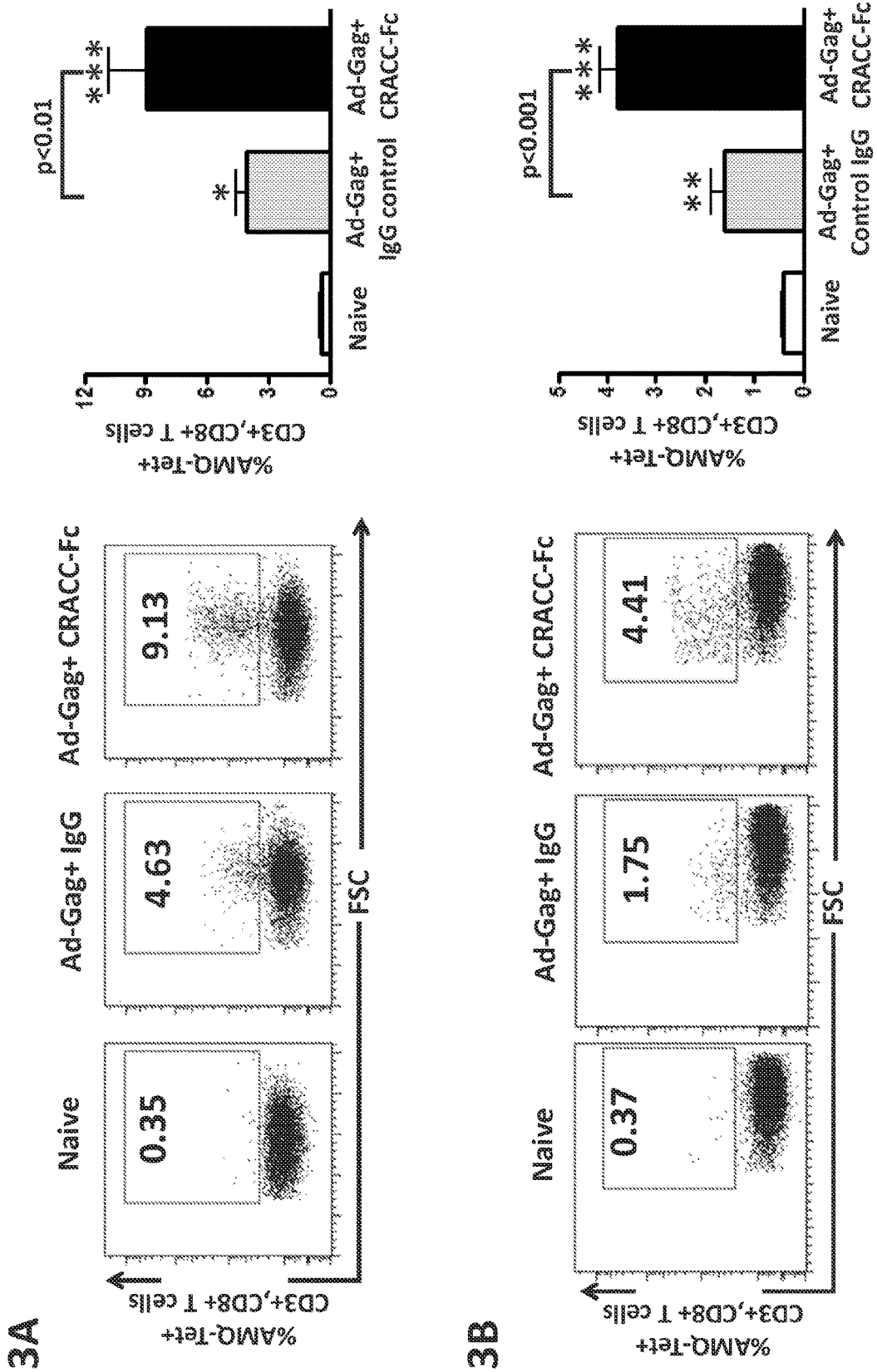
FIG. 3A is a series of flow cytometry dot plots, and a summary bar graph, depicting HIV-gag specific cellular immune responses elicited by rAd5-HIV/Gag and CRACC-Fc co-immunization by peripheral blood mononuclear cells (PBMCs). PBMCs from mock-treated (naïve), rAd5-HIV/Gag+IgG1 control-treated, or rAd5-HIV/Gag and CRACC-Fc fusion-treated mice were stained with a PE-conjugated H2-Kd-AMQMLKETI (SEQ ID NO:11) tetramer complex together with an APC-conjugated anti-CD3 and ALEXA FLUOR® 700-conjugated anti-CD8 antibodies. Data are representative of three independent experiments with similar results. *, , * denotes $p<0.05$, $p<0.01$, $p<0.001$ statistically different from mock injected animals. FSC refers to forward scatter in the dot plots, whereas the percentage of $CD3^+/CD8^+$ T cells is indicated at the left of the dot plots.
FIG. 3B is a series of flow cytometry dot plots, and a summary bar graph, depicting HIV-Gag specific cellular immune responses elicited by rAd5-HIV/Gag and CRACC-Fc co-immunization by splenocytes. Splenocytes from mock-treated (naïve), rAd5-HIV/Gag and IgG1 control-treated, or rAd5-HIV/Gag and CRACC-Fc fusion-treated mice were stained with a PE-conjugated H2-Kd-AMQMLKETI (SEQ ID NO:11) tetramer complex together with an APC-conjugated anti-CD3 and ALEXA FLUOR® 700-conjugated anti-CD8 antibodies Data are representative of three independent experiments with similar results. *, , * denotes $p<0.05$, $p<0.01$, $p<0.001$ statistically different from mock injected animals. FSC refers to forward scatter in the dot plots.

Example 4. Blockade of CRACC-CRACC Homophilic Interactions Enhances T Cell Responses to the Co-Administered Antigen In Vivo To study the effects of inhibiting CRACC-CRACC interactions in vivo, the following experiments were performed using an adenoviral construct (rAd5-HIV/Gag) capable of directing expression of the HIV-1 Glade B Gag protein (HXB2) (Aldhamen et al. (2012), supra) along with the CRACC-Fc fusion protein, or rat IgG as a control. BALB/c mice (n=7) were intraperitoneally (i.p.) injected with 200 μg of CRACC-Fc or control IgG. After 24 hours, mice were intramuscularly (i.m.) injected with $5\times10^6$ viral particles (vps) of rAd5-HIV/Gag along with a second 200 μg dose of either the CRACC-Fc or a control IgG. At 28 days post-vaccination, mice received a final 200 μg of the CRACC-Fc fusion or control IgG simultaneous with a homologous boosting vaccination again with rAd5-HIV/Gag vaccine (FIG. 9). HIV Gag-specific T cell responses were evaluated at 42 days post-vaccination, and the results of those evaluations show that co-administration of the CRACC-Fc fusion protein during rAd5-HIV/Gag vaccination significantly enhanced induction of vaccine-derived, HIV/Gag-specific splenic CD8+ T cell responses, as compared to control animals using HIV/Gag antigen-specific tetramer-binding assay (FIG. 3A). Specifically, PBMCs ($p<0.01$) (FIG. 3A) and splenocytes ($p<0.001$) (FIG. 3B) derived from mice co-immunized with rAd5-HIV/Gag and CRACC-Fc contained higher numbers of Gag-specific tetramer-positive CD8+ T cells, as compared to the respective cell populations isolated from control IgG treated mice.

Figure 4:
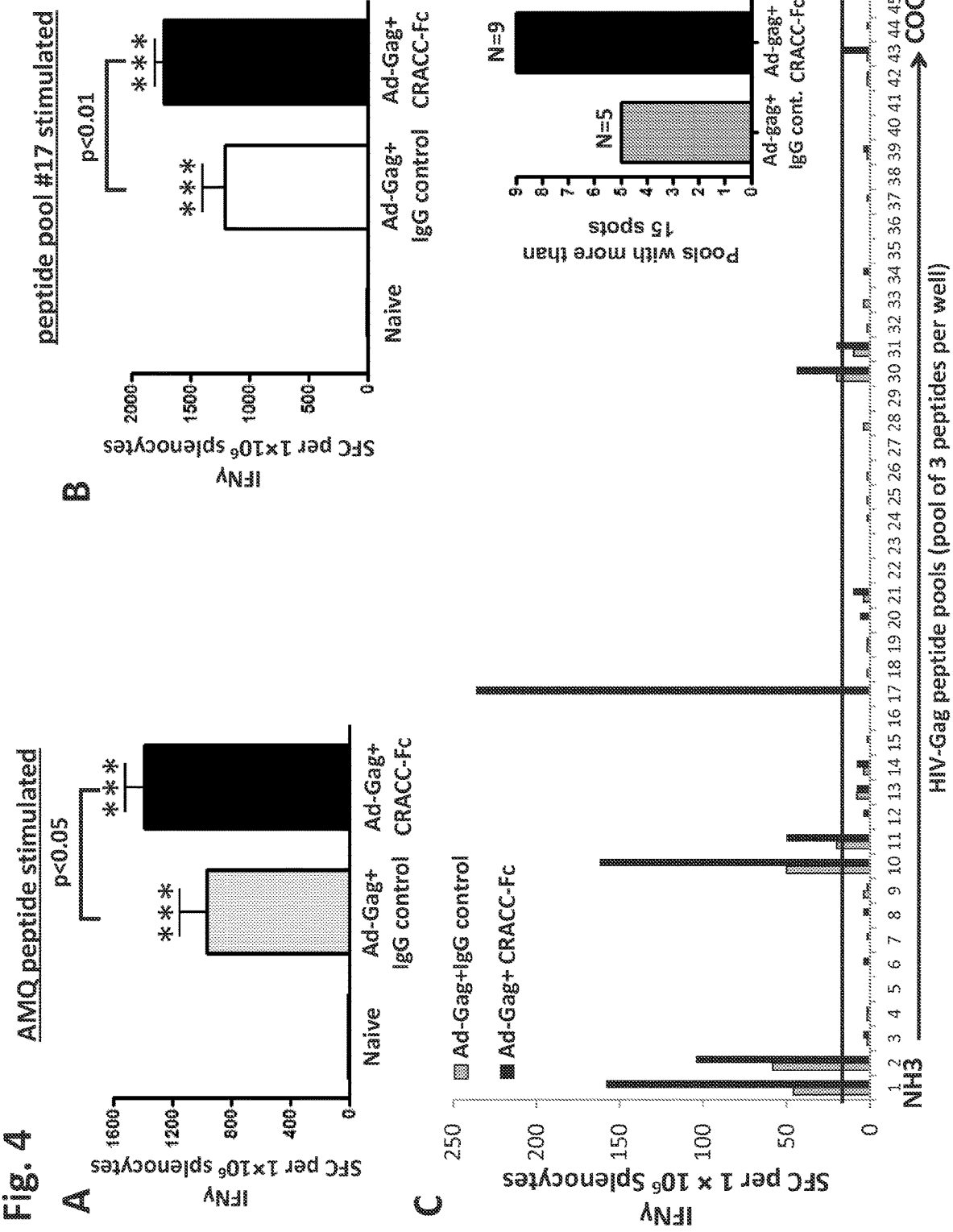
FIG. 4A is a bar graph depicting rAd5-Gag/CRACC-Fc vaccine formulation enhancement of T cell responses. Splenocytes derived from naïve, rAd5-HIV/Gag and control IgG or rAd5-HIV/Gag and CRACC-Fc were stimulated ex vivo with the 9-mer HIV/Gag-derived immunogenic peptide AMQMLKETI (SEQ ID NO:11), and Gag-specific IFNγ ELISpot assay was performed. Data are representative of three independent experiments with similar results. *, , * denotes $p<0.05$, $p<0.01$, $p<0.001$ statistically different from mock injected animals.
FIG. 4B is a bar graph depicting rAd5-Gag/CRACC-Fc vaccine formulation enhancement of T cell responses. Splenocytes derived from naïve, rAd5-HIV/Gag and control IgG or rAd5-HIV/Gag and CRACC-Fc-treated mice were stimulated ex vivo with a pool of three 15-mer HIV/Gag-derived immunogenic peptides. Data are representative of three independent experiments with similar results. *, , * denotes $p<0.05$, $p<0.01$, $p<0.001$ statistically different from mock injected animals.
FIG. 4C is a pair of bar graphs depicting an analysis of the breadth of Gag-specific T cell responses. Splenocytes from day 42 were equivalently pooled and IFNγ ELISpot analysis was carried out by stimulating individual wells ex vivo with a pool of 2-4 15mer peptides overlapped by 11 amino acids, not including peptides included in Figure A-B. Spot forming cells per million splenocytes are shown. The minimal threshold response is indicated by the line above 15. Data are representative of three (A-B) or two (C) independent experiments with similar results.
Figure 10:
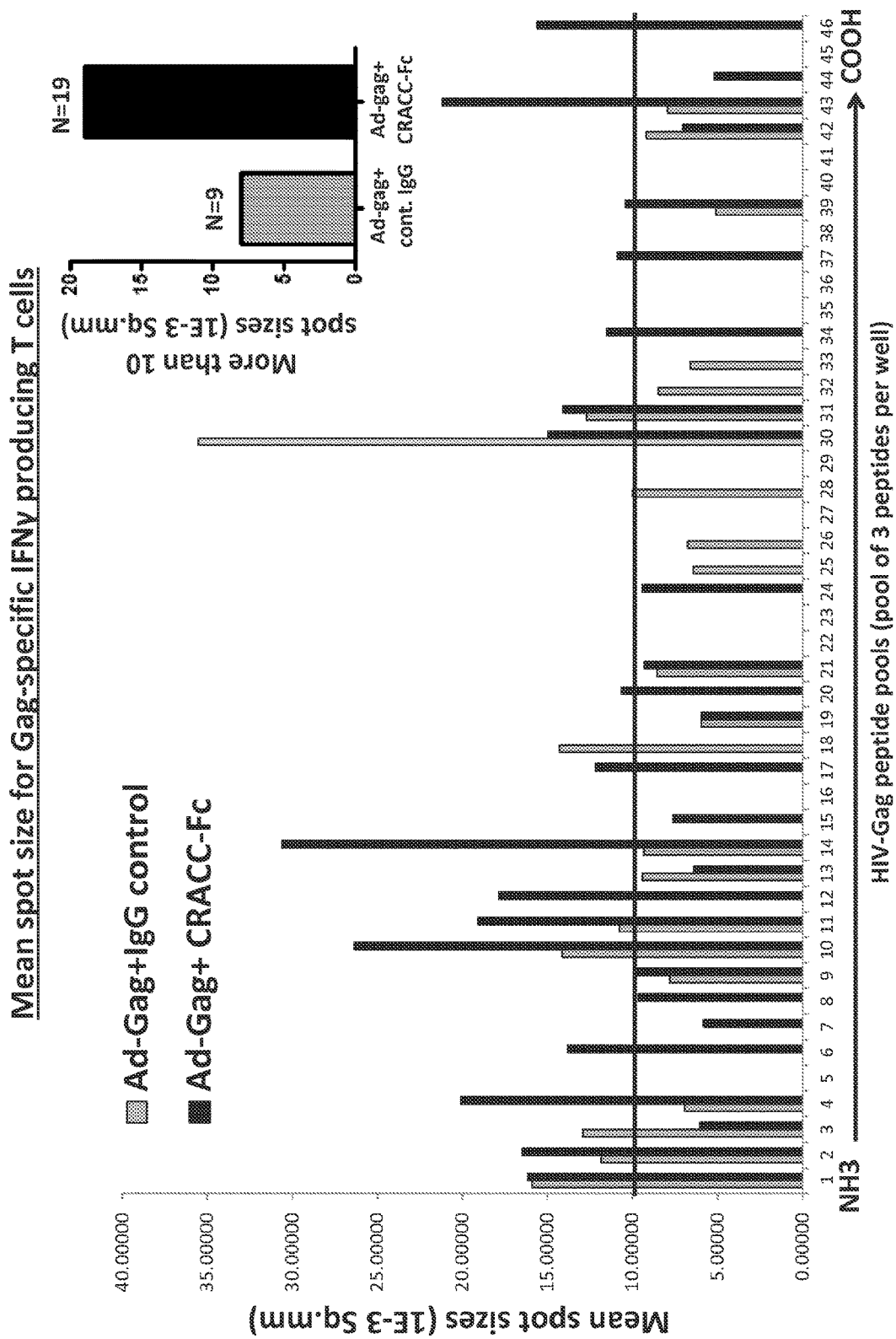
FIG. 10 is a pair of bar graphs depicting the mean spot size of IFNγ-producing splenocytes obtained from rAd5-HIV/Gag and CRACC-Fc vaccinated mice. Splenocytes from CRACC-Fc or control IgG antibody treated mice were equivalently pooled and IFNγ ELISpot analysis was carried out by stimulating individual wells ex vivo with a pool of 2-4 15mer peptides overlapped by 11 amino acids. Mean spot size of Gag-specific IFNγ-producing T cells is shown. Data are representative of two independent experiments.

Functional T cell memory responses were also evaluated using the IFNγ ELISpot assay. Following ex vivo stimulation with the immunodominant HIV/Gag peptide, AMQMLKETI (SEQ ID NO:11) (FIG. 4A) or utilizing a previously identified immunogenic peptide pool, pool #17 (FIG. 4B), splenocytes derived from mice co-immunized with rAd5-HIV/Gag and CRACC-Fc contained significantly increased numbers of Gag-specific, IFN-γ secreting cells, as compared to cells derived from controls (FIGS. 4A and 4B). The amino acid sequences of the peptides in the pool are as follows: TINEEAAEWDRLHPV (SEQ ID NO:94), EAAEWDRLHPVHAGP (SEQ ID NO:95), and WDRLHPVHAGPIPPG (SEQ ID NO:96). In addition, splenocyte preparations derived from the immunized mice with Gag derived peptide pools, each pool containing 2-4 Gag specific 15mer peptides spanning the entire HIV-Gag protein sequence, were stimulated as described in Aldhamen et al. (2011), supra. An increased breadth and magnitude in the elicited T cell immune recognition of HIV/Gag was observed where the CRACC-Fc fusion protein was included in the vaccination regimen. That is, the number of HIV Gag-specific peptides that triggered T cell responses from splenocytes derived from the rAd5-HIV/Gag and CRACC-Fc co-immunized mice was higher, as compared to similarly treated splenocytes derived from the rAd5-HIV/Gag and control IgG treated mice (FIG. 4C). Furthermore, the size and intensity (i.e. mean spot size (MSS)) of the responsive HIV/Gag-specific T cells established that such cells derived from CRACC-Fc fusion co-vaccinated mice expressed more IFNγ, as compared to cells isolated from control animals (FIG. 10). While the disclosure is not bound by any particular theory or mechanism of action, these data indicate that antigen-specific T cells, elicited following CRACC-Fc co-vaccination, exhibit increased level of effector function upon antigenic re-stimulation.

Figure 5:
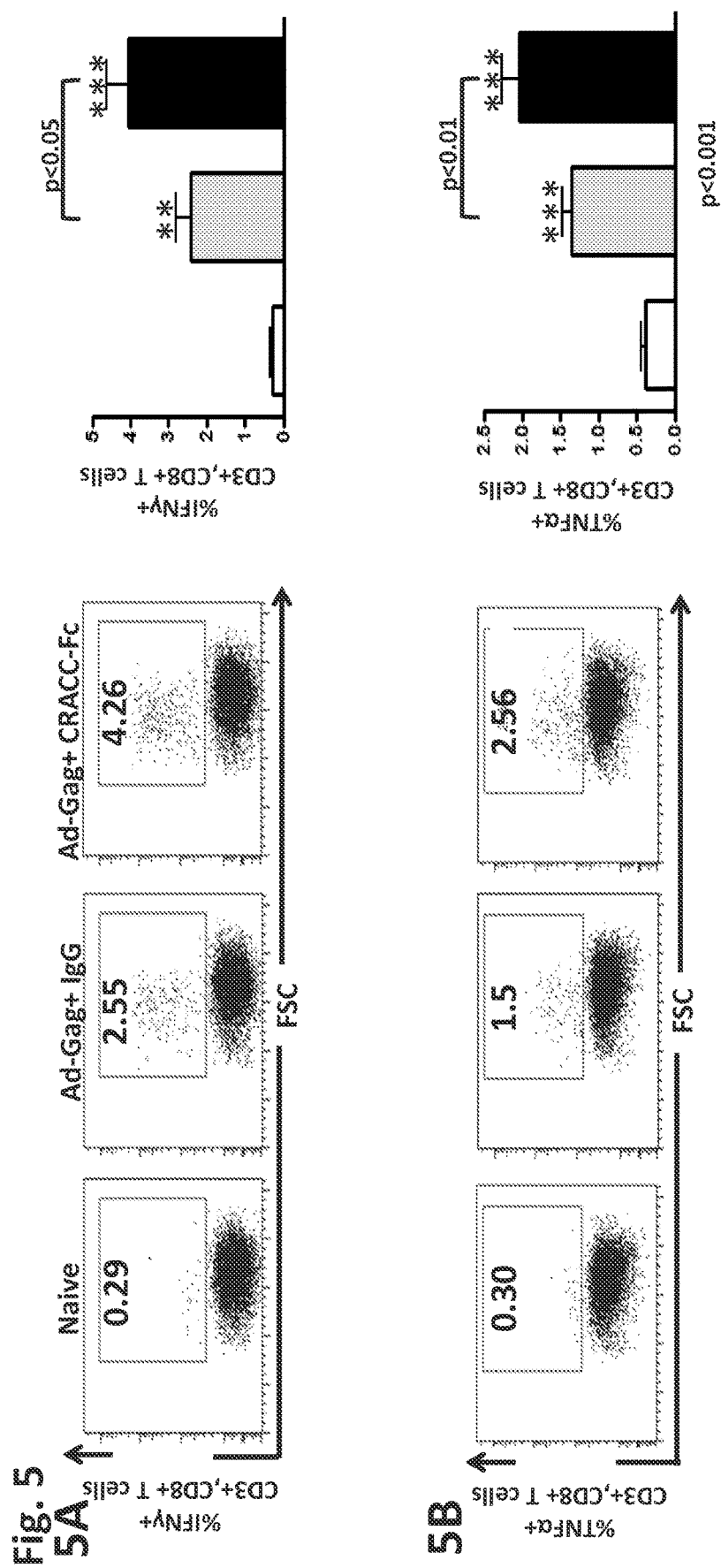
FIGS. 5A, 5B, and 5C are each a series of flow cytometry dot plots, and associated bar graphs summarizing the results set forth in the dot plots, depicting the cytokine secretion profiles of Gag-specific $CD3^+CD8^+$ T cells from mice vaccinated with rAd5-HIV/Gag and CRACC-Fc fusion protein. Splenocytes ($2\times10^6$ cells/well) derived from naïve or vaccinated mice were stimulated with the HIV-Gag immunogenic peptide, AMQMLKETI (SEQ ID NO:11) and fluorescence-assisted cell sorting (FACS) intracellular staining (ICS) analysis was performed. Gates were set based on negative control (naïve) and placed consistently across samples. The total frequency of splenic $CD8^+$ T cells derived from naïve or vaccinated mice expressing IFNγ (FIG. 5A), TNFα (FIG. 5B), and IL-2 (FIG. 5C) is shown as indicated. Data are representative of three independent experiments with similar results. The percentage of cytokine expressing cells is indicated in each dot plot. FSC refers to forward scatter in the dot plots.
FIGS. 5D, 5E, and 5F are each a series of bar graphs depicting the dual cytokine secretion profiles of Gag-specific $CD3^+CD8^+$ T cells from mice vaccinated with rAd5-HIV/Gag and CRACC-Fc fusion protein. The total frequency of splenic $CD8^+$ T cells derived from naïve or vaccinated mice expressing IFNγ/TNFα (FIG. 5D), IFNγ/IL-2 (FIG. 5E), and TNFα/IL-2 (FIG. 5F) is shown as indicated. Data are representative of three independent experiments with similar results. The percentage of cytokine expressing cells is indicated in each dot plot. FSC refers to forward scatter in the dot plots.
Figure 5:
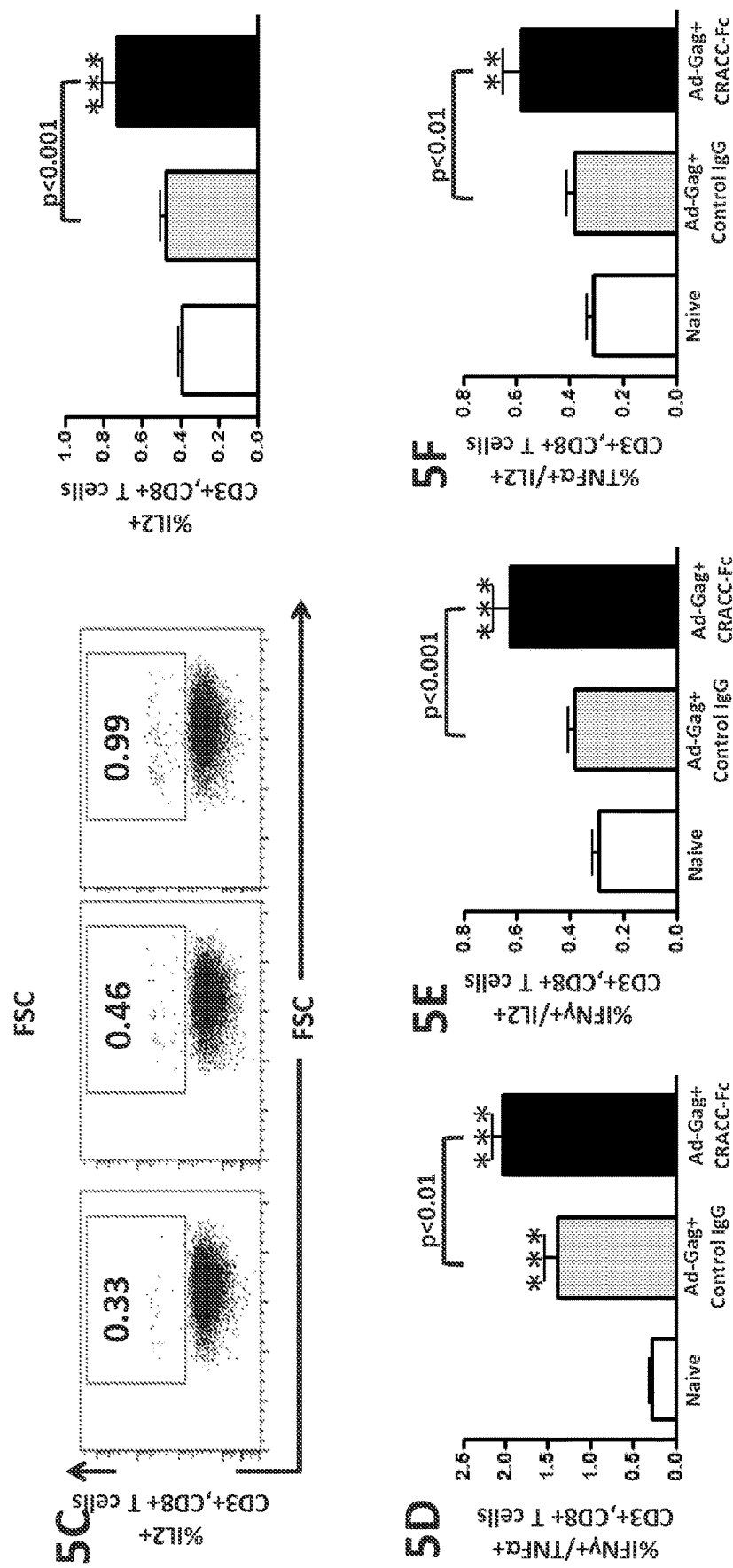
Figure 6:
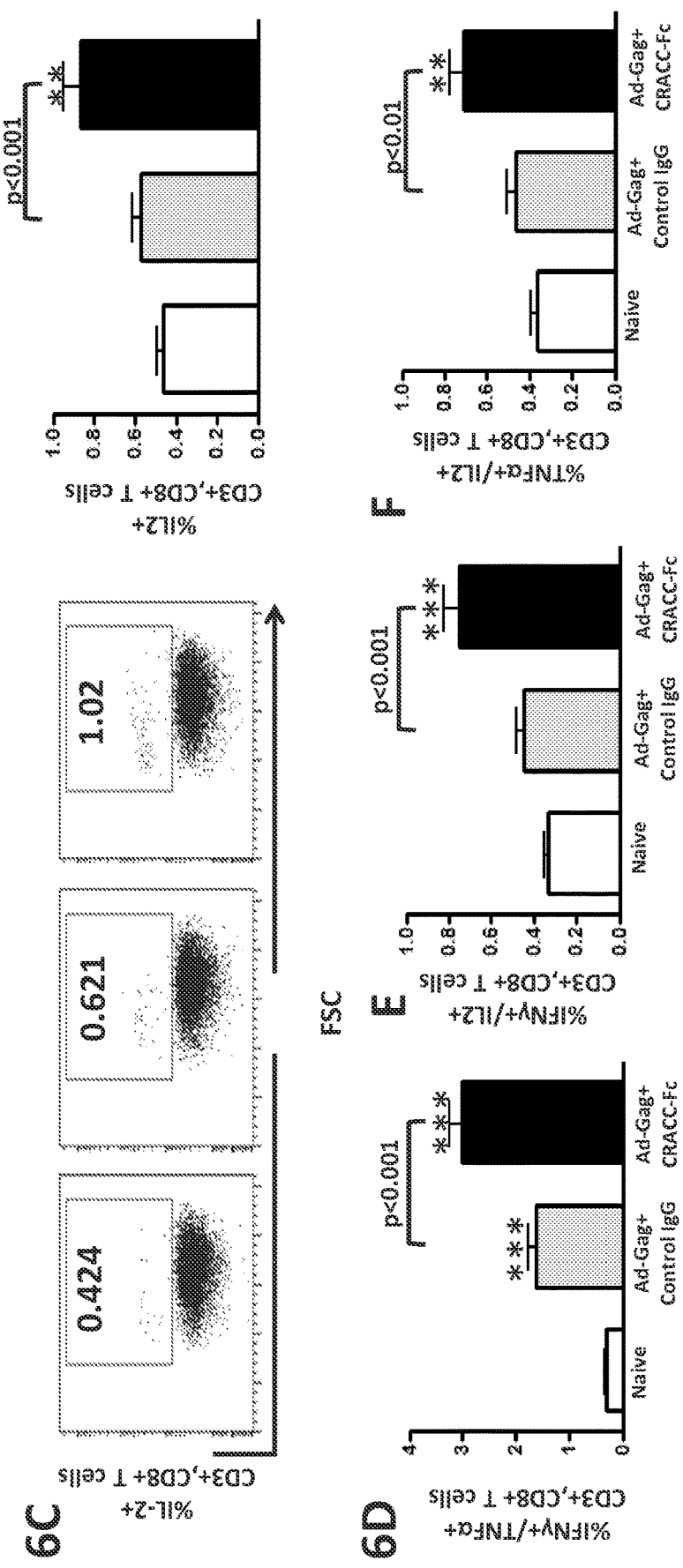
FIGS. 6A, 6B, and 6C are each a series of flow cytometry dot plots, and associated bar graphs summarizing the results set forth in the dot plots, depicting the increased breadth of Gag-specific $CD3^+CD8^+$ T cell responses following vaccination of mice with rAd5-HIV/Gag and CRACC-Fc fusion protein. Splenocytes ($2\times10^6$ cells/well) derived from naïve or vaccinated mice were stimulated with Gag-peptide pool #17 and fluorescence-assisted cell sorting (FACS) intracellular staining (ICS) analysis was performed. The total frequency of splenic $CD8^+$ T cells derived from naïve or vaccinated mice expressing IFNγ (FIG. 6A), TNFα (FIG. 6B), and IL-2 (FIG. 6C) is shown as indicated. Data are representative of two independent experiments with similar results. The percentage of cytokine expressing cells is indicated in each dot plot. FSC refers to forward scatter in the dot plots.
FIGS. 6D, 6E, and 6F are each a series of bar graphs depicting the increased breadth of Gag-specific CD3$^+$CD8$^+$ T cell responses following vaccination of mice with rAd5-HIV/Gag and CRACC-Fc fusion protein. The total frequency of splenic CD8$^+$ T cells derived from naïve or vaccinated mice expressing IFNγ/TNFα (FIG. 6D), IFNγ/IL-2 (FIG. 6E), and TNFα/IL-2 (FIG. 6F) is shown as indicated. Data are representative of two independent experiments with similar results. The percentage of cytokine expressing cells is indicated in each dot plot. FSC refers to forward scatter in the dot plots.

Example 5. Blocking CRACC-CRACC Interaction During Vaccination Induces Poly-Functional T Cell Responses to the Co-Administered Antigen In Vivo Immune modulators that enhance the generation and activity of antigen-specific, poly-functional T cells may facilitate the induction of a protective and long lived memory immune responses. Betts et al. (2006) *Blood* 107: 4781-4789 and Darrah et al. (2007) *Nat Med* 13:843-850. Detection and characterization of these polyfunctional T cells was performed by way of measuring the expression of several cytokines by HIV/Gag-specific CD8$^+$ T cells generated after rAd5-HIV/Gag and CRACC-Fc protein co-immunization. Multiparameter flow cytometry analysis was used to determine the frequency of CD8$^+$ T cells producing IFNγ, TNFα, and/or IL-2 after ex vivo stimulation with HIV-Gag specific immunogenic AMQMLKETI (SEQ ID NO:11) peptide. We observed significantly higher frequencies of HIV-Gag-specific IFNγ (p<0.05), TNFα (p<0.01), and IL-2 (p<0.001)-expressing CD8$^+$ T cells derived from rAd5-HIV/Gag and CRACC-Fc co-immunized mice, as compared to mice treated with the rAd5-HIV/Gag and control IgG (FIG. 5A-C). The frequency of a dual cytokine producing CD8$^+$ T cells was also evaluated. Significant increases in IFNγ/TNFα (p<0. 01), IFNγ/IL-2 (p<0. 001), and TNFα/IL-2 expressing, HIV/Gag-specific, CD8$^+$ T cells (FIG. 5D-F) were observed from CD8$^+$ T cells derived from rAd5-HIV/Gag and CRACC-Fc co-immunized mice. Similarly, more pronounced results were also observed when splenocytes were stimulated ex vivo with the HIV/Gag-peptide pool, pool #17, (FIGS. 6A-6F). Evaluating Gag-specific CD3$^+$ T cell responses revealed minor induction compared to the naives and no significant differences between the experimental and control groups. These data strongly suggest that in vivo administration of CRACC-Fc fusion protein facilitates improved induction both the magnitude and quality of antigen-specific CD8$^+$ T cell immune responses.

Figure 7A:
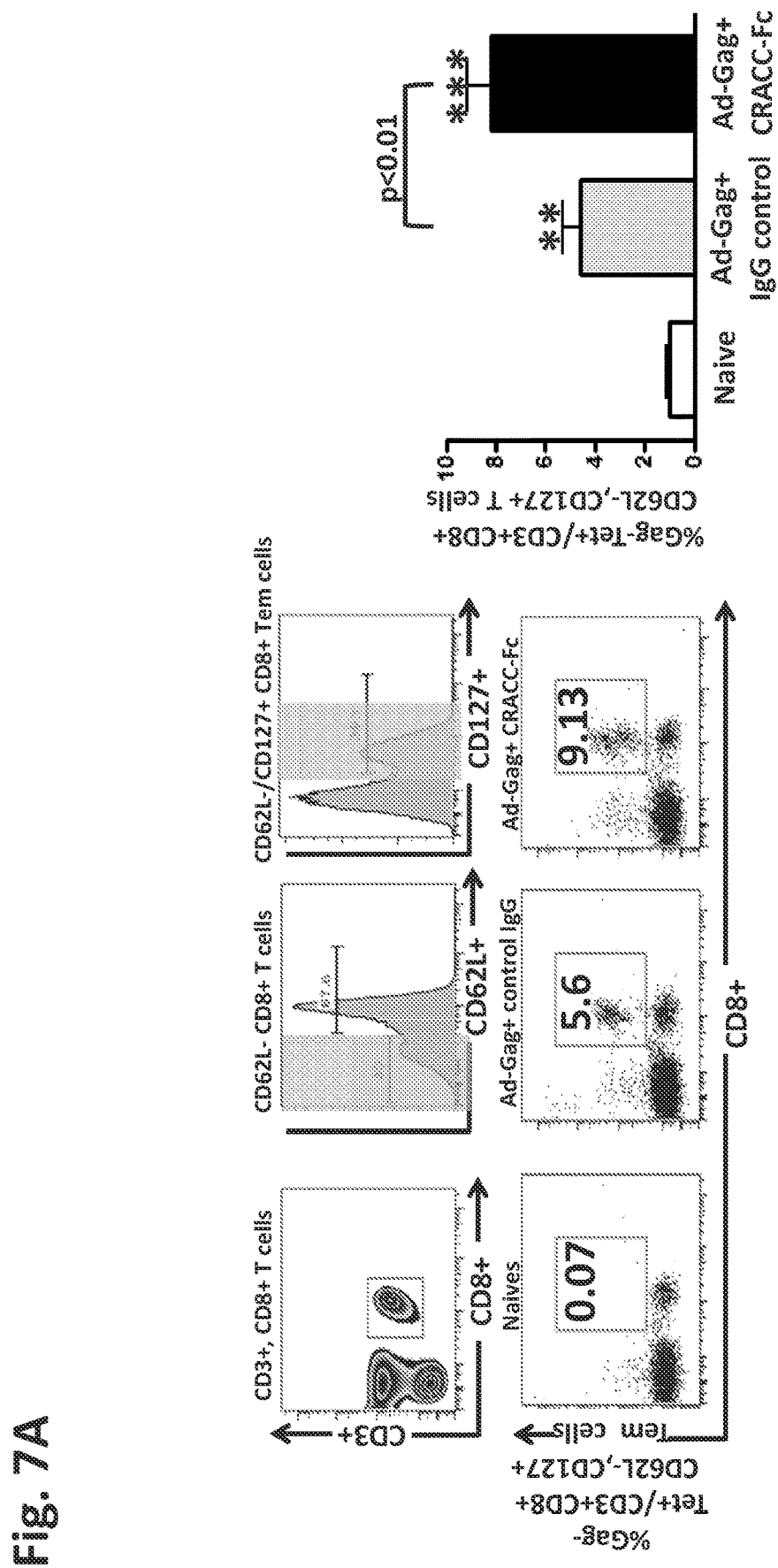
FIGS. 7A and 7B are each a series of histograms and dot plots depicting the increase in magnitude of Gag-specific TEM CD8$^+$ T cell responses following vaccination with rAd5-HIV/Gag virus and CRACC-Fc fusion protein. Multiparameter Gag-tetramer binding assays were performed in PBMCs (FIG. 7A) or splenocytes (FIG. 7B) of naïve or vaccinated mice to enumerate the frequency of Gag-specific tetramer positive effector memory (CD62L$^{low}$ CD127$^{high}$) CD8$^+$ T cells. , * denotes p<0.01, p<0.001 statistically different from naive animals. Data are representative of three independent experiments with similar results.
Figure 7B:
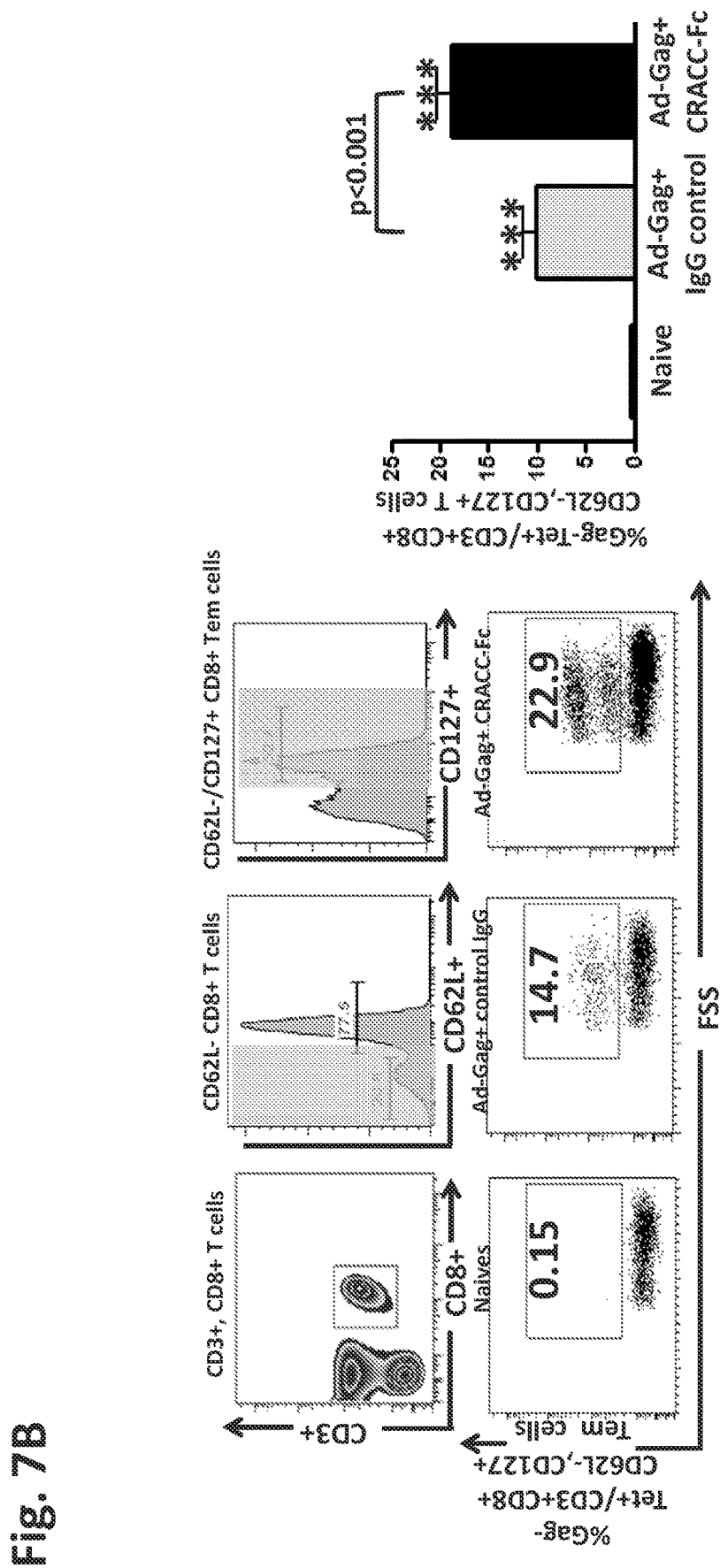

Example 6. HIV/Gag-Specific T Lymphocytes Elicited by CRACC-Fc Co-Vaccination Exhibit TEM Memory-Biased Phenotype To evaluate the phenotype of the induced Gag-specific memory CD8$^+$ T cell response—that is, to determine whether the rAd5-HIV/Gag and CRACC-Fc co-vaccination produces an effector memory CD8$^+$ T cell response as compared to a central memory response—a FACS analysis was used to measure CD62L and CD127 expression on the Gag-specific CD8$^-$ T cells. Peripheral blood (FIG. 7A) and splenic (FIG. 7B) CD8$^+$ T cells derived from rAd5-HIV/Gag and CRACC-Fc regimen had statistically significant increases in the frequencies of Gag-specific tetramer positive CD127$^{high}$CD62$^{low}$ effector memory CD8$^+$ T cells, as compared to the respective cell populations isolated from control mice. No statistically significant increases in Gag-specific central memory (T$_{CM}$) CD8+ T cell were observed in PBMCs and splenocytes of both the experimental and control groups. These data suggest that, similar to EAT-2 overexpression, blockade of CRACC-CRACC interactions during vaccination directs the elicited antigen—specific CD8$^+$ T cells toward T$_{EM}$ phenotype. Additionally, these data suggest that the enhanced cellular immune responses triggered following EAT-2 overexpression may be associated. with diminishing CRACC-CRACC interaction.

Figure 8A:
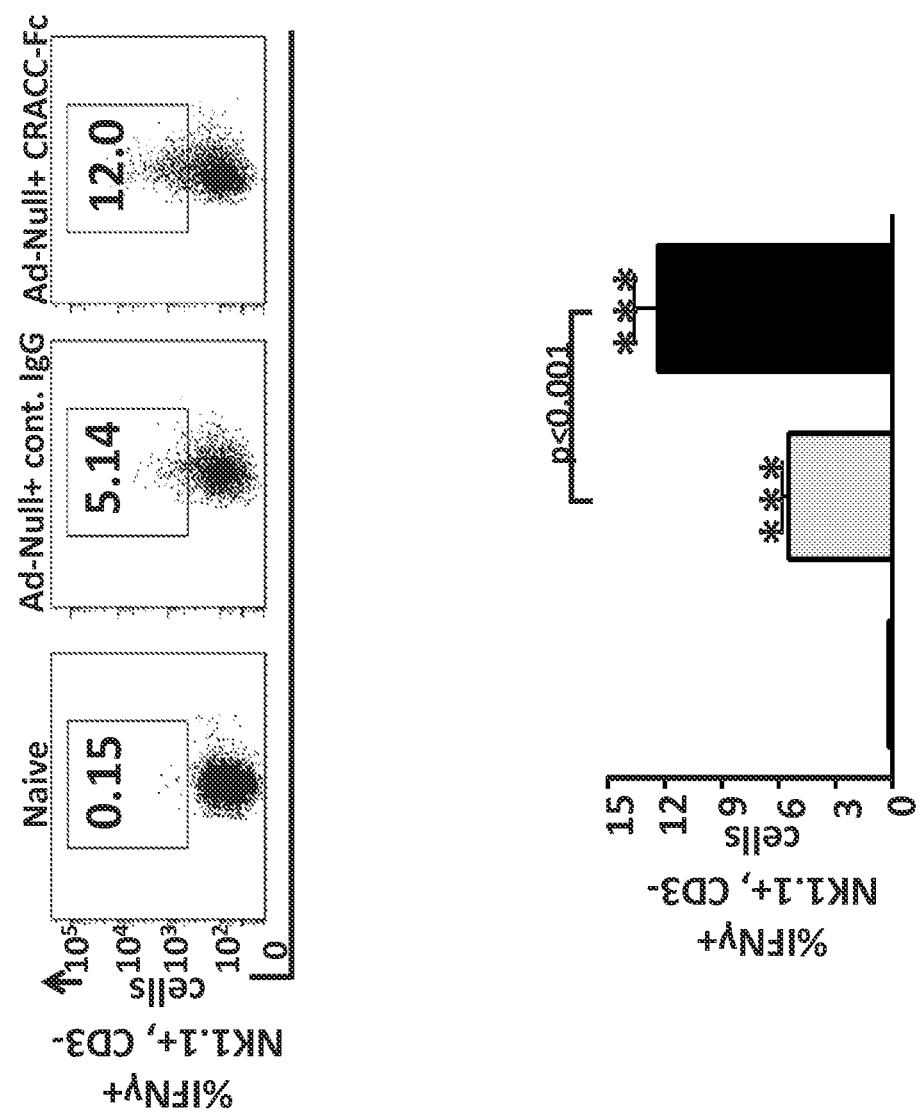
FIGS. 8A, 8B, 8C, and 8D are each a series of flow cytometry dot plots, and associated bar graphs summarizing the results set forth in the dot plots, depicting the enhancement of an innate immune response by an CRACC ECD-Fc fusion protein. Male C57BL/6 mice (n=5) were mock injected or I.P. injected with a mixture of rAd5-Null (2×10$^{10}$ vps/mouse) and either CRACC-Fc fusion protein or control IgG antibodies (200 μg/mouse) (prepared in a 200 μl sterile PBS). After 12 hours, mice were sacrificed and splenocytes were prepared. Cells were stained with the following antibodies; CD69-PE, CD3-APC, CD19-PerCpCy5.5, CD8 ALEXA FLUOR® 700. For DCs maturation, cells were stained with the following antibodies; CD11c-PECy7, CD11b-APC-Cy7, CD80-PerCpCy5.5, CD86-Pacific blue, MHC-II-ALEXA FLUOR® 700. For IFNγ expression in NK cells, cells were incubated with Golgi plug for 90 minutes at 37° C. prior to staining with the following antibodies; CD69-PE, CD3-APC/Cy7, NK1.1-PECy7, and IFNγ-APC.
Figure 8B:
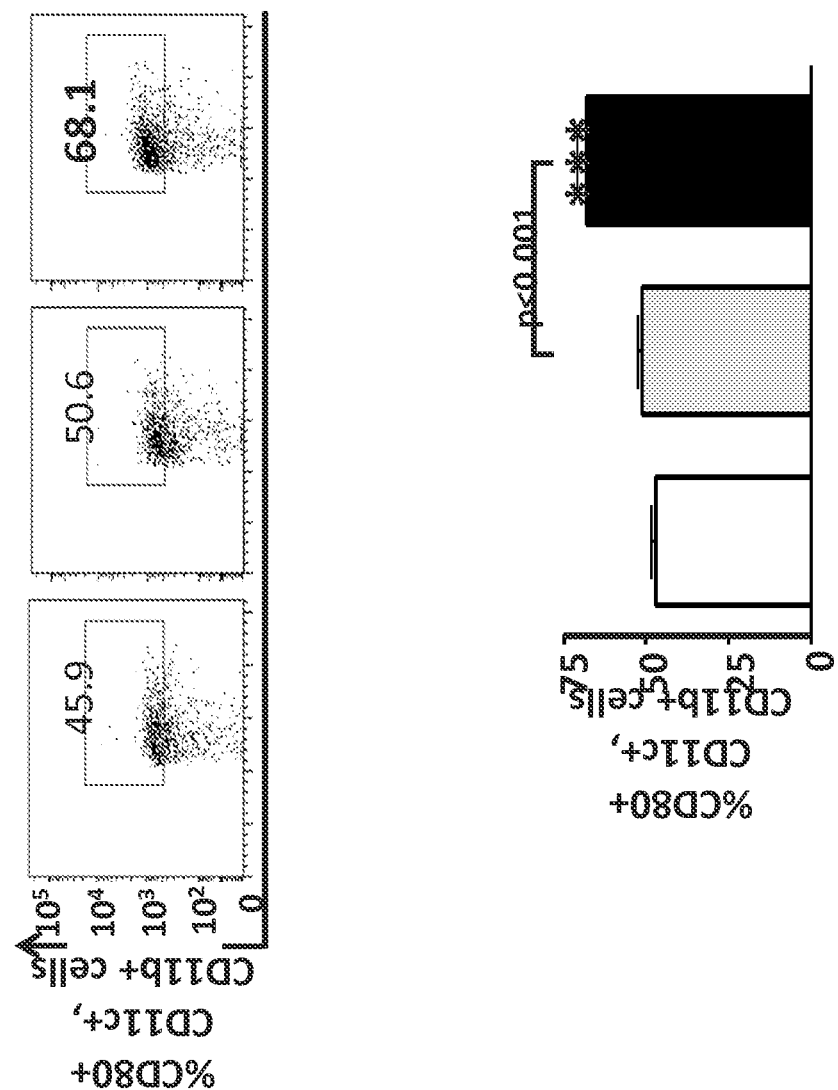
Figure 8C:
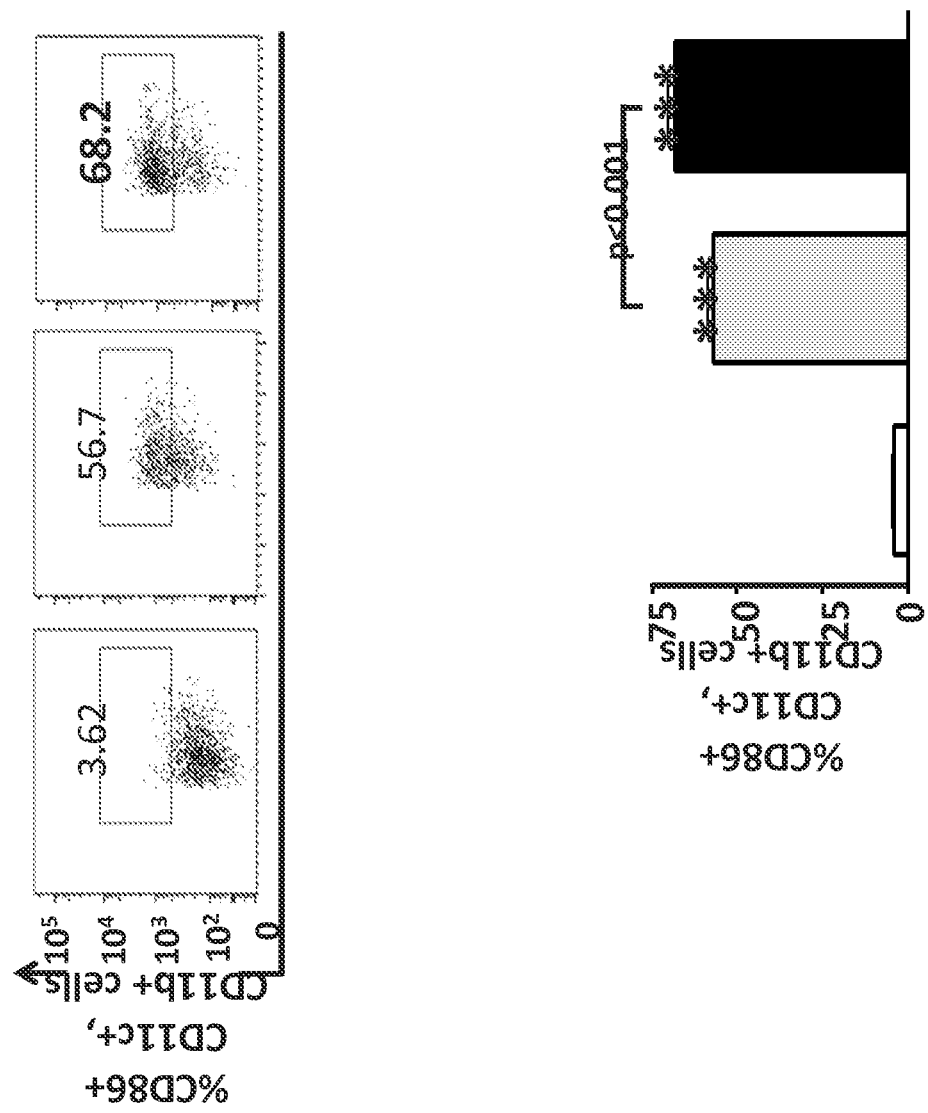
Figure 8D:
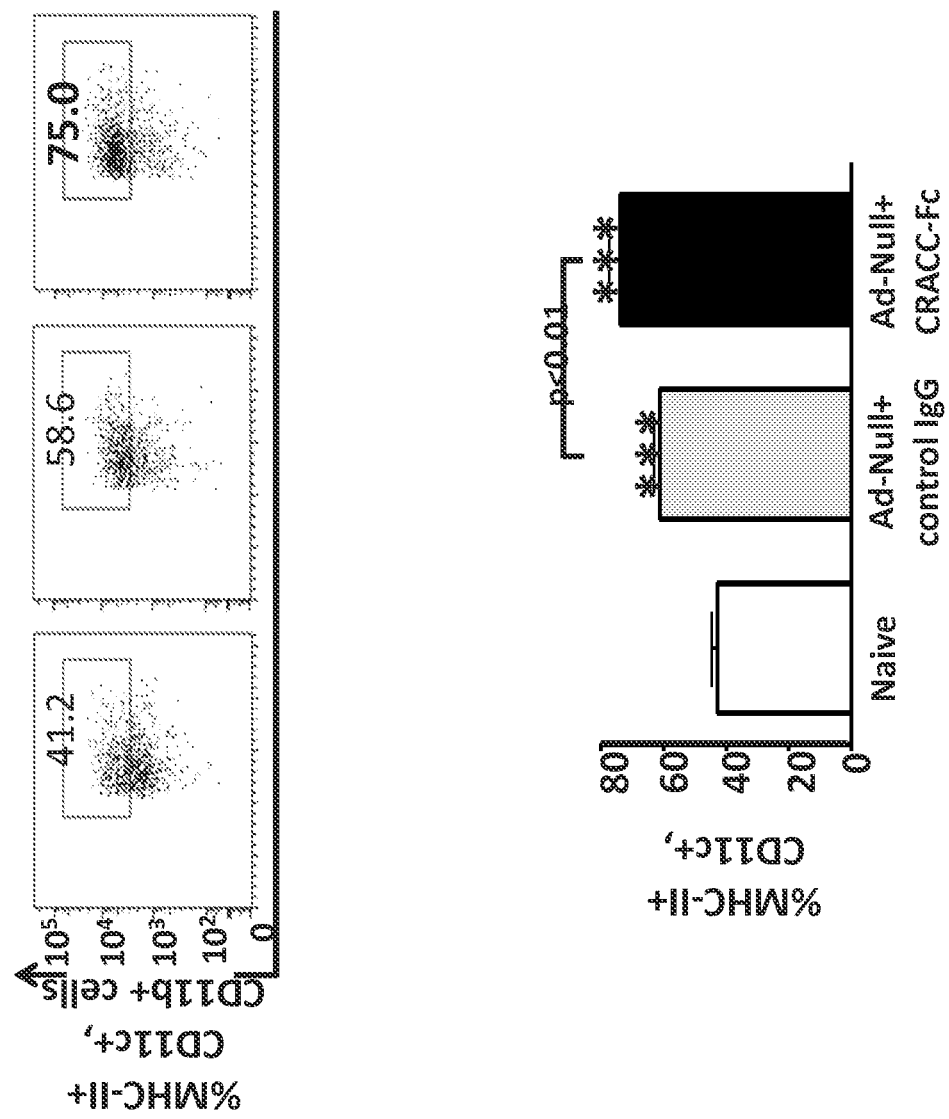

Example 7. Blockade of CRACC-CRACC Interaction Enhances Ad5-Vaccine Elicited Innate Immune Responses In Vivo The effect of the adenoviral/CRACC-Fc co-vaccination on innate immune responses was also evaluated. For these studies, CRACC-Fc or control IgG antibody was mixed with rAd5-Null adenovirus and administered i.p. to the mice. After 12 hours, the activation of innate immune cells was evaluated by flow cytometry analysis. Administering the CRACC-Fc fusion protein along with rAd5-Null virus induced significantly (p<0.001) higher numbers of IFNγ-expressing NK cells (FIG. 8A). In addition, dendritic cells (DCs) derived from Ad5 and CRACC-Fc formulation are highly matured. Significantly increased expression levels of the co-stimulatory molecules CD80 (FIG. 8B), CD86 (FIG. 8C), and MHC class II (I-A/I-E) (FIG. 8D) by CD11c$^+$CD11b$^+$ DCs, as compared to cells derived from rAd5-Null and control IgG treated mice, were also observed.

Figure 11A:
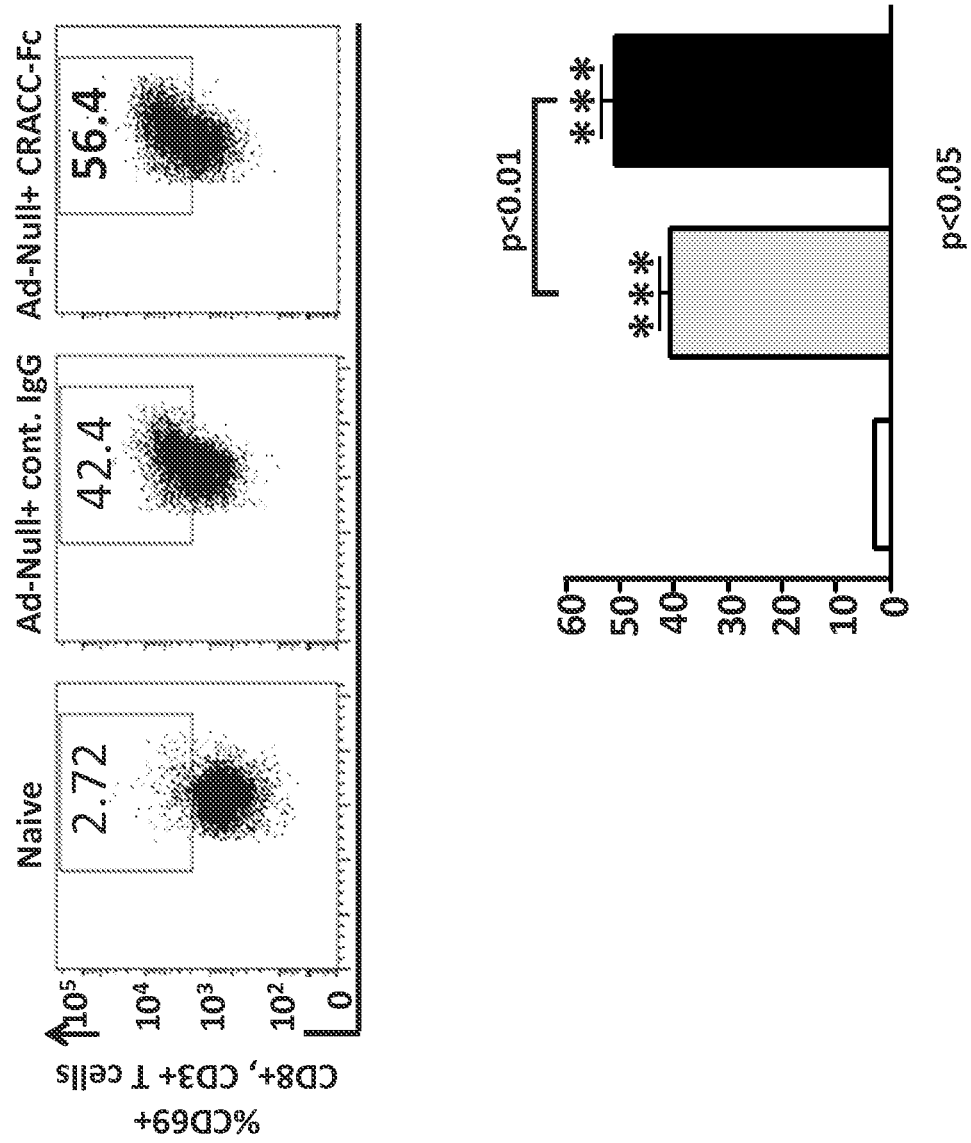
Figure 11C:
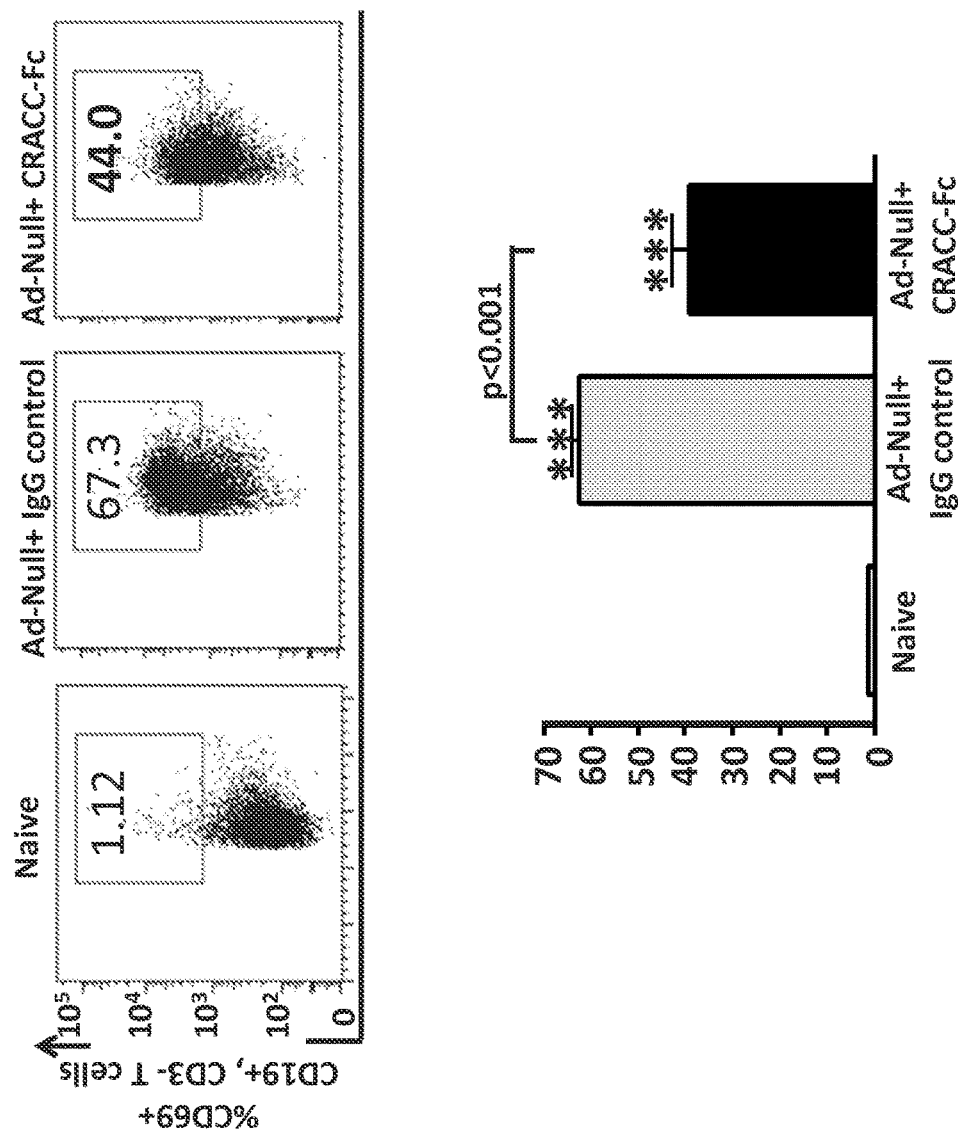

Early activation of T cells following rAd5-Null and CRACC-Fc co-vaccination was also studied. We observed significantly increased expression levels of the immune cell activation marker, CD69, on CD3$^+$CD8$^+$ T cells (p<0.01) and CD3$^+$CD8$^-$ T cells (p<0.05) in cells derived from CRACC-Fc co-vaccinated mice, as compared to controls (FIG. 11A-B). In contrast, we observed reduced B cell activation in the spleen of rAd5-Null and CRACC-Fc co-vaccinated mice, as compared to the controls (FIG. 11C)

Figure 12A:
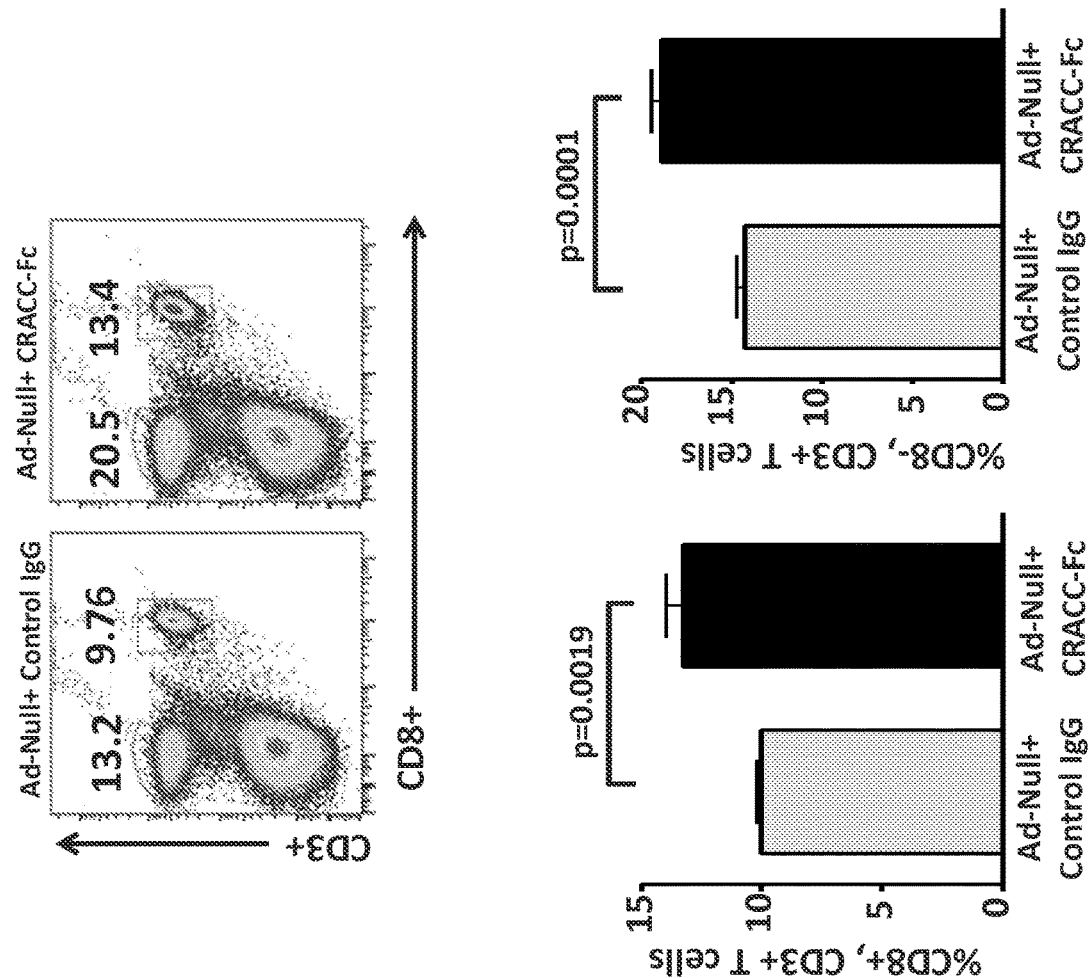
FIGS. 12A and 12B are each a series of flow cytometry histograms, and associated bar graphs summarizing the results set forth in the dot plots, depicting the frequency of T and B lymphocytes following rAd5-Null and CRACC-Fc vaccination.
Figure 12B:
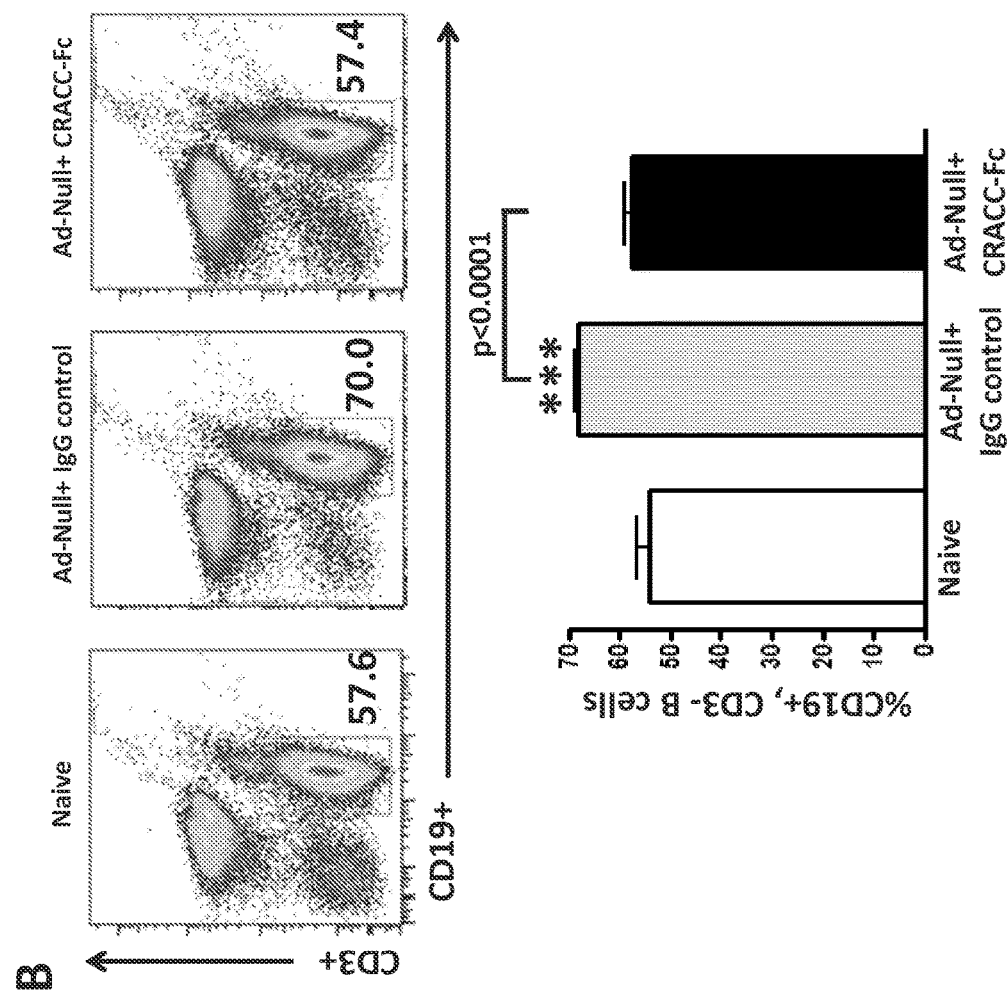

Furthermore, these studies revealed that administration of CRACC-Fc along with rAd5 increases the percentages/proliferation of the total number of CD8$^+$ and CD3$^+$ T cells, as compared to controls (FIG. 12A). A minor reduction in the percentages of total number of B cells in splenocytes derived from CRACC-Fc co-treated mice, as compared to the control (FIG. 12B) was detected. These data suggest that CRACC-Fc fusion formulated vaccines improve innate immunostimulatory activity, an activity that can enhance the down-stream cellular immune responses, therefore improving the efficacy of vaccines.

The above-described experiments involve the use of a CRACC ECD-Fc fusion protein as an inhibitor of the CRACC-CRACC homophilic interaction. A second series of experiments were performed using an antagonist anti-CRACC antibody (R&D Systems, catalogue number: FAB4628A). Briefly, adult male C57BL/6 mice were vaccinated i.m. into the tibialis anterior of the right hindlimb with rAd5-Gag (1×10$^8$ total viral particles (vps)) in a total volume of 20 mL). Fourteen days following rAd5-Gag injection, splenocytes were isolated from the mice. 4×10$^6$ spenocytes were either treated with APC-conjugated anti-CRACC antibody or a control IgG2a antibody (Saquin Inc., Amsterdam; catalogue number: M1452). One hour following antibody treatment, cells were further stimulated for 6 hours with a Gag immunodominant peptide (QBI, Gaithersburg, Md.; QBI 304796) in the presence of a protein transport inhibitor (Golgi Plug™ (BD Biosciences). Intracellular staining was performed as described in Aldhamen et al. (2012), supra. In brief, cells were stained with APC-Cy7-CD3, Alexa™ Fluor 700-CD8a, and CD16/32 antibodies, fixed with 2% formaldehyde, permeabilized with 0.2% saponin, and stained for intracellular cytokines with PE-Cy7-TNFα, FITC-IFNγ (BD Biosciences), and PErCp-Cy5.5-IL2 (BioLegend, San Diego, Calif.).

Stimulation with the Gag immunodominant peptide in the presence of the anti-CRACC antibody resulted in significant increases in the expression levels of IFNγ, TNFα, and IL-2 from Gag-specific memory CD8$^+$ T cells (FIGS. 13A-13C). These results further indicate that inhibition of CRACC during antigen stimulation of T cells enhances T cell responses to the antigen.

Example 8. The Use of an Antagonist Anti-CRACC Antibody

The above-described experiments involve the use of a CRACC ECD-Fc fusion protein as an inhibitor of the CRACC-CRACC homophilic interaction. A second series of experiments were performed using an antagonist anti-CRACC antibody (R&D Systems, catalogue number: FAB4628A). Briefly, adult male C57BL/6 mice were vaccinated i.m. into the tibialis anterior of the right hindlimb with rAd5-Gag ($1\times10^8$ total viral particles (vps)) in a total volume of 20 mL). Fourteen days following rAd5-Gag injection, splenocytes were isolated from the mice. $4\times10^6$ spenocytes were either treated with APC-conjugated anti-CRACC antibody or a control IgG2a antibody (Saquin Inc., Amsterdam; catalogue number: M1452). One hour following antibody treatment, cells were further stimulated for 6 hours with a Gag immunodominant peptide (QBI, Gaithersburg, Md.; QBI 304796) in the presence of a protein transport inhibitor (Golgi Plug™ (BD Biosciences). Intracellular staining was performed as described in Aldhamen et al. (2012), supra. In brief, cells were stained with APC-Cy7-CD3, Alexa™ Fluor 700-CD8a, and CD16/32 antibodies, fixed with 2% formaldehyde, permeabilized with 0.2% saponin, and stained for intracellular cytokines with PE-Cy7-TNFα, FITC-IFNγ (BD Biosciences), and PErCp-Cy5.5-IL2 (BioLegend, San Diego, Calif.).

Stimulation with the Gag immunodominant peptide in the presence of the anti-CRACC antibody resulted in significant increases in the expression levels of IFNγ, TNFα, and IL-2 from Gag-specific memory CD8$^+$ T cells (FIG. 13). These results further indicate that inhibition of CRACC during antigen stimulation of T cells enhances T cell responses to the antigen.

DNA Vaccination

Similar results were obtained using splenocytes derived from mice vaccinated with DNA encoding HIV/Gag protein. That is, re-stimulation of these splenocytes with Gag peptide, in the presence of the anti-CRACC antibody, gave rise to a greater production of cytokines by CD8$^+$ T cells, as compared to the production of cytokines by CD8$^+$ T cells re-stimulated in the presence of the control antibody.

Human Peripheral Blood Mononuclear Cells

In addition to using murine splenocytes, a similar study was performed using human peripheral blood mononuclear cells (PBMCs) obtained from patients infected with human cytomegalovirus (hCMV). Human PBMCs-derived from CMV positive patients were stimulated with the CMV phosphoprotein Pp65 (UL83) (Prospec-Tany Technologies Ltd, East Brunswick, N.J.; catalogue number: CMV 215-a). Cells were then stained with APC-Cy7-CD3, ALEXA FLUOR®700-CDSa, and CD16/32 Fc-block, and PE-IFNγ (BD Biosciences) as described above. The violet fluorescent reactive dye (ViViD, Invitrogen, Carlsbad, Calif.) was also included as a viability marker to exclude dead cells from the analysis. Similar to the results observed with murine splenocytes, ex vivo re-stimulation of human PBMCs with the hCMV peptide, in the presence of the anti-CRACC antibody, gave rise to a greater production of cytokines by CD8$^+$ T cells, as compared to the production of cytokines by CD8$^+$ T cells re-stimulated in the presence of the control antibody.

Example 9. Upregulation of CRACC Polypeptides in HIV-1 and hCMV-Infected Patients To determine whether CRACC receptor expression may increase on CD8$^+$ T cells derived from chronically infected patients, including hCMV and HIV-1 infected individuals, and whether such increased expression of CRACC receptor function may inhibit CD8$^+$ T cells responses, the following experiment was performed. PBMCs obtained from CMV$^+$ HIV$^+$ patients or normal blood donors were stained with anti-CD3, anti-COS and anti-CRACC-specific antibodies and flow cytometry analysis was conducted. Surprisingly, significantly increased expression levels of CRACC were observed on CD8$^+$ T cells derived from CMV$^+$HIV$^+$ patients, as compared to cells derived from normal blood donors (FIG. 14).

Example 10. Effect of CRACC Inhibition on T Cell Responses to Bacterial Antigens/Synergy with PD-1 Inhibition In addition to the HIV Gag and CMV antigens tested above, a set of experiments were performed to evaluate the ability of CRACC inhibition to enhance T cell responses to a protozoan antigen. Briefly, Balb/c mice were vaccinated with an adenovirus ($10^{10}$ vps/mouse) encoding the *Plasmodium falciparum*-derived circumsporozoite antigen, CSP, the rAd5-Null virus, or the rAd5-EAT2 virus. Mice were then challenged with mosquitos and infected with pathogenic sporozoites.

Figure 15:
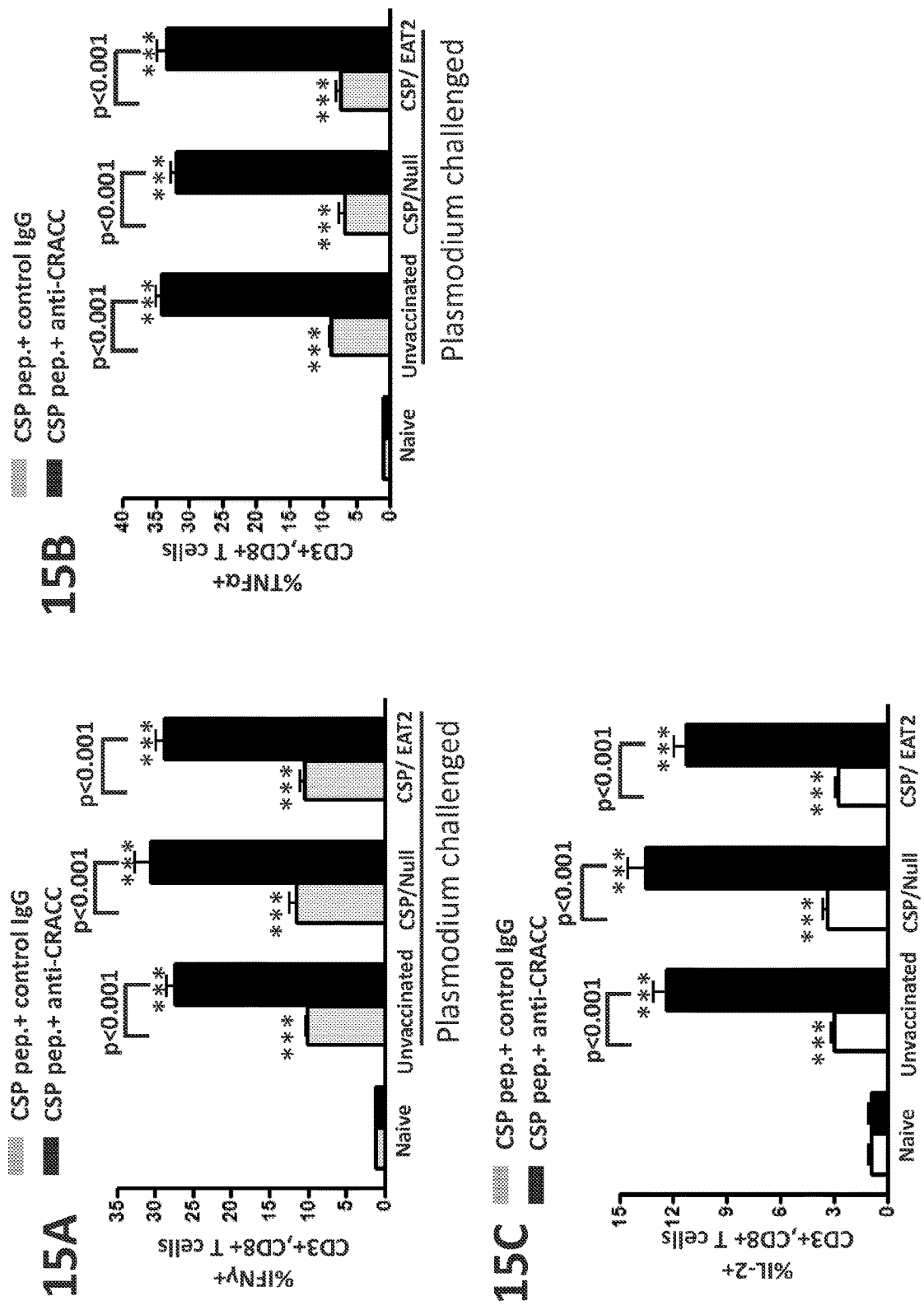
FIGS. 15A, 15B, and 15C are a series of bar graphs depicting then enhancement of CSP-specific CD8$^+$ T cell responses by CRACC inhibition. Splenocytes obtained from mice infected with malaria or non-infected mice were contacted ex vivo with a CSP peptide (CSP pep.) and with an anti-CRACC antibody or a control IgG antibody that does not bind to CRACC. The percentage of splenic CD3$^+$CD8$^+$ T cells expressing IFNγ (FIG. 15A), TNFα (FIG. 15B), and IL-2 (FIG. 15C) is shown as indicated. *** denotes p<0.001 statistically different from mock injected animals.

Splenocytes obtained from naïve or infected mice were pretreated with an antagonist anti-CRACC antibody, an anti-PD-1 antibody, or a control antibody one hour prior to CSP peptide restimulation. Cells were stimulated with the CSP peptide for six hours and in the presence of the Golgi inhibitor Golgi Plug (above). The viability dye, ViViD, was also included. Cells were then fixed, permeabilized, and intracellularly stained with FITC-IFNγ, Pe-Cy7-TNFα, and PE-IL2 antibodies for about three hours. Data were collected on the LSR-II machine and analyzed by FlowJo software. Two-Way ANOVA was used for statistical analysis. $P<0.5$ was deemed statistically significant. Consistent with the ex vivo data that was observed in splenocytes derived from Ad-HIV/gag vaccinated mice, inhibiting CRACC-CRACC interaction prior to peptide re-stimulation increased the production of CSP-specific cytokines (IFNγ, TNFα, and IL-2) from CD8$^+$ T cells (FIGS. 15A, 15B, and 15C).

Figure 16:
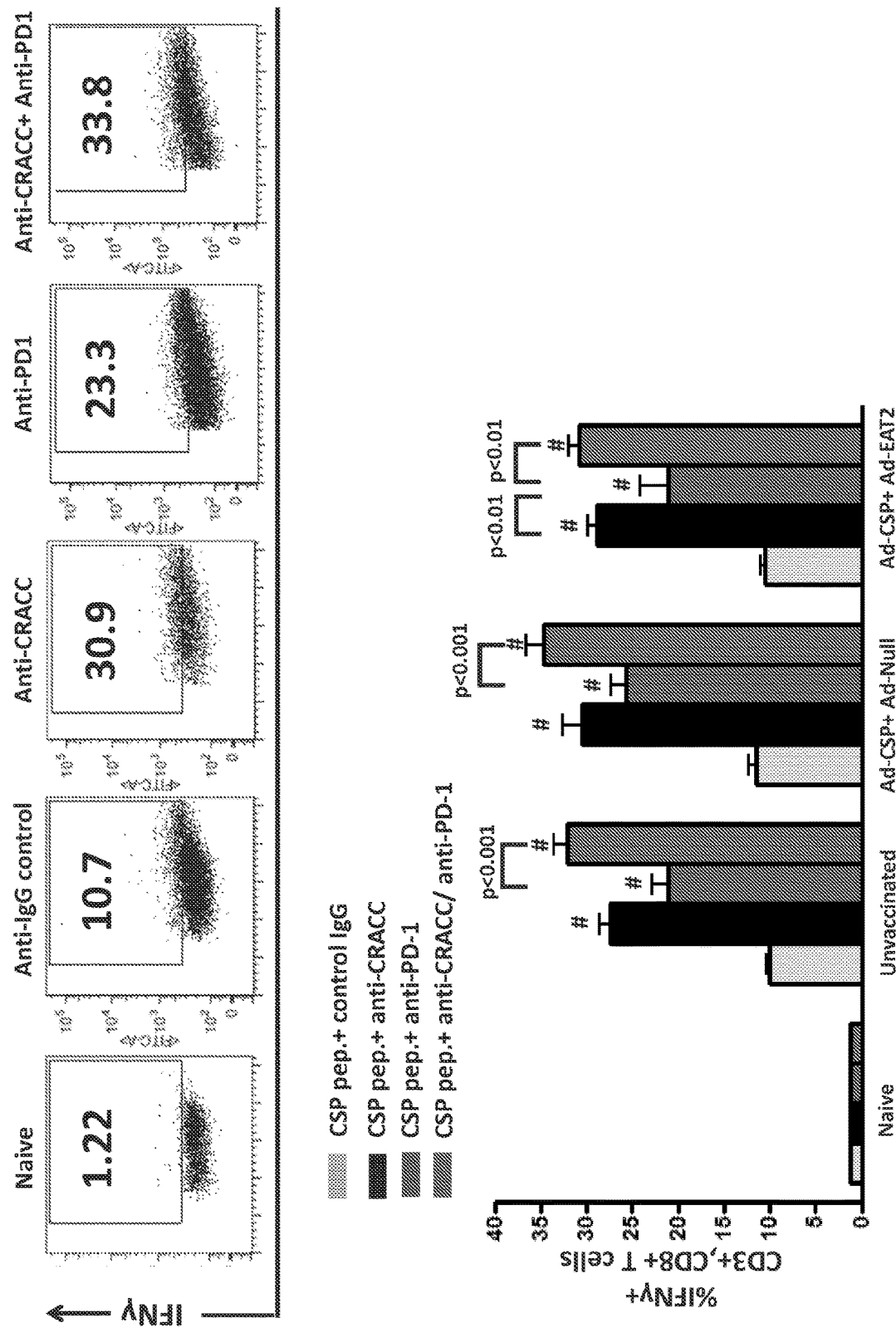
FIG. 16 is a series of flow cytometry histograms, and an associated bar graph summarizing the results set forth in the dot plots, depicting the percentage of IFNγ-expressing CD3$^+$ CD8$^+$ T cells following exposure to CSP peptide (CSP pep.) in the presence or absence of an anti-CRACC antibody. Splenocytes obtained from mice infected with malaria or non-infected mice were contacted ex vivo with a CSP peptide (CSP pep.) and with an anti-CRACC antibody, an anti-PD-1 antibody, or a control IgG antibody that does not bind to CRACC. The percentage of splenic CD3$^+$CD8$^+$ T cells expressing IFNγ is shown as indicated. # denotes p<0.001 statistically different from mock injected animals.
Figure 17:
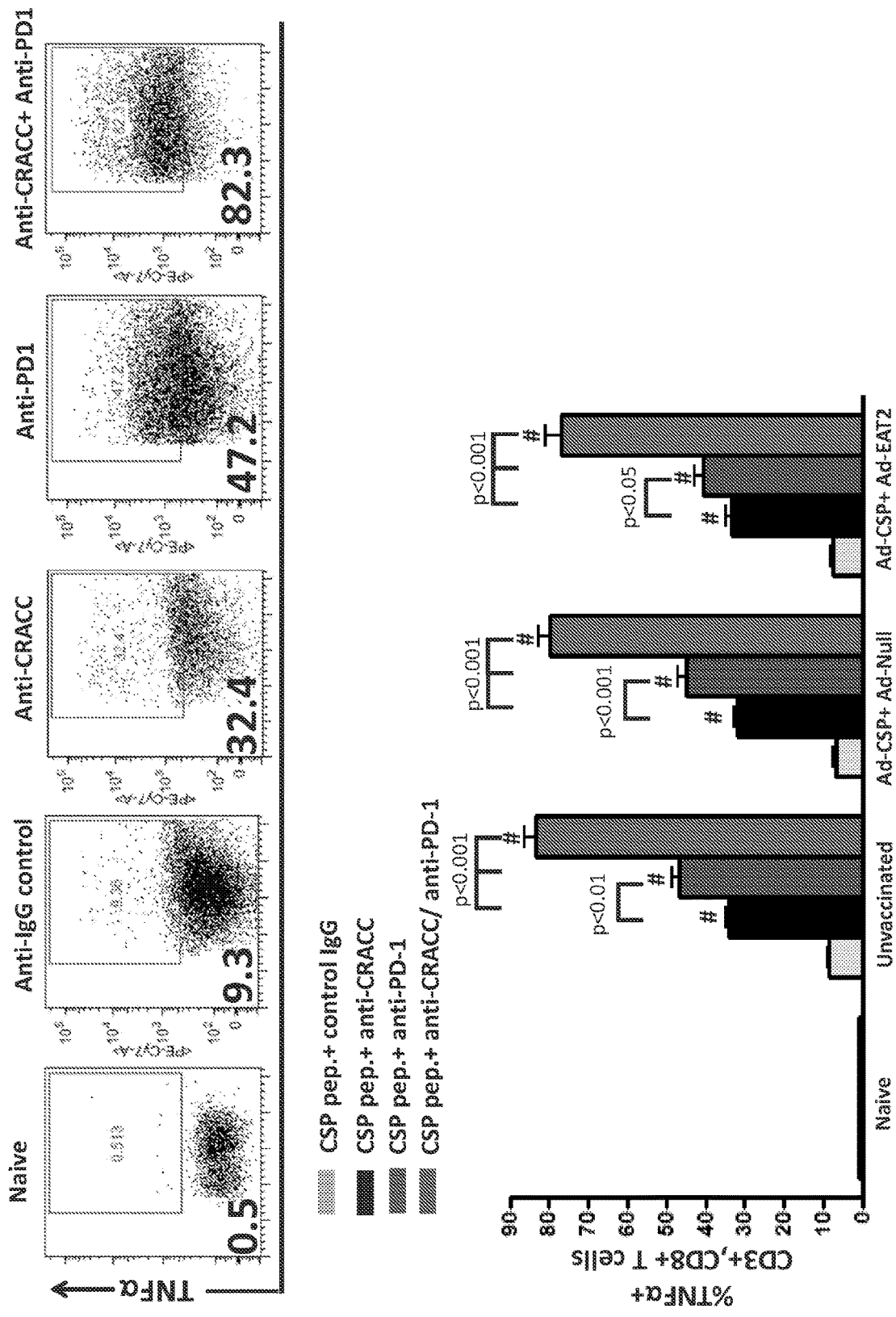
FIG. 17 is a series of flow cytometry histograms, and an associated bar graph summarizing the results set forth in the dot plots, depicting the percentage of TNFα-expressing CD3$^+$CD8$^+$ T cells following exposure to CSP peptide (CSP pep.) in the presence or absence of an anti-CRACC antibody. Splenocytes obtained from mice infected with malaria or non-infected mice were contacted ex vivo with a CSP peptide (CSP pep.) and with an anti-CRACC antibody, an anti-PD-1 antibody, or a control IgG antibody that does not bind to CRACC. The percentage of splenic CD3$^+$CD8$^+$ T cells expressing TNFα is shown as indicated. # denotes p<0.001 statistically different from mock injected animals.

Since malaria infection has been confirmed previously to induce higher expression levels of PD-1 on the surface of T cells, (a feature correlated with T cell exhaustion), and since PD-1-PD-L1 inhibition has been shown to reverse the exhaustion phenotype of those T cells, the following experiments were performed to determine if inhibiting CRACC-CRACC homophilic interactions will induce similar cytokine levels, as compared to PD-1 blocking strategy. Therefore, splenocytes obtained from malaria infected mice (above) were incubated for one hour with either an antagonist anti-PD-1 antibody, an antagonist anti-CRACC antibody, or a control antibody. The cells were then stimulated with CSP-specific peptide and the production of IFNγ, TNFα, and IL-2 was evaluated by FACS analysis. Inhibiting the CRACC-CRACC interaction increased the expression level of these cytokines by CSP-specific CD8$^+$ T cells. These expression levels were similar or higher to the CSP-specific responses that were observed in cell pre-treated with the anti-PD-1 antibody (FIGS. 16, 17, and 18). In addition, even greater enhancement of cytokine expression by CD8$^+$ T cells was observed when the cells were stimulated in the presence of both anti-PD-1 and anti-CRACC antibodies (FIGS. 16, 17, and 18). (These cells expressed both PD-1 and CRACC polypeptides). These results indicate that in vivo inhibition of the PD-1 and CRACC signaling pathways may be beneficial for enhancing CD8$^+$ T cell responses to vaccine antigens.

Figure 19A:
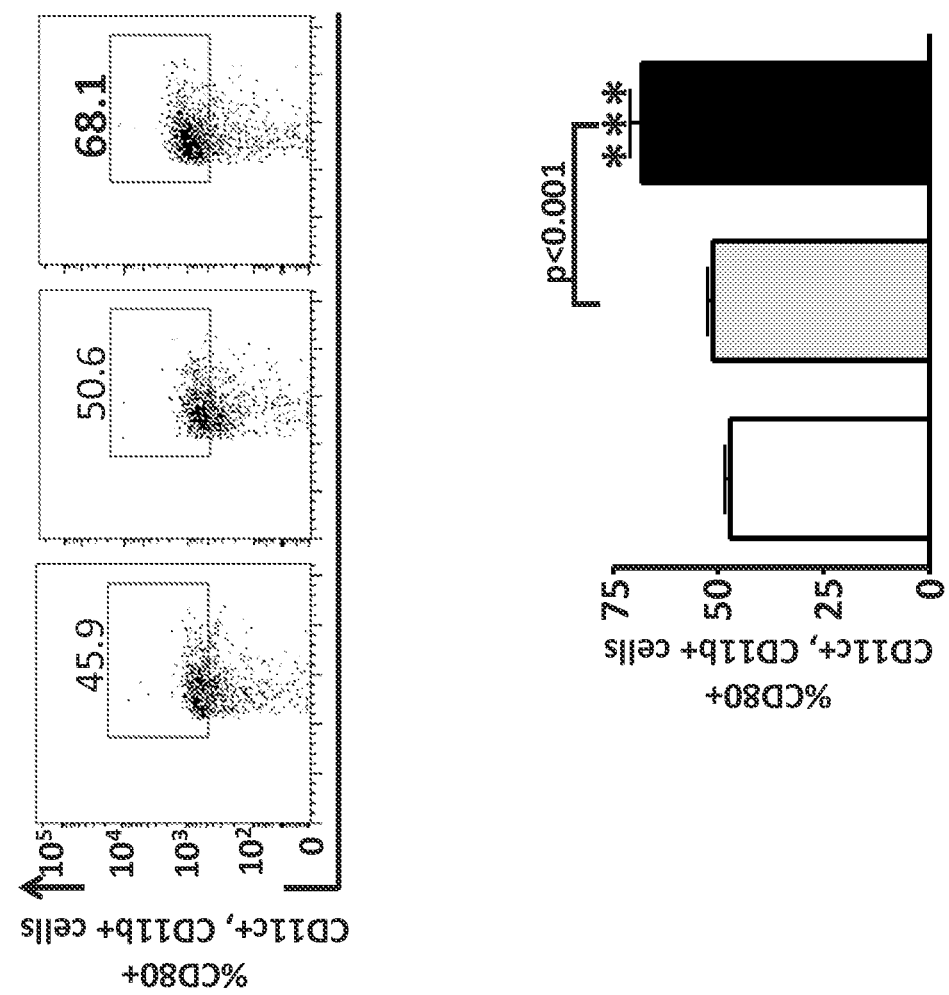
FIGS. 19A, 19B, and 19C are each a series of flow cytometry dot plots, and associated bar graphs summarizing the results set forth in the dot plots, depicting the expression profiles of CD11c+CD11b$^+$ dendritic cells from mice vaccinated with rAd5-Null and CRACC-Fc fusion protein or naïve mice. The percentage of splenic CD11c$^+$CD11b$^+$ dendritic cells expressing CD80 (FIG. 19A), CD86 (FIG. 19B), and MHC-II (FIG. 21C) is shown as indicated. *** denotes p<0.001, statistically different from naive animals.
Figure 19B:
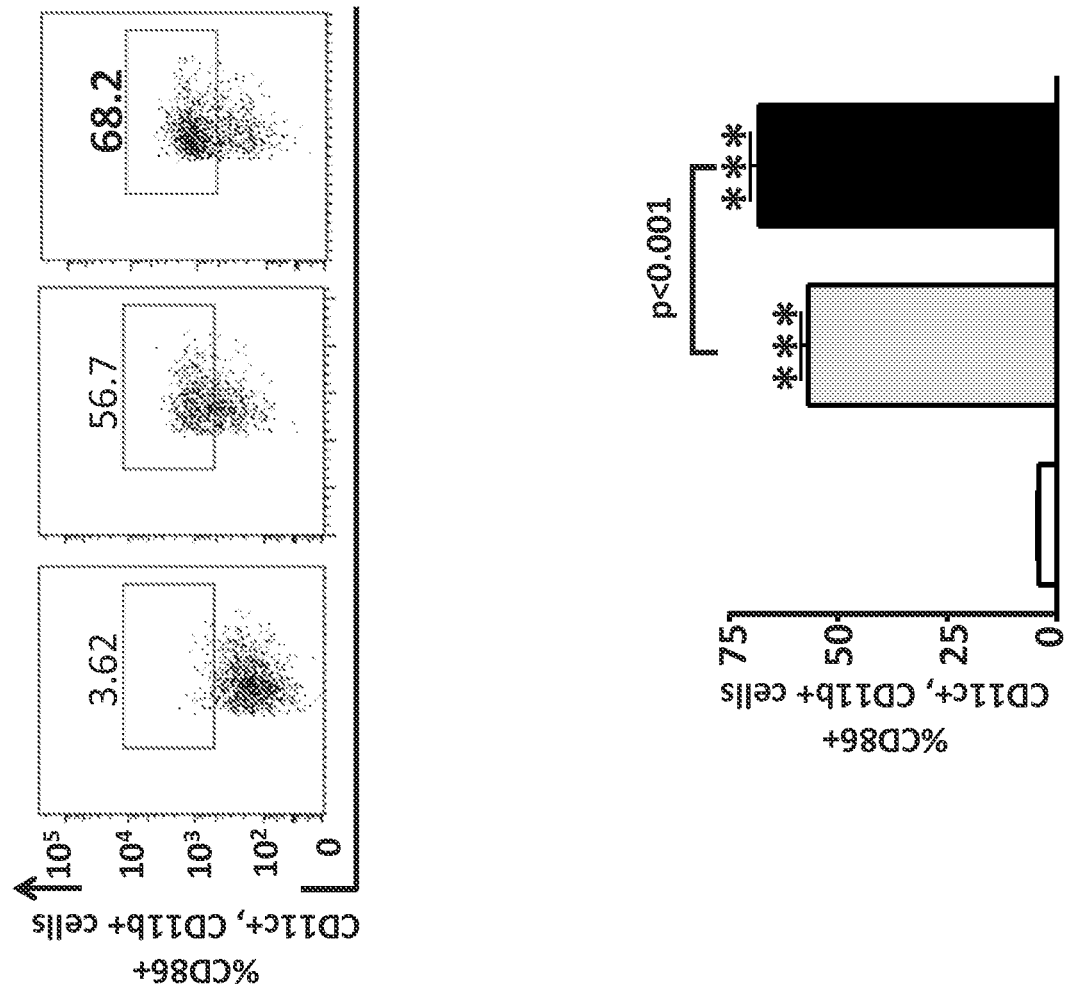
Figure 19C:
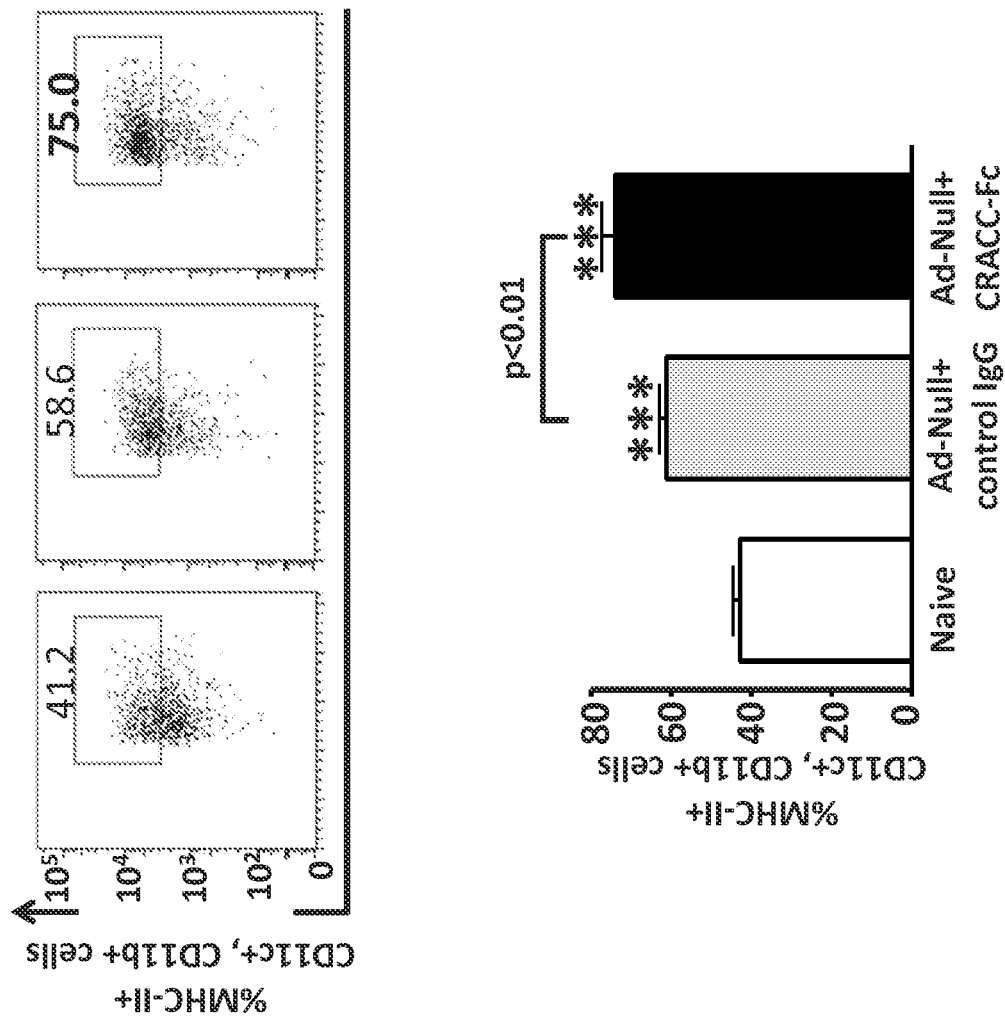

Example 11. Increased Maturation of CD11c+/CD11b+ Double Positive Dendritic Cells in Spleen of CRACC-Fc Fusion Co-Injected Animals The maturational status of dendritic cells was also evaluated following rAd-Null and CRACC-Fc fusion vaccinations of mice (see example 7). Statistically significant increases in the number and concentration of CD11c+ CD11b+ dendritic cells expressing CD80, CD86, and MHC-II were observed in splenocyte populations obtained from mice co-administered rAd-Null virus and CRACC-Fc fusion protein (as compared to mice receiving the virus along with the IgG control antibody). (See FIGS. 19A-19C). These data indicate that inhibition of CRACC-CRACC interactions enhance DC maturation as an early event following administration of the CRACC-Fc protein.

Figure 20:
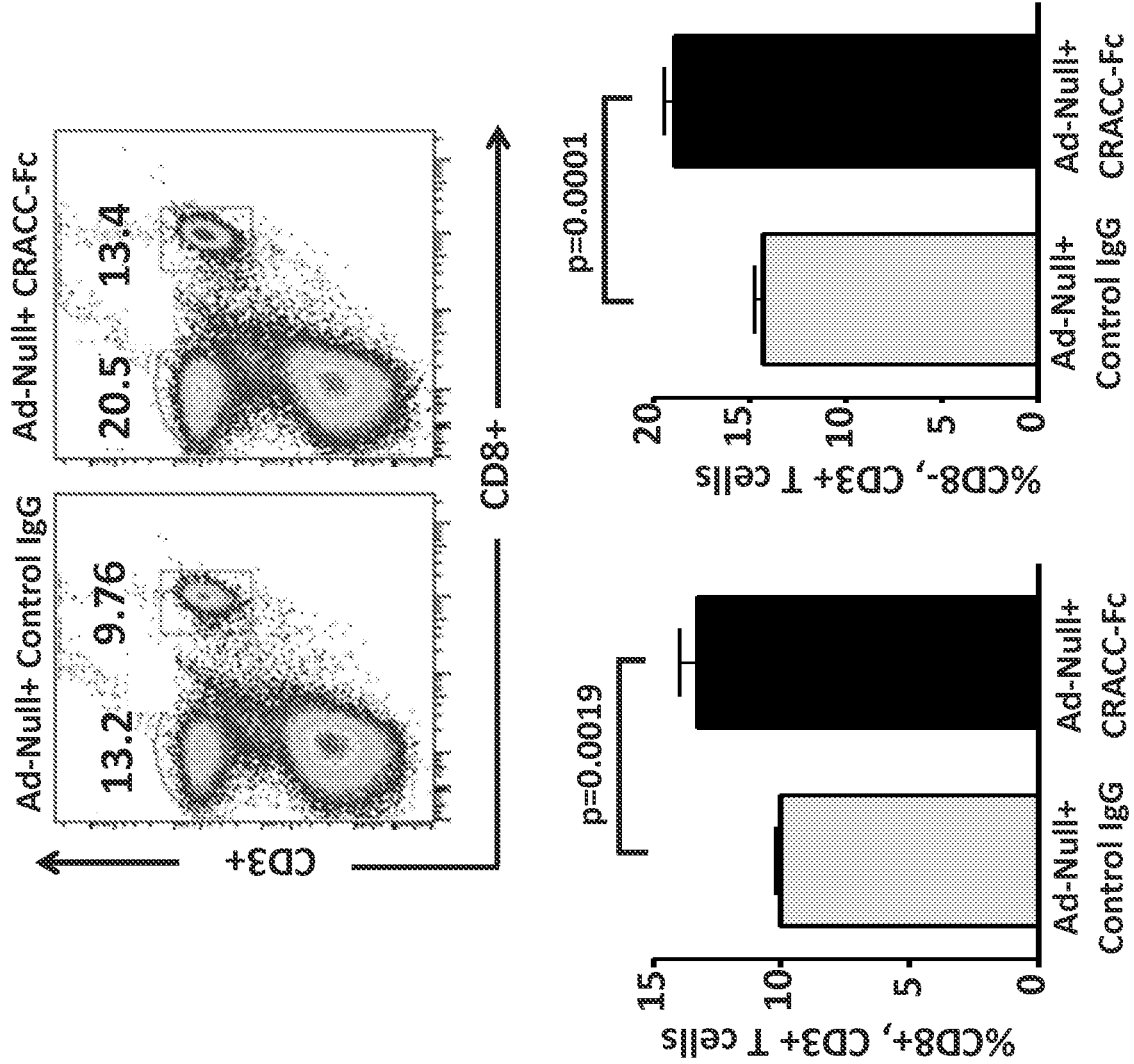
FIG. 20 is a pair of flow cytometry dot plots and a pair of bar graphs depicting increased proliferation of CD3$^+$ and CD8$^+$ T cells in the spleen of CRACC-FC and Ad-Null injected mice. With respect to the dot plots, the percentage of CD3$^+$ (at left in each plot) and CD3$^+$CD8$^+$ double positive (right in each plot) is indicated. These data are also provided in the bar graphs.

Example 12. Co-Administration of CRACC-Fc and Adenovirus Constructs Induces Differential Activation of Adaptive Immune Cells The phenotype of adaptive immune cell (B and T cell) responses were also analyzed following administration of the CRACC-Fc fusion protein to mice. To evaluate T and B cell activation following Ad5 and CRACC-Fc co-vaccination, CRACC-Fc or control IgG antibody was mixed with an empty Ad5 vector (rAd5-Null, $2 \times 10^{10}$ vps/mouse) and I.P. administered into mice. After 12 hours, the activation of splenic ($2 \times 10^6$ cells) T and B cells was evaluated by flow cytometry analysis. Administration of the rAd-Null construct alone induced proliferation/expansion of CD3+CD8+ T cells and CD3+C8− T cells, which proliferation was further enhanced when CRACC-Fc was also administered to the mice (FIG. 20). For example, co-administration of the adenovirus and the CRACC-Fc fusion protein resulted in significant increases in the proliferation of both T cells ($p<0.0001$) and B cells ($p=0.0019$) (FIG. 20). In addition, significantly higher numbers and concentrations of CD69-expressing CD3+CD8+ T cells ($p<0.01$) and CD3+CD8− T cells ($p<0.01$) in splenocyte populations from mice injected with adenovirus and CRACC-Fc fusion protein were also observed (FIGS. 21A and 21B).

Figure 22A:
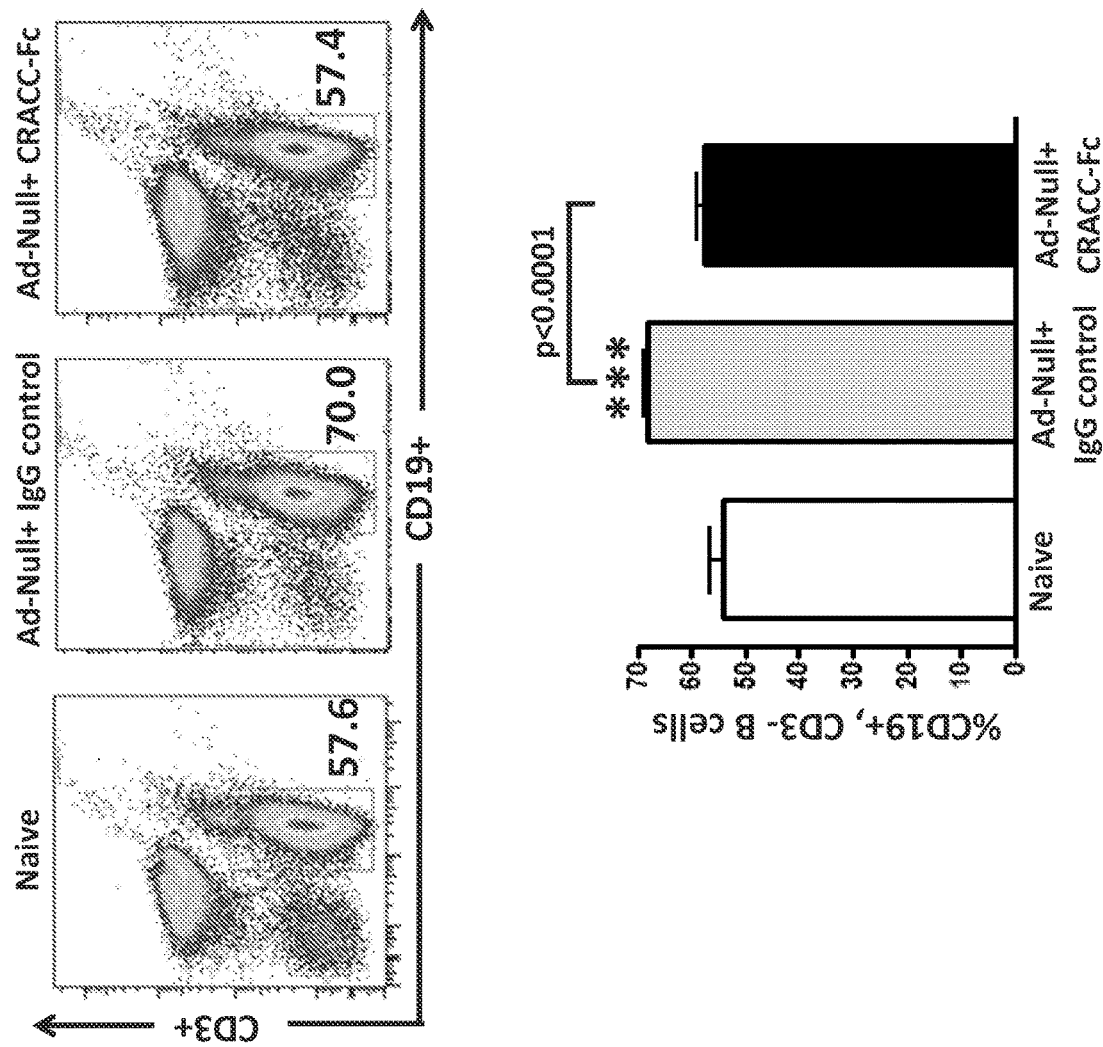
FIGS. 22A and 22B are each a series of flow cytometry dot plots, and associated bar graphs summarizing the results set forth in the dot plots, depicting a reduction in B cell proliferation in mice vaccinated with rAd5-Null and CRACC-Fc fusion protein, relative to mice vaccinated with rAd5-Null and a control antibody.
Figure 22B:
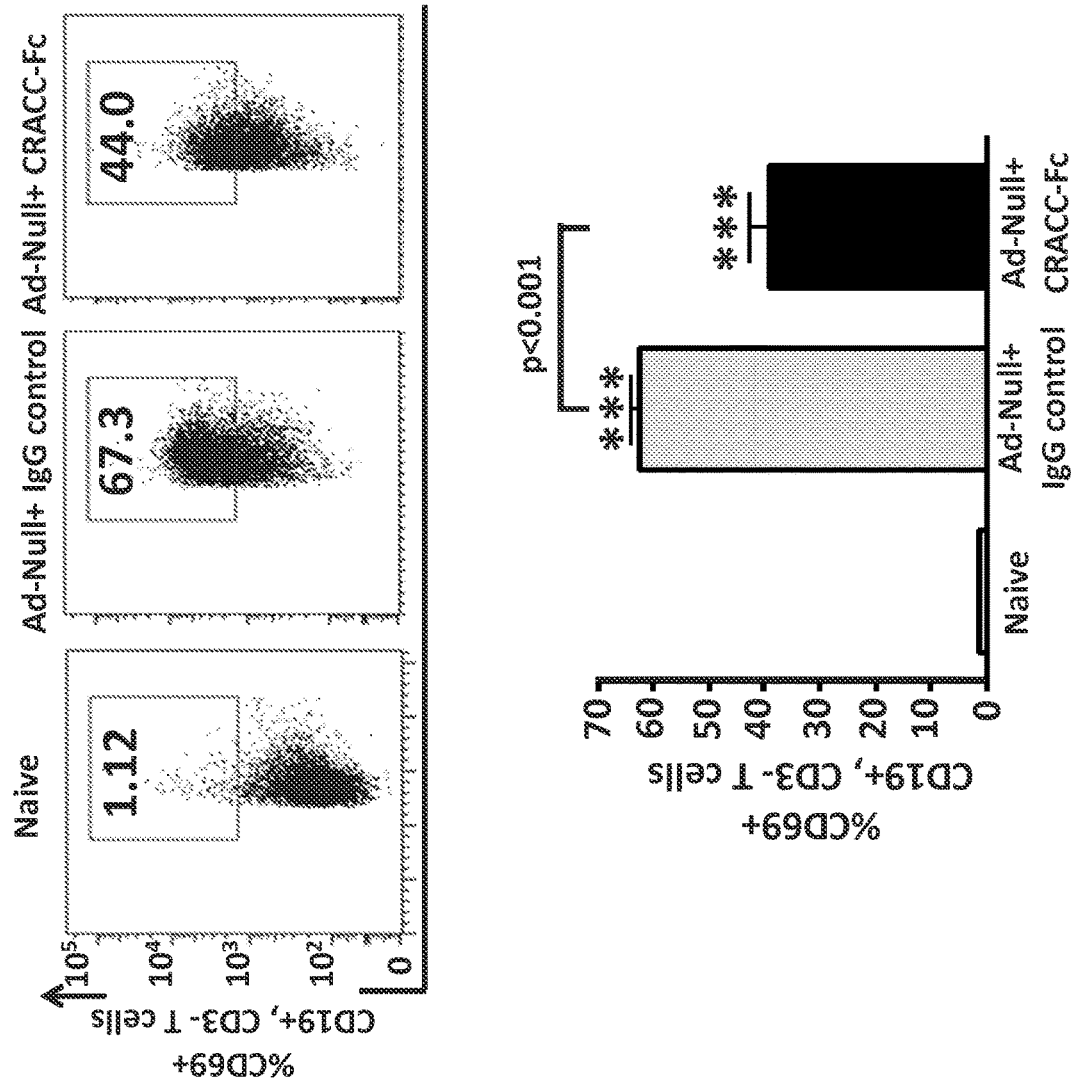

B cell activation (e.g., proliferation and activation (e.g., CD69 expression) following CRACC-Fc and rAd-Null virus co-injection, however, was significantly reduced, as compared to the level of activation of B cell from mice co-injected with rAd-Null virus and the IgG antibody control (FIGS. 22A and 22B). These data indicate that inhibition of CRACC-CRACC homophilic interactions in conjunction with a vaccination regimen alters B cell responses early after administration.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

---

What we claim is:

1. A therapeutic kit comprising: (a) an antigen and (b) an agent that inhibits the interaction between a first CRACC protein and a second CRACC protein, wherein the agent is a protein comprising the amino acid sequence of SEQ ID NO: 170.

2. A composition comprising an agent that inhibits the interaction between a first CRACC protein and a second CRACC protein, wherein the agent is a protein comprising the amino acid sequence of SEQ ID NO: 170.

3. The composition of claim 2, wherein the composition comprises an antigen.

* * * * *

SEQUENCE LISTING

```
<160> NUMBER OF SEQ ID NOS: 173

<210> SEQ ID NO 1
<211> LENGTH: 335
<212> TYPE: PRT
<213> ORGANISM: Homo sapiens

<400> SEQUENCE: 1

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160
```

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 2
<211> LENGTH: 261
<212> TYPE: PRT
<213> ORGANISM: Homo sapiens

<400> SEQUENCE: 2

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
                20                  25                  30

Phe Asn Thr Thr Pro Leu Val Thr Ile Gln Pro Glu Gly Gly Thr Ile
            35                  40                  45

Ile Val Thr Gln Asn Arg Asn Arg Glu Arg Val Asp Phe Pro Asp Gly
    50                  55                  60

Gly Tyr Ser Leu Lys Leu Ser Lys Leu Lys Lys Asn Asp Ser Gly Ile
65                  70                  75                  80

Tyr Tyr Val Gly Ile Tyr Ser Ser Ser Leu Gln Gln Pro Ser Thr Gln
                85                  90                  95

Glu Tyr Val Leu His Val Tyr Glu His Leu Ser Lys Pro Lys Val Thr
            100                 105                 110

Met Gly Leu Gln Ser Asn Lys Asn Gly Thr Cys Val Thr Asn Leu Thr
        115                 120                 125

Cys Cys Met Glu His Gly Glu Glu Asp Val Ile Tyr Thr Trp Lys Ala
    130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                165                 170                 175

Asn Pro Val Ser Arg Asn Phe Ser Ser Pro Ile Leu Ala Arg Lys Leu
            180                 185                 190

Cys Glu Gly Ala Ala Asp Asp Pro Asp Ser Ser Met Ala Ala Asn Glu

```
                195                 200                 205
Ser His Asn Gly Ser Ile Leu Pro Ile Ser Trp Arg Trp Gly Glu Ser
    210                 215                 220

Asp Met Thr Phe Ile Cys Val Ala Arg Asn Pro Val Ser Arg Asn Phe
225                 230                 235                 240

Ser Ser Pro Ile Leu Ala Arg Lys Leu Cys Glu Gly Ala Ala Asp Asp
            245                 250                 255

Pro Asp Ser Ser Met
            260

<210> SEQ ID NO 3
<211> LENGTH: 335
<212> TYPE: PRT
<213> ORGANISM: Macaca mulatta

<400> SEQUENCE: 3

Met Ala Gly Ser Pro Thr Cys Phe Thr Phe Ile Tyr Ile Leu Trp Gln
1               5                   10                  15

Leu Thr Gly Ser Thr Ala Ser Gly Ser Val Lys Glu Leu Val Gly Ser
            20                  25                  30

Ile Gly Gly Ala Val Thr Phe Pro Leu Lys Ser Glu Val Lys Gln Val
        35                  40                  45

Asp Ser Ile Val Trp Thr Phe Asn Thr Thr Leu Val Thr Ile Gln
50                  55                  60

Pro Glu Gly Gly Pro Met Ile Val Thr Gln Asn Arg Asn Lys Glu Arg
65                  70                  75                  80

Val His Phe Pro Asp Gly Gly Tyr Ser Leu Lys Leu Ser Lys Leu Lys
                85                  90                  95

Lys Asn Asp Ser Gly Ile Tyr Asn Val Glu Ile Tyr Ser Ser Ser Leu
            100                 105                 110

Gln Asp Pro Phe Thr Arg Lys Tyr Val Leu Arg Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys His Met Glu His Gly Glu Glu Asp Val
145                 150                 155                 160

Ile Tyr Thr Trp Lys Ala Leu Gly Gln Ala Val Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Thr Val Arg Asn Pro Val Ser Asn Ser Ser Ser Pro
        195                 200                 205

Ile Leu Ala Arg Lys Leu Cys Glu Gly Ala Ala Asp Asp Ser Asp Ser
    210                 215                 220

Ser Met Val Leu Leu Cys Leu Leu Val Pro Leu Leu Ser Leu
225                 230                 235                 240

Phe Val Leu Gly Leu Phe Leu Trp Phe Leu Lys Arg Glu Thr Gln Glu
                245                 250                 255

Glu Ser Ile Glu Glu Lys Lys Arg Ala Asp Ile Cys Arg Glu Thr Pro
            260                 265                 270

Asn Ile Cys Pro Tyr Ser Gly Glu Asn Thr Glu Tyr Asp Thr Ile Pro
        275                 280                 285

Tyr Thr Asn Arg Thr Ile Pro Met Glu Asp Ala Ala Asn Thr Leu Tyr
    290                 295                 300
```

Ser Thr Val Glu Ile Pro Lys Lys Ile Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 4
<211> LENGTH: 335
<212> TYPE: PRT
<213> ORGANISM: Pan troglodytes

<400> SEQUENCE: 4

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Arg Glu Leu Val Gly Ser
                20                  25                  30

Val Gly Gly Ala Val Thr Phe Pro Leu Lys Ser Lys Val Lys Gln Val
            35                  40                  45

Asp Ser Ile Val Trp Thr Phe Asn Thr Pro Leu Val Thr Ile Gln
    50                  55                  60

Pro Glu Gly Gly Thr Ile Ile Val Thr Gln Asn Arg Asn Lys Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Leu
                100                 105                 110

Gln Gln Pro Ser Thr Gln Lys Tyr Val Leu His Val Tyr Glu His Leu
            115                 120                 125

Ser Lys Pro Lys Val Thr Met Gly Leu Gln Ser Asn Lys Asn Gly Thr
130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
                180                 185                 190

Phe Ile Cys Val Ala Arg Asn Pro Val Ser Ser Asn Phe Ser Ser Pro
            195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Ser Leu
225                 230                 235                 240

Phe Val Leu Gly Leu Phe Leu Trp Phe Leu Lys Arg Glu Arg Gln Glu
                245                 250                 255

Glu Ser Ile Glu Glu Lys Lys Arg Ala Asp Ile Cys Arg Glu Thr Pro
            260                 265                 270

Asn Ile Cys Pro His Ser Gly Glu Asn Thr Glu Tyr Asp Thr Ile Pro
    275                 280                 285

His Thr Asn Arg Thr Ile Leu Lys Glu Asp Pro Ala Asn Thr Val Tyr
290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 5

<211> LENGTH: 333
<212> TYPE: PRT
<213> ORGANISM: Mus musculus

<400> SEQUENCE: 5

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Leu Ala Met Val Lys
50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

Ser Gly Ala Tyr Arg Ala Glu Ile Tyr Ser Thr Ser Ser Gln Ala Ser
            100                 105                 110

Leu Ile Gln Glu Tyr Val Leu His Val Tyr Lys His Leu Ser Arg Pro
        115                 120                 125

Lys Val Thr Ile Asp Arg Gln Ser Asn Lys Asn Gly Thr Cys Val Ile
130                 135                 140

Asn Leu Thr Cys Ser Thr Asp Gln Asp Gly Glu Asn Val Thr Tyr Ser
145                 150                 155                 160

Trp Lys Ala Val Gly Gln Gly Asp Asn Gln Phe His Asp Gly Ala Thr
                165                 170                 175

Leu Ser Ile Ala Trp Arg Ser Gly Glu Lys Asp Gln Ala Leu Thr Cys
            180                 185                 190

Met Ala Arg Asn Pro Val Ser Asn Ser Phe Ser Thr Pro Val Phe Pro
        195                 200                 205

Gln Lys Leu Cys Glu Asp Ala Ala Thr Asp Leu Thr Ser Leu Arg Gly
    210                 215                 220

Ile Leu Tyr Ile Leu Cys Phe Ser Ala Val Leu Ile Leu Phe Ala Val
225                 230                 235                 240

Leu Leu Thr Ile Phe His Thr Thr Trp Ile Lys Lys Gly Lys Gly Cys
                245                 250                 255

Glu Glu Asp Lys Lys Arg Val Asp Arg His Gln Glu Met Pro Asp Leu
            260                 265                 270

Cys Pro His Leu Glu Glu Asn Ala Asp Tyr Asp Thr Ile Pro Tyr Thr
        275                 280                 285

Glu Lys Arg Arg Pro Glu Glu Asp Ala Pro Asn Thr Phe Tyr Ser Thr
    290                 295                 300

Val Gln Ile Pro Lys Val Val Lys Ser Pro Ser Ser Leu Pro Ala Lys
305                 310                 315                 320

Pro Leu Val Pro Arg Ser Leu Ser Phe Glu Asn Val Ile
                325                 330

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Asp Tyr Lys Asp Asp Asp Asp Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Pro Tyr Asp Val Pro Asp Tyr Ala
1               5

<210> SEQ ID NO 9
<211> LENGTH: 202
<212> TYPE: PRT
<213> ORGANISM: Mus musculus

<400> SEQUENCE: 9

Ser Gly Thr Leu Lys Lys Val Ala Gly Ala Leu Asp Gly Ser Val Thr
1               5                   10                  15

Phe Thr Leu Asn Ile Thr Glu Ile Lys Val Asp Tyr Val Val Trp Thr
                20                  25                  30

Phe Asn Thr Phe Phe Leu Ala Met Val Lys Asp Gly Val Thr Ser
            35                  40                  45

Gln Ser Ser Asn Lys Glu Arg Ile Val Phe Pro Asp Gly Leu Tyr Ser
    50                  55                  60

Met Lys Leu Ser Gln Leu Lys Lys Asn Asp Ser Gly Ala Tyr Arg Ala
65                  70                  75                  80

Glu Ile Tyr Ser Thr Ser Ser Gln Ala Ser Leu Ile Gln Glu Tyr Val
                85                  90                  95

Leu His Val Tyr Lys His Leu Ser Arg Pro Lys Val Thr Ile Asp Arg
            100                 105                 110

Gln Ser Asn Lys Asn Gly Thr Cys Val Ile Asn Leu Thr Cys Ser Thr
        115                 120                 125

Asp Gln Asp Gly Glu Asn Val Thr Tyr Ser Trp Lys Ala Val Gly Gln
    130                 135                 140

Gly Asp Asn Gln Phe His Asp Gly Ala Thr Leu Ser Ile Ala Trp Arg
145                 150                 155                 160

Ser Gly Glu Lys Asp Gln Ala Leu Thr Cys Met Ala Arg Asn Pro Val
                165                 170                 175

Ser Asn Ser Phe Ser Thr Pro Val Phe Pro Gln Lys Leu Cys Glu Asp
            180                 185                 190

Ala Ala Thr Asp Leu Thr Ser Leu Arg Gly
        195                 200
```

```
<210> SEQ ID NO 10
<211> LENGTH: 288
<212> TYPE: PRT
<213> ORGANISM: Homo sapiens

<400> SEQUENCE: 10

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 11
<211> LENGTH: 9
<212> TYPE: PRT
<213> ORGANISM: Human immunodeficiency virus 1

<400> SEQUENCE: 11

Ala Met Gln Met Leu Lys Glu Thr Ile
1               5

<210> SEQ ID NO 12
<211> LENGTH: 132
<212> TYPE: PRT
<213> ORGANISM: Mus musculus
```

-continued

<400> SEQUENCE: 12

Met Asp Leu Pro Tyr Tyr His Gly Cys Leu Thr Lys Arg Glu Cys Glu
1               5                   10                  15

Ala Leu Leu Lys Gly Gly Val Asp Gly Asn Phe Leu Ile Arg Asp
            20                  25                  30

Ser Glu Ser Val Pro Gly Ala Leu Cys Leu Cys Val Ser Phe Lys Lys
        35                  40                  45

Leu Val Tyr Ser Tyr Arg Ile Phe Arg Glu Lys His Gly Tyr Tyr Arg
    50                  55                  60

Ile Glu Thr Asn Ala His Thr Pro Arg Thr Ile Phe Pro Asn Leu Gln
65                  70                  75                  80

Glu Leu Val Ser Lys Tyr Gly Lys Pro Gly Gln Gly Leu Val Val His
                85                  90                  95

Leu Ser Asn Pro Ile Met Arg Asn Asn Leu Cys Gln Arg Gly Arg Arg
            100                 105                 110

Met Glu Leu Glu Leu Asn Val Tyr Glu Asn Thr Asp Lys Glu Tyr Val
        115                 120                 125

Asp Val Leu Pro
    130

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggattggtg agctcgtcag                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccctgtttc ttgctgtgtg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agaacatcat ccctgcatcc                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacattgggg gtaggaacac                                           20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggcattgttc tctaatgtct ccg                                       23

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctccaggta tatccgagct tc                                        22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccccttccca gctcattcg                                            19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgtgtccata taggtctcct cca                                       23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccctcacact cagatcatct tct                                       23

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctacgacgt gggctacag                                            19

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tagtccttcc tacccccaatt tcc                                              23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 ttggtccta gccactcctt c                                                  21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctccctaaa acagaggcca a                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgcaactggg atgaaagtca c                                                 21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgggactga tctcagggtg                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaagggaacg ggagaatggg                                                   20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgacttgtg ccctcactta g                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagctgggac tctttaccac t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcggggcca tcatttgttt c                                              21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctagaaggg agctgaacat ca                                             22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaatcagggg tacgttctat gcc                                            23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcctgtgcga aatatgacag ac                                             22

```
<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctccaggga acactgtgta tg                                             22

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggttggttat agccggttaa agc                                            23

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcagggatgc taggggttc                                                 20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttcgctgact ttgagtctgc c                                              21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttattctcat tccgatgttg gca                                            23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtgggttgag catttcttga aac                                            23

<210> SEQ ID NO 41
```

```
<211> LENGTH: 15
<212> TYPE: PRT
<213> ORGANISM: Human immunodeficiency virus 1

<400> SEQUENCE: 41

Met Gly Ala Arg Ala Ser Val Leu Ser Gly Gly Lys Leu Asp Ala
1               5                   10                  15

<210> SEQ ID NO 42
<211> LENGTH: 15
<212> TYPE: PRT
<213> ORGANISM: Human immunodeficiency virus 1

<400> SEQUENCE: 42

Ala Ser Val Leu Ser Gly Gly Lys Leu Asp Ala Trp Glu Lys Ile
1               5                   10                  15

<210> SEQ ID NO 43
<211> LENGTH: 15
<212> TYPE: PRT
<213> ORGANISM: Human immunodeficiency virus 1

<400> SEQUENCE: 43

Ser Gly Gly Lys Leu Asp Ala Trp Glu Lys Ile Arg Leu Arg Pro
1               5                   10                  15

<210> SEQ ID NO 44
<211> LENGTH: 15
<212> TYPE: PRT
<213> ORGANISM: Human immunodeficiency virus 1

<400> SEQUENCE: 44

Leu Asp Ala Trp Glu Lys Ile Arg Leu Arg Pro Gly Gly Lys Lys
1               5                   10                  15

<210> SEQ ID NO 45
<211> LENGTH: 15
<212> TYPE: PRT
<213> ORGANISM: Human immunodeficiency virus 1

<400> SEQUENCE: 45

Glu Lys Ile Arg Leu Arg Pro Gly Gly Lys Lys Lys Tyr Arg Leu
1               5                   10                  15

<210> SEQ ID NO 46
<211> LENGTH: 15
<212> TYPE: PRT
<213> ORGANISM: Human immunodeficiency virus 1

<400> SEQUENCE: 46

Leu Arg Pro Gly Gly Lys Lys Lys Tyr Arg Leu Lys His Leu Val
1               5                   10                  15

<210> SEQ ID NO 47
<211> LENGTH: 15
<212> TYPE: PRT
<213> ORGANISM: Human immunodeficiency virus 1

<400> SEQUENCE: 47

Gly Lys Lys Lys Tyr Arg Leu Lys His Leu Val Trp Ala Ser Arg
1               5                   10                  15

<210> SEQ ID NO 48
<211> LENGTH: 15
<212> TYPE: PRT
```

<213> ORGANISM: Human immunodeficiency virus 1

<400> SEQUENCE: 48

Tyr Arg Leu Lys His Leu Val Trp Ala Ser Arg Glu Leu Glu Arg
1               5                   10                  15

<210> SEQ ID NO 49
<211> LENGTH: 15
<212> TYPE: PRT
<213> ORGANISM: Human immunodeficiency virus 1

<400> SEQUENCE: 49

His Leu Val Trp Ala Ser Arg Glu Leu Glu Arg Phe Ala Leu Asn
1               5                   10                  15

<210> SEQ ID NO 50
<211> LENGTH: 15
<212> TYPE: PRT
<213> ORGANISM: Human immunodeficiency virus 1

<400> SEQUENCE: 50

Ala Ser Arg Glu Leu Glu Arg Phe Ala Leu Asn Pro Gly Leu Leu
1               5                   10                  15

<210> SEQ ID NO 51
<211> LENGTH: 14
<212> TYPE: PRT
<213> ORGANISM: Human immunodeficiency virus 1

<400> SEQUENCE: 51

Leu Glu Arg Phe Ala Leu Asn Pro Gly Leu Leu Glu Thr Ser
1               5                   10

<210> SEQ ID NO 52
<211> LENGTH: 15
<212> TYPE: PRT
<213> ORGANISM: Human immunodeficiency virus 1

<400> SEQUENCE: 52

Phe Ala Leu Asn Pro Gly Leu Leu Glu Thr Ser Glu Gly Cys Lys
1               5                   10                  15

<210> SEQ ID NO 53
<211> LENGTH: 15
<212> TYPE: PRT
<213> ORGANISM: Human immunodeficiency virus 1

<400> SEQUENCE: 53

Pro Gly Leu Leu Glu Thr Ser Glu Gly Cys Lys Gln Ile Ile Gly
1               5                   10                  15

<210> SEQ ID NO 54
<211> LENGTH: 15
<212> TYPE: PRT
<213> ORGANISM: Human immunodeficiency virus 1

<400> SEQUENCE: 54

Glu Thr Ser Glu Gly Cys Lys Gln Ile Ile Gly Gln Leu Gln Pro
1               5                   10                  15

<210> SEQ ID NO 55
<211> LENGTH: 15
<212> TYPE: PRT
<213> ORGANISM: Human immunodeficiency virus 1

-continued

<400> SEQUENCE: 55

Gly Cys Lys Gln Ile Ile Gly Gln Leu Gln Pro Ala Leu Gln Thr
1               5                   10                  15

<210> SEQ ID NO 56
<211> LENGTH: 13
<212> TYPE: PRT
<213> ORGANISM: Human immunodeficiency virus 1

<400> SEQUENCE: 56

Ile Ile Gly Gln Leu Gln Pro Ala Leu Gln Thr Gly Ser
1               5                   10

<210> SEQ ID NO 57
<211> LENGTH: 15
<212> TYPE: PRT
<213> ORGANISM: Human immunodeficiency virus 1

<400> SEQUENCE: 57

Gly Gln Leu Gln Pro Ala Leu Gln Thr Gly Ser Glu Glu Leu Arg
1               5                   10                  15

<210> SEQ ID NO 58
<211> LENGTH: 15
<212> TYPE: PRT
<213> ORGANISM: Human immunodeficiency virus 1

<400> SEQUENCE: 58

Pro Ala Leu Gln Thr Gly Ser Glu Glu Leu Arg Ser Leu Tyr Asn
1               5                   10                  15

<210> SEQ ID NO 59
<211> LENGTH: 15
<212> TYPE: PRT
<213> ORGANISM: Human immunodeficiency virus 1

<400> SEQUENCE: 59

Thr Gly Ser Glu Glu Leu Arg Ser Leu Tyr Asn Thr Val Ala Thr
1               5                   10                  15

<210> SEQ ID NO 60
<211> LENGTH: 15
<212> TYPE: PRT
<213> ORGANISM: Human immunodeficiency virus 1

<400> SEQUENCE: 60

Glu Leu Arg Ser Leu Tyr Asn Thr Val Ala Thr Leu Tyr Cys Val
1               5                   10                  15

<210> SEQ ID NO 61
<211> LENGTH: 15
<212> TYPE: PRT
<213> ORGANISM: Human immunodeficiency virus 1

<400> SEQUENCE: 61

Leu Tyr Asn Thr Val Ala Thr Leu Tyr Cys Val His Gln Arg Ile
1               5                   10                  15

<210> SEQ ID NO 62
<211> LENGTH: 14
<212> TYPE: PRT
<213> ORGANISM: Human immunodeficiency virus 1

<400> SEQUENCE: 62

Val Ala Thr Leu Tyr Cys Val His Gln Arg Ile Glu Val Lys
1               5                   10

<210> SEQ ID NO 63
<211> LENGTH: 14
<212> TYPE: PRT
<213> ORGANISM: Human immunodeficiency virus 1

<400> SEQUENCE: 63

Leu Tyr Cys Val His Gln Arg Ile Glu Val Lys Asp Thr Lys
1               5                   10

<210> SEQ ID NO 64
<211> LENGTH: 14
<212> TYPE: PRT
<213> ORGANISM: Human immunodeficiency virus 1

<400> SEQUENCE: 64

Val His Gln Arg Ile Glu Val Lys Asp Thr Lys Glu Ala Leu
1               5                   10

<210> SEQ ID NO 65
<211> LENGTH: 14
<212> TYPE: PRT
<213> ORGANISM: Human immunodeficiency virus 1

<400> SEQUENCE: 65

Arg Ile Glu Val Lys Asp Thr Lys Glu Ala Leu Glu Lys Ile
1               5                   10

<210> SEQ ID NO 66
<211> LENGTH: 15
<212> TYPE: PRT
<213> ORGANISM: Human immunodeficiency virus 1

<400> SEQUENCE: 66

Val Lys Asp Thr Lys Glu Ala Leu Glu Lys Ile Glu Glu Glu Gln
1               5                   10                  15

<210> SEQ ID NO 67
<211> LENGTH: 15
<212> TYPE: PRT
<213> ORGANISM: Human immunodeficiency virus 1

<400> SEQUENCE: 67

Lys Glu Ala Leu Glu Lys Ile Glu Glu Glu Gln Asn Lys Ser Gln
1               5                   10                  15

<210> SEQ ID NO 68
<211> LENGTH: 15
<212> TYPE: PRT
<213> ORGANISM: Human immunodeficiency virus 1

<400> SEQUENCE: 68

Glu Lys Ile Glu Glu Glu Gln Asn Lys Ser Gln Gln Lys Thr Gln
1               5                   10                  15

<210> SEQ ID NO 69
<211> LENGTH: 15
<212> TYPE: PRT
<213> ORGANISM: Human immunodeficiency virus 1

<400> SEQUENCE: 69

Glu Glu Gln Asn Lys Ser Gln Gln Lys Thr Gln Gln Ala Ala Ala
1               5                   10                  15

<210> SEQ ID NO 70
<211> LENGTH: 15
<212> TYPE: PRT
<213> ORGANISM: Human immunodeficiency virus 1

<400> SEQUENCE: 70

Lys Ser Gln Gln Lys Thr Gln Gln Ala Ala Ala Asp Lys Gly Asn
1               5                   10                  15

<210> SEQ ID NO 71
<211> LENGTH: 15
<212> TYPE: PRT
<213> ORGANISM: Human immunodeficiency virus 1

<400> SEQUENCE: 71

Lys Thr Gln Gln Ala Ala Ala Asp Lys Gly Asn Ser Ser Lys Val
1               5                   10                  15

<210> SEQ ID NO 72
<211> LENGTH: 15
<212> TYPE: PRT
<213> ORGANISM: Human immunodeficiency virus 1

<400> SEQUENCE: 72

Ala Ala Ala Asp Lys Gly Asn Ser Ser Lys Val Ser Gln Asn Tyr
1               5                   10                  15

<210> SEQ ID NO 73
<211> LENGTH: 15
<212> TYPE: PRT
<213> ORGANISM: Human immunodeficiency virus 1

<400> SEQUENCE: 73

Lys Gly Asn Ser Ser Lys Val Ser Gln Asn Tyr Pro Ile Val Gln
1               5                   10                  15

<210> SEQ ID NO 74
<211> LENGTH: 15
<212> TYPE: PRT
<213> ORGANISM: Human immunodeficiency virus 1

<400> SEQUENCE: 74

Ser Lys Val Ser Gln Asn Tyr Pro Ile Val Gln Asn Leu Gln Gly
1               5                   10                  15

<210> SEQ ID NO 75
<211> LENGTH: 15
<212> TYPE: PRT
<213> ORGANISM: Human immunodeficiency virus 1

<400> SEQUENCE: 75

Ser Gln Asn Tyr Pro Ile Val Gln Asn Leu Gln Gly Gln Met Val
1               5                   10                  15

<210> SEQ ID NO 76
<211> LENGTH: 15
<212> TYPE: PRT
<213> ORGANISM: Human immunodeficiency virus 1

<400> SEQUENCE: 76

Pro Ile Val Gln Asn Leu Gln Gly Gln Met Val His Gln Ala Ile
1               5                   10                  15

```
<210> SEQ ID NO 77
<211> LENGTH: 15
<212> TYPE: PRT
<213> ORGANISM: Human immunodeficiency virus 1

<400> SEQUENCE: 77

Asn Leu Gln Gly Gln Met Val His Gln Ala Ile Ser Pro Arg Thr
1               5                   10                  15

<210> SEQ ID NO 78
<211> LENGTH: 15
<212> TYPE: PRT
<213> ORGANISM: Human immunodeficiency virus 1

<400> SEQUENCE: 78

Gly Gln Met Val His Gln Ala Ile Ser Pro Arg Thr Leu Asn Ala
1               5                   10                  15

<210> SEQ ID NO 79
<211> LENGTH: 15
<212> TYPE: PRT
<213> ORGANISM: Human immunodeficiency virus 1

<400> SEQUENCE: 79

His Gln Ala Ile Ser Pro Arg Thr Leu Asn Ala Trp Val Lys Val
1               5                   10                  15

<210> SEQ ID NO 80
<211> LENGTH: 15
<212> TYPE: PRT
<213> ORGANISM: Human immunodeficiency virus 1

<400> SEQUENCE: 80

Ser Pro Arg Thr Leu Asn Ala Trp Val Lys Val Ile Glu Glu Lys
1               5                   10                  15

<210> SEQ ID NO 81
<211> LENGTH: 15
<212> TYPE: PRT
<213> ORGANISM: Human immunodeficiency virus 1

<400> SEQUENCE: 81

Leu Asn Ala Trp Val Lys Val Ile Glu Glu Lys Ala Phe Ser Pro
1               5                   10                  15

<210> SEQ ID NO 82
<211> LENGTH: 15
<212> TYPE: PRT
<213> ORGANISM: Human immunodeficiency virus 1

<400> SEQUENCE: 82

Val Lys Val Ile Glu Glu Lys Ala Phe Ser Pro Glu Val Ile Pro
1               5                   10                  15

<210> SEQ ID NO 83
<211> LENGTH: 15
<212> TYPE: PRT
<213> ORGANISM: Human immunodeficiency virus 1

<400> SEQUENCE: 83

Glu Glu Lys Ala Phe Ser Pro Glu Val Ile Pro Met Phe Ser Ala
1               5                   10                  15

<210> SEQ ID NO 84
<211> LENGTH: 15
```

```
<212> TYPE: PRT
<213> ORGANISM: Human immunodeficiency virus 1

<400> SEQUENCE: 84

Phe Ser Pro Glu Val Ile Pro Met Phe Ser Ala Leu Ser Glu Gly
1               5                   10                  15

<210> SEQ ID NO 85
<211> LENGTH: 15
<212> TYPE: PRT
<213> ORGANISM: Human immunodeficiency virus 1

<400> SEQUENCE: 85

Val Ile Pro Met Phe Ser Ala Leu Ser Glu Gly Ala Thr Pro Gln
1               5                   10                  15

<210> SEQ ID NO 86
<211> LENGTH: 15
<212> TYPE: PRT
<213> ORGANISM: Human immunodeficiency virus 1

<400> SEQUENCE: 86

Phe Ser Ala Leu Ser Glu Gly Ala Thr Pro Gln Asp Leu Asn Thr
1               5                   10                  15

<210> SEQ ID NO 87
<211> LENGTH: 15
<212> TYPE: PRT
<213> ORGANISM: Human immunodeficiency virus 1

<400> SEQUENCE: 87

Ser Glu Gly Ala Thr Pro Gln Asp Leu Asn Thr Met Leu Asn Thr
1               5                   10                  15

<210> SEQ ID NO 88
<211> LENGTH: 15
<212> TYPE: PRT
<213> ORGANISM: Human immunodeficiency virus 1

<400> SEQUENCE: 88

Thr Pro Gln Asp Leu Asn Thr Met Leu Asn Thr Val Gly Gly His
1               5                   10                  15

<210> SEQ ID NO 89
<211> LENGTH: 15
<212> TYPE: PRT
<213> ORGANISM: Human immunodeficiency virus 1

<400> SEQUENCE: 89

Leu Asn Thr Met Leu Asn Thr Val Gly Gly His Gln Ala Ala Met
1               5                   10                  15

<210> SEQ ID NO 90
<211> LENGTH: 15
<212> TYPE: PRT
<213> ORGANISM: Human immunodeficiency virus 1

<400> SEQUENCE: 90

Leu Asn Thr Val Gly Gly His Gln Ala Ala Met Gln Met Leu Lys
1               5                   10                  15

<210> SEQ ID NO 91
<211> LENGTH: 15
<212> TYPE: PRT
<213> ORGANISM: Human immunodeficiency virus 1
```

<400> SEQUENCE: 91

Gly Gly His Gln Ala Ala Met Gln Met Leu Lys Asp Thr Ile Asn
1               5                   10                  15

<210> SEQ ID NO 92
<211> LENGTH: 15
<212> TYPE: PRT
<213> ORGANISM: Human immunodeficiency virus 1

<400> SEQUENCE: 92

Ala Ala Met Gln Met Leu Lys Asp Thr Ile Asn Glu Glu Ala Ala
1               5                   10                  15

<210> SEQ ID NO 93
<211> LENGTH: 15
<212> TYPE: PRT
<213> ORGANISM: Human immunodeficiency virus 1

<400> SEQUENCE: 93

Met Leu Lys Asp Thr Ile Asn Glu Glu Ala Ala Glu Trp Asp Arg
1               5                   10                  15

<210> SEQ ID NO 94
<211> LENGTH: 15
<212> TYPE: PRT
<213> ORGANISM: Human immunodeficiency virus 1

<400> SEQUENCE: 94

Thr Ile Asn Glu Glu Ala Ala Glu Trp Asp Arg Leu His Pro Val
1               5                   10                  15

<210> SEQ ID NO 95
<211> LENGTH: 15
<212> TYPE: PRT
<213> ORGANISM: Human immunodeficiency virus 1

<400> SEQUENCE: 95

Glu Ala Ala Glu Trp Asp Arg Leu His Pro Val His Ala Gly Pro
1               5                   10                  15

<210> SEQ ID NO 96
<211> LENGTH: 15
<212> TYPE: PRT
<213> ORGANISM: Human immunodeficiency virus 1

<400> SEQUENCE: 96

Trp Asp Arg Leu His Pro Val His Ala Gly Pro Ile Pro Pro Gly
1               5                   10                  15

<210> SEQ ID NO 97
<211> LENGTH: 14
<212> TYPE: PRT
<213> ORGANISM: Human immunodeficiency virus 1

<400> SEQUENCE: 97

His Pro Val His Ala Gly Pro Ile Pro Pro Gly Gln Met Arg
1               5                   10

<210> SEQ ID NO 98
<211> LENGTH: 15
<212> TYPE: PRT
<213> ORGANISM: Human immunodeficiency virus 1

<400> SEQUENCE: 98

His Ala Gly Pro Ile Pro Pro Gly Gln Met Arg Glu Pro Arg Gly
1               5                   10                  15

<210> SEQ ID NO 99
<211> LENGTH: 15
<212> TYPE: PRT
<213> ORGANISM: Human immunodeficiency virus 1

<400> SEQUENCE: 99

Ile Pro Pro Gly Gln Met Arg Glu Pro Arg Gly Ser Asp Ile Ala
1               5                   10                  15

<210> SEQ ID NO 100
<211> LENGTH: 15
<212> TYPE: PRT
<213> ORGANISM: Human immunodeficiency virus 1

<400> SEQUENCE: 100

Gly Gln Met Arg Glu Pro Arg Gly Ser Asp Ile Ala Gly Thr Thr
1               5                   10                  15

<210> SEQ ID NO 101
<211> LENGTH: 15
<212> TYPE: PRT
<213> ORGANISM: Human immunodeficiency virus 1

<400> SEQUENCE: 101

Glu Pro Arg Gly Ser Asp Ile Ala Gly Thr Thr Ser Thr Leu Gln
1               5                   10                  15

<210> SEQ ID NO 102
<211> LENGTH: 15
<212> TYPE: PRT
<213> ORGANISM: Human immunodeficiency virus 1

<400> SEQUENCE: 102

Ser Asp Ile Ala Gly Thr Thr Ser Thr Leu Gln Glu Gln Ile Ala
1               5                   10                  15

<210> SEQ ID NO 103
<211> LENGTH: 15
<212> TYPE: PRT
<213> ORGANISM: Human immunodeficiency virus 1

<400> SEQUENCE: 103

Gly Thr Thr Ser Thr Leu Gln Glu Gln Ile Ala Trp Met Thr Ser
1               5                   10                  15

<210> SEQ ID NO 104
<211> LENGTH: 15
<212> TYPE: PRT
<213> ORGANISM: Human immunodeficiency virus 1

<400> SEQUENCE: 104

Thr Leu Gln Glu Gln Ile Ala Trp Met Thr Ser Asn Pro Pro Ile
1               5                   10                  15

<210> SEQ ID NO 105
<211> LENGTH: 15
<212> TYPE: PRT
<213> ORGANISM: Human immunodeficiency virus 1

<400> SEQUENCE: 105

Glu Gln Ile Ala Trp Met Thr Ser Asn Pro Pro Ile Pro Val Gly

```
1               5                  10                 15
```

<210> SEQ ID NO 106
<211> LENGTH: 15
<212> TYPE: PRT
<213> ORGANISM: Human immunodeficiency virus 1

<400> SEQUENCE: 106

```
Trp Met Thr Ser Asn Pro Pro Ile Pro Val Gly Glu Ile Tyr Lys
1               5                  10                 15
```

<210> SEQ ID NO 107
<211> LENGTH: 15
<212> TYPE: PRT
<213> ORGANISM: Human immunodeficiency virus 1

<400> SEQUENCE: 107

```
Asn Pro Pro Ile Pro Val Gly Glu Ile Tyr Lys Arg Trp Ile Ile
1               5                  10                 15
```

<210> SEQ ID NO 108
<211> LENGTH: 15
<212> TYPE: PRT
<213> ORGANISM: Human immunodeficiency virus 1

<400> SEQUENCE: 108

```
Pro Val Gly Glu Ile Tyr Lys Arg Trp Ile Ile Leu Gly Leu Asn
1               5                  10                 15
```

<210> SEQ ID NO 109
<211> LENGTH: 15
<212> TYPE: PRT
<213> ORGANISM: Human immunodeficiency virus 1

<400> SEQUENCE: 109

```
Ile Tyr Lys Arg Trp Ile Ile Leu Gly Leu Asn Lys Ile Val Arg
1               5                  10                 15
```

<210> SEQ ID NO 110
<211> LENGTH: 15
<212> TYPE: PRT
<213> ORGANISM: Human immunodeficiency virus 1

<400> SEQUENCE: 110

```
Trp Ile Ile Leu Gly Leu Asn Lys Ile Val Arg Met Tyr Ser Pro
1               5                  10                 15
```

<210> SEQ ID NO 111
<211> LENGTH: 15
<212> TYPE: PRT
<213> ORGANISM: Human immunodeficiency virus 1

<400> SEQUENCE: 111

```
Gly Leu Asn Lys Ile Val Arg Met Tyr Ser Pro Val Ser Ile Leu
1               5                  10                 15
```

<210> SEQ ID NO 112
<211> LENGTH: 15
<212> TYPE: PRT
<213> ORGANISM: Human immunodeficiency virus 1

<400> SEQUENCE: 112

```
Ile Val Arg Met Tyr Ser Pro Val Ser Ile Leu Asp Ile Arg Gln
1               5                  10                 15
```

<210> SEQ ID NO 113
<211> LENGTH: 14
<212> TYPE: PRT
<213> ORGANISM: Human immunodeficiency virus 1

<400> SEQUENCE: 113

Tyr Ser Pro Val Ser Ile Leu Asp Ile Arg Gln Gly Pro Lys
1               5                   10

<210> SEQ ID NO 114
<211> LENGTH: 15
<212> TYPE: PRT
<213> ORGANISM: Human immunodeficiency virus 1

<400> SEQUENCE: 114

Val Ser Ile Leu Asp Ile Arg Gln Gly Pro Lys Glu Pro Phe Arg
1               5                   10                  15

<210> SEQ ID NO 115
<211> LENGTH: 14
<212> TYPE: PRT
<213> ORGANISM: Human immunodeficiency virus 1

<400> SEQUENCE: 115

Asp Ile Arg Gln Gly Pro Lys Glu Pro Phe Arg Asp Tyr Val
1               5                   10

<210> SEQ ID NO 116
<211> LENGTH: 15
<212> TYPE: PRT
<213> ORGANISM: Human immunodeficiency virus 1

<400> SEQUENCE: 116

Arg Gln Gly Pro Lys Glu Pro Phe Arg Asp Tyr Val Asp Arg Phe
1               5                   10                  15

<210> SEQ ID NO 117
<211> LENGTH: 15
<212> TYPE: PRT
<213> ORGANISM: Human immunodeficiency virus 1

<400> SEQUENCE: 117

Lys Glu Pro Phe Arg Asp Tyr Val Asp Arg Phe Phe Lys Thr Leu
1               5                   10                  15

<210> SEQ ID NO 118
<211> LENGTH: 15
<212> TYPE: PRT
<213> ORGANISM: Human immunodeficiency virus 1

<400> SEQUENCE: 118

Arg Asp Tyr Val Asp Arg Phe Phe Lys Thr Leu Arg Ala Glu Gln
1               5                   10                  15

<210> SEQ ID NO 119
<211> LENGTH: 14
<212> TYPE: PRT
<213> ORGANISM: Human immunodeficiency virus 1

<400> SEQUENCE: 119

Asp Arg Phe Phe Lys Thr Leu Arg Ala Glu Gln Ala Thr Gln
1               5                   10

<210> SEQ ID NO 120

```
<211> LENGTH: 15
<212> TYPE: PRT
<213> ORGANISM: Human immunodeficiency virus 1

<400> SEQUENCE: 120

Phe Lys Thr Leu Arg Ala Glu Gln Ala Thr Gln Asp Val Lys Asn
1               5                   10                  15

<210> SEQ ID NO 121
<211> LENGTH: 14
<212> TYPE: PRT
<213> ORGANISM: Human immunodeficiency virus 1

<400> SEQUENCE: 121

Arg Ala Glu Gln Ala Thr Gln Asp Val Lys Asn Trp Met Thr
1               5                   10

<210> SEQ ID NO 122
<211> LENGTH: 15
<212> TYPE: PRT
<213> ORGANISM: Human immunodeficiency virus 1

<400> SEQUENCE: 122

Glu Gln Ala Thr Gln Asp Val Lys Asn Trp Met Thr Asp Thr Leu
1               5                   10                  15

<210> SEQ ID NO 123
<211> LENGTH: 15
<212> TYPE: PRT
<213> ORGANISM: Human immunodeficiency virus 1

<400> SEQUENCE: 123

Thr Gln Asp Val Lys Asn Trp Met Thr Asp Thr Leu Leu Val Gln
1               5                   10                  15

<210> SEQ ID NO 124
<211> LENGTH: 15
<212> TYPE: PRT
<213> ORGANISM: Human immunodeficiency virus 1

<400> SEQUENCE: 124

Lys Asn Trp Met Thr Asp Thr Leu Leu Val Gln Asn Ala Asn Pro
1               5                   10                  15

<210> SEQ ID NO 125
<211> LENGTH: 15
<212> TYPE: PRT
<213> ORGANISM: Human immunodeficiency virus 1

<400> SEQUENCE: 125

Thr Asp Thr Leu Leu Val Gln Asn Ala Asn Pro Asp Cys Lys Thr
1               5                   10                  15

<210> SEQ ID NO 126
<211> LENGTH: 15
<212> TYPE: PRT
<213> ORGANISM: Human immunodeficiency virus 1

<400> SEQUENCE: 126

Leu Val Gln Asn Ala Asn Pro Asp Cys Lys Thr Ile Leu Lys Ala
1               5                   10                  15

<210> SEQ ID NO 127
<211> LENGTH: 15
<212> TYPE: PRT
```

```
<213> ORGANISM: Human immunodeficiency virus 1

<400> SEQUENCE: 127

Ala Asn Pro Asp Cys Lys Thr Ile Leu Lys Ala Leu Gly Pro Gly
1               5                   10                  15

<210> SEQ ID NO 128
<211> LENGTH: 14
<212> TYPE: PRT
<213> ORGANISM: Human immunodeficiency virus 1

<400> SEQUENCE: 128

Cys Lys Thr Ile Leu Lys Ala Leu Gly Pro Gly Ala Thr Leu
1               5                   10

<210> SEQ ID NO 129
<211> LENGTH: 15
<212> TYPE: PRT
<213> ORGANISM: Human immunodeficiency virus 1

<400> SEQUENCE: 129

Ile Leu Lys Ala Leu Gly Pro Gly Ala Thr Leu Glu Glu Met Met
1               5                   10                  15

<210> SEQ ID NO 130
<211> LENGTH: 15
<212> TYPE: PRT
<213> ORGANISM: Human immunodeficiency virus 1

<400> SEQUENCE: 130

Leu Gly Pro Gly Ala Thr Leu Glu Glu Met Met Thr Ala Cys Gln
1               5                   10                  15

<210> SEQ ID NO 131
<211> LENGTH: 15
<212> TYPE: PRT
<213> ORGANISM: Human immunodeficiency virus 1

<400> SEQUENCE: 131

Ala Thr Leu Glu Glu Met Met Thr Ala Cys Gln Gly Val Gly Gly
1               5                   10                  15

<210> SEQ ID NO 132
<211> LENGTH: 15
<212> TYPE: PRT
<213> ORGANISM: Human immunodeficiency virus 1

<400> SEQUENCE: 132

Glu Met Met Thr Ala Cys Gln Gly Val Gly Gly Pro Gly His Lys
1               5                   10                  15

<210> SEQ ID NO 133
<211> LENGTH: 15
<212> TYPE: PRT
<213> ORGANISM: Human immunodeficiency virus 1

<400> SEQUENCE: 133

Ala Cys Gln Gly Val Gly Gly Pro Gly His Lys Ala Arg Val Leu
1               5                   10                  15

<210> SEQ ID NO 134
<211> LENGTH: 15
<212> TYPE: PRT
<213> ORGANISM: Human immunodeficiency virus 1
```

<400> SEQUENCE: 134

Val Gly Gly Pro Gly His Lys Ala Arg Val Leu Ala Glu Ala Met
1               5                   10                  15

<210> SEQ ID NO 135
<211> LENGTH: 15
<212> TYPE: PRT
<213> ORGANISM: Human immunodeficiency virus 1

<400> SEQUENCE: 135

Gly His Lys Ala Arg Val Leu Ala Glu Ala Met Ser Gln Val Thr
1               5                   10                  15

<210> SEQ ID NO 136
<211> LENGTH: 15
<212> TYPE: PRT
<213> ORGANISM: Human immunodeficiency virus 1

<400> SEQUENCE: 136

Arg Val Leu Ala Glu Ala Met Ser Gln Val Thr Asn Ala Ala Ile
1               5                   10                  15

<210> SEQ ID NO 137
<211> LENGTH: 15
<212> TYPE: PRT
<213> ORGANISM: Human immunodeficiency virus 1

<400> SEQUENCE: 137

Glu Ala Met Ser Gln Val Thr Asn Ala Ala Ile Met Met Gln Arg
1               5                   10                  15

<210> SEQ ID NO 138
<211> LENGTH: 15
<212> TYPE: PRT
<213> ORGANISM: Human immunodeficiency virus 1

<400> SEQUENCE: 138

Ser Gln Val Thr Asn Ala Ala Ile Met Met Gln Arg Gly Asn Phe
1               5                   10                  15

<210> SEQ ID NO 139
<211> LENGTH: 15
<212> TYPE: PRT
<213> ORGANISM: Human immunodeficiency virus 1

<400> SEQUENCE: 139

Asn Ala Ala Ile Met Met Gln Arg Gly Asn Phe Lys Gly Gln Arg
1               5                   10                  15

<210> SEQ ID NO 140
<211> LENGTH: 15
<212> TYPE: PRT
<213> ORGANISM: Human immunodeficiency virus 1

<400> SEQUENCE: 140

Met Met Gln Arg Gly Asn Phe Lys Gly Gln Arg Arg Ile Ile Lys
1               5                   10                  15

<210> SEQ ID NO 141
<211> LENGTH: 14
<212> TYPE: PRT
<213> ORGANISM: Human immunodeficiency virus 1

<400> SEQUENCE: 141

Gly Asn Phe Lys Gly Gln Arg Arg Ile Ile Lys Cys Phe Asn
1               5                   10

<210> SEQ ID NO 142
<211> LENGTH: 14
<212> TYPE: PRT
<213> ORGANISM: Human immunodeficiency virus 1

<400> SEQUENCE: 142

Lys Gly Gln Arg Arg Ile Ile Lys Cys Phe Asn Cys Gly Lys
1               5                   10

<210> SEQ ID NO 143
<211> LENGTH: 15
<212> TYPE: PRT
<213> ORGANISM: Human immunodeficiency virus 1

<400> SEQUENCE: 143

Arg Arg Ile Ile Lys Cys Phe Asn Cys Gly Lys Glu Gly His Ile
1               5                   10                  15

<210> SEQ ID NO 144
<211> LENGTH: 14
<212> TYPE: PRT
<213> ORGANISM: Human immunodeficiency virus 1

<400> SEQUENCE: 144

Lys Cys Phe Asn Cys Gly Lys Glu Gly His Ile Ala Arg Asn
1               5                   10

<210> SEQ ID NO 145
<211> LENGTH: 15
<212> TYPE: PRT
<213> ORGANISM: Human immunodeficiency virus 1

<400> SEQUENCE: 145

Asn Cys Gly Lys Glu Gly His Ile Ala Arg Asn Cys Arg Ala Pro
1               5                   10                  15

<210> SEQ ID NO 146
<211> LENGTH: 15
<212> TYPE: PRT
<213> ORGANISM: Human immunodeficiency virus 1

<400> SEQUENCE: 146

Glu Gly His Ile Ala Arg Asn Cys Arg Ala Pro Arg Lys Lys Gly
1               5                   10                  15

<210> SEQ ID NO 147
<211> LENGTH: 14
<212> TYPE: PRT
<213> ORGANISM: Human immunodeficiency virus 1

<400> SEQUENCE: 147

Ala Arg Asn Cys Arg Ala Pro Arg Lys Lys Gly Cys Trp Lys
1               5                   10

<210> SEQ ID NO 148
<211> LENGTH: 14
<212> TYPE: PRT
<213> ORGANISM: Human immunodeficiency virus 1

<400> SEQUENCE: 148

Cys Arg Ala Pro Arg Lys Lys Gly Cys Trp Lys Cys Gly Lys
1               5                   10

<210> SEQ ID NO 149
<211> LENGTH: 15
<212> TYPE: PRT
<213> ORGANISM: Human immunodeficiency virus 1

<400> SEQUENCE: 149

Pro Arg Lys Lys Gly Cys Trp Lys Cys Gly Lys Glu Gly His Gln
1               5                   10                  15

<210> SEQ ID NO 150
<211> LENGTH: 13
<212> TYPE: PRT
<213> ORGANISM: Human immunodeficiency virus 1

<400> SEQUENCE: 150

Gly Cys Trp Lys Cys Gly Lys Glu Gly His Gln Met Lys
1               5                   10

<210> SEQ ID NO 151
<211> LENGTH: 14
<212> TYPE: PRT
<213> ORGANISM: Human immunodeficiency virus 1

<400> SEQUENCE: 151

Trp Lys Cys Gly Lys Glu Gly His Gln Met Lys Asp Cys Thr
1               5                   10

<210> SEQ ID NO 152
<211> LENGTH: 15
<212> TYPE: PRT
<213> ORGANISM: Human immunodeficiency virus 1

<400> SEQUENCE: 152

Gly Lys Glu Gly His Gln Met Lys Asp Cys Thr Glu Arg Gln Ala
1               5                   10                  15

<210> SEQ ID NO 153
<211> LENGTH: 15
<212> TYPE: PRT
<213> ORGANISM: Human immunodeficiency virus 1

<400> SEQUENCE: 153

His Gln Met Lys Asp Cys Thr Glu Arg Gln Ala Asn Phe Leu Gly
1               5                   10                  15

<210> SEQ ID NO 154
<211> LENGTH: 15
<212> TYPE: PRT
<213> ORGANISM: Human immunodeficiency virus 1

<400> SEQUENCE: 154

Asp Cys Thr Glu Arg Gln Ala Asn Phe Leu Gly Lys Ile Trp Pro
1               5                   10                  15

<210> SEQ ID NO 155
<211> LENGTH: 15
<212> TYPE: PRT
<213> ORGANISM: Human immunodeficiency virus 1

<400> SEQUENCE: 155

Arg Gln Ala Asn Phe Leu Gly Lys Ile Trp Pro Ser Asn Lys Gly
1               5                   10                  15

```
<210> SEQ ID NO 156
<211> LENGTH: 15
<212> TYPE: PRT
<213> ORGANISM: Human immunodeficiency virus 1

<400> SEQUENCE: 156

Phe Leu Gly Lys Ile Trp Pro Ser Asn Lys Gly Arg Pro Gly Asn
1               5                   10                  15

<210> SEQ ID NO 157
<211> LENGTH: 15
<212> TYPE: PRT
<213> ORGANISM: Human immunodeficiency virus 1

<400> SEQUENCE: 157

Ile Trp Pro Ser Asn Lys Gly Arg Pro Gly Asn Phe Leu Gln Ser
1               5                   10                  15

<210> SEQ ID NO 158
<211> LENGTH: 15
<212> TYPE: PRT
<213> ORGANISM: Human immunodeficiency virus 1

<400> SEQUENCE: 158

Asn Lys Gly Arg Pro Gly Asn Phe Leu Gln Ser Arg Pro Glu Pro
1               5                   10                  15

<210> SEQ ID NO 159
<211> LENGTH: 15
<212> TYPE: PRT
<213> ORGANISM: Human immunodeficiency virus 1

<400> SEQUENCE: 159

Pro Gly Asn Phe Leu Gln Ser Arg Pro Glu Pro Thr Ala Pro Pro
1               5                   10                  15

<210> SEQ ID NO 160
<211> LENGTH: 15
<212> TYPE: PRT
<213> ORGANISM: Human immunodeficiency virus 1

<400> SEQUENCE: 160

Leu Gln Ser Arg Pro Glu Pro Thr Ala Pro Pro Ala Glu Ser Phe
1               5                   10                  15

<210> SEQ ID NO 161
<211> LENGTH: 14
<212> TYPE: PRT
<213> ORGANISM: Human immunodeficiency virus 1

<400> SEQUENCE: 161

Pro Glu Pro Thr Ala Pro Pro Ala Glu Ser Phe Gly Phe Gly
1               5                   10

<210> SEQ ID NO 162
<211> LENGTH: 15
<212> TYPE: PRT
<213> ORGANISM: Human immunodeficiency virus 1

<400> SEQUENCE: 162

Thr Ala Pro Pro Ala Glu Ser Phe Gly Phe Gly Glu Glu Ile Thr
1               5                   10                  15

<210> SEQ ID NO 163
<211> LENGTH: 15
```

```
<212> TYPE: PRT
<213> ORGANISM: Human immunodeficiency virus 1

<400> SEQUENCE: 163

Ala Glu Ser Phe Gly Phe Gly Glu Glu Ile Thr Pro Ser Pro Lys
1               5                   10                  15

<210> SEQ ID NO 164
<211> LENGTH: 15
<212> TYPE: PRT
<213> ORGANISM: Human immunodeficiency virus 1

<400> SEQUENCE: 164

Gly Phe Gly Glu Glu Ile Thr Pro Ser Pro Lys Gln Glu Pro Lys
1               5                   10                  15

<210> SEQ ID NO 165
<211> LENGTH: 15
<212> TYPE: PRT
<213> ORGANISM: Human immunodeficiency virus 1

<400> SEQUENCE: 165

Glu Ile Thr Pro Ser Pro Lys Gln Glu Pro Lys Asp Lys Glu Pro
1               5                   10                  15

<210> SEQ ID NO 166
<211> LENGTH: 15
<212> TYPE: PRT
<213> ORGANISM: Human immunodeficiency virus 1

<400> SEQUENCE: 166

Ser Pro Lys Gln Glu Pro Lys Asp Lys Glu Pro Pro Leu Thr Ser
1               5                   10                  15

<210> SEQ ID NO 167
<211> LENGTH: 15
<212> TYPE: PRT
<213> ORGANISM: Human immunodeficiency virus 1

<400> SEQUENCE: 167

Glu Pro Lys Asp Lys Glu Pro Pro Leu Thr Ser Leu Lys Ser Leu
1               5                   10                  15

<210> SEQ ID NO 168
<211> LENGTH: 14
<212> TYPE: PRT
<213> ORGANISM: Human immunodeficiency virus 1

<400> SEQUENCE: 168

Lys Glu Pro Pro Leu Thr Ser Leu Lys Ser Leu Phe Gly Asn
1               5                   10

<210> SEQ ID NO 169
<211> LENGTH: 15
<212> TYPE: PRT
<213> ORGANISM: Human immunodeficiency virus 1

<400> SEQUENCE: 169

Pro Leu Thr Ser Leu Lys Ser Leu Phe Gly Asn Asp Pro Leu Ser
1               5                   10                  15

<210> SEQ ID NO 170
<211> LENGTH: 433
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 170

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
            20                  25                  30

Phe Asn Thr Thr Pro Leu Val Thr Ile Gln Pro Glu Gly Gly Thr Ile
        35                  40                  45

Ile Val Thr Gln Asn Arg Asn Arg Glu Arg Val Asp Phe Pro Asp Gly
50                  55                  60

Gly Tyr Ser Leu Lys Leu Ser Lys Leu Lys Lys Asn Asp Ser Gly Ile
65                  70                  75                  80

Tyr Tyr Val Gly Ile Tyr Ser Ser Ser Leu Gln Gln Pro Ser Thr Gln
                85                  90                  95

Glu Tyr Val Leu His Val Tyr Glu His Leu Ser Lys Pro Lys Val Thr
            100                 105                 110

Met Gly Leu Gln Ser Asn Lys Asn Gly Thr Cys Val Thr Asn Leu Thr
        115                 120                 125

Cys Cys Met Glu His Gly Glu Glu Asp Val Ile Tyr Thr Trp Lys Ala
    130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                165                 170                 175

Asn Pro Val Ser Arg Asn Phe Ser Ser Pro Ile Leu Ala Arg Lys Leu
            180                 185                 190

Cys Glu Gly Ala Ala Asp Asp Pro Asp Ser Ser Met Glu Ser Lys Tyr
        195                 200                 205

Gly Pro Pro Cys Pro Pro Cys Pro Ala Pro Glu Phe Glu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser Gln Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Gly Leu Pro Ser Ser Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Gln Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Arg Leu Thr Val Asp Lys

-continued

```
                385                 390                 395                 400
Ser Arg Trp Gln Glu Gly Asn Val Phe Ser Pro Ser Val Met His Glu
                405                 410                 415

Ala Leu His Asn His Tyr Thr Gln Lys Ser Leu Ser Leu Ser Leu Gly
                420                 425                 430

Lys

<210> SEQ ID NO 171
<211> LENGTH: 424
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Ser Gly Thr Leu Lys Lys Val Ala Gly Ala Leu Asp Gly Ser Val Thr
1               5                   10                  15

Phe Thr Leu Asn Ile Thr Glu Ile Lys Val Asp Tyr Val Val Trp Thr
                20                  25                  30

Phe Asn Thr Phe Phe Leu Ala Met Val Lys Lys Asp Gly Val Thr Ser
            35                  40                  45

Gln Ser Ser Asn Lys Glu Arg Ile Val Phe Pro Asp Gly Leu Tyr Ser
        50                  55                  60

Met Lys Leu Ser Gln Leu Lys Lys Asn Asp Ser Gly Ala Tyr Arg Ala
65                  70                  75                  80

Glu Ile Tyr Ser Thr Ser Ser Gln Ala Ser Leu Ile Gln Glu Tyr Val
                85                  90                  95

Leu His Val Tyr Lys His Leu Ser Arg Pro Lys Val Thr Ile Asp Arg
                100                 105                 110

Gln Ser Asn Lys Asn Gly Thr Cys Val Ile Asn Leu Thr Cys Ser Thr
            115                 120                 125

Asp Gln Asp Gly Glu Asn Val Thr Tyr Ser Trp Lys Ala Val Gly Gln
        130                 135                 140

Gly Asp Asn Gln Phe His Asp Gly Ala Thr Leu Ser Ile Ala Trp Arg
145                 150                 155                 160

Ser Gly Glu Lys Asp Gln Ala Leu Thr Cys Met Ala Arg Asn Pro Val
                165                 170                 175

Ser Asn Ser Phe Ser Thr Pro Val Phe Pro Gln Lys Leu Cys Glu Asp
            180                 185                 190

Ala Ala Thr Asp Leu Thr Ser Leu Arg Gly Gly Cys Lys Pro Cys Ile
        195                 200                 205

Cys Thr Val Pro Glu Val Ser Ser Val Phe Ile Phe Pro Pro Lys Pro
210                 215                 220

Lys Asp Val Leu Thr Ile Thr Leu Thr Pro Lys Val Thr Cys Val Val
225                 230                 235                 240

Val Asp Ile Ser Lys Asp Asp Pro Glu Val Gln Phe Ser Trp Phe Val
                245                 250                 255

Asp Asp Val Glu Val His Thr Ala Gln Thr Gln Pro Arg Glu Glu Gln
            260                 265                 270

Phe Asn Ser Thr Phe Arg Ser Val Ser Glu Leu Pro Ile Met His Gln
        275                 280                 285

Asp Trp Leu Asn Gly Lys Glu Phe Lys Cys Arg Val Asn Ser Ala Ala
    290                 295                 300

Phe Pro Ala Pro Ile Glu Lys Thr Ile Ser Lys Thr Lys Gly Arg Pro
```

```
                305                 310                 315                 320
Lys Ala Pro Gln Val Tyr Thr Ile Pro Pro Lys Glu Gln Met Ala
                325                 330                 335
Lys Asp Lys Val Ser Leu Thr Cys Met Ile Thr Asp Phe Phe Pro Glu
                340                 345                 350
Asp Ile Thr Val Glu Trp Gln Trp Asn Gly Gln Pro Ala Glu Asn Tyr
                355                 360                 365
Lys Asn Thr Gln Pro Ile Met Asp Thr Asp Gly Ser Tyr Phe Val Tyr
                370                 375                 380
Ser Lys Leu Asn Val Gln Lys Ser Asn Trp Glu Ala Gly Asn Thr Phe
385                 390                 395                 400
Thr Cys Ser Val Leu His Glu Gly Leu His Asn His His Thr Glu Lys
                405                 410                 415
Ser Leu Ser His Ser Pro Gly Lys
                420

<210> SEQ ID NO 172
<211> LENGTH: 20
<212> TYPE: PRT
<213> ORGANISM: Homo sapiens

<400> SEQUENCE: 172

Met Tyr Arg Met Gln Leu Leu Ser Cys Ile Ala Leu Ser Leu Ala Leu
1               5                   10                  15

Val Thr Asn Ser
            20

<210> SEQ ID NO 173
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Tyr Arg Met Gln Leu Leu Ser Cys Ile Ala Leu Ser Leu Ala Leu
1               5                   10                  15

Val Thr Asn Ser Ser Gly Thr Leu Lys Lys Val Ala Gly Ala Leu Asp
            20                  25                  30

Gly Ser Val Thr Phe Thr Leu Asn Ile Thr Glu Ile Lys Val Asp Tyr
        35                  40                  45

Val Val Trp Thr Phe Asn Thr Phe Phe Leu Ala Met Val Lys Lys Asp
    50                  55                  60

Gly Val Thr Ser Gln Ser Ser Asn Lys Glu Arg Ile Val Phe Pro Asp
65                  70                  75                  80

Gly Leu Tyr Ser Met Lys Leu Ser Gln Leu Lys Lys Asn Asp Ser Gly
                85                  90                  95

Ala Tyr Arg Ala Glu Ile Tyr Ser Thr Ser Ser Gln Ala Ser Leu Ile
            100                 105                 110

Gln Glu Tyr Val Leu His Val Tyr Lys His Leu Ser Arg Pro Lys Val
        115                 120                 125

Thr Ile Asp Arg Gln Ser Asn Lys Asn Gly Thr Cys Val Ile Asn Leu
    130                 135                 140

Thr Cys Ser Thr Asp Gln Asp Gly Glu Asn Val Thr Tyr Ser Trp Lys
145                 150                 155                 160

Ala Val Gly Gln Gly Asp Asn Gln Phe His Asp Gly Ala Thr Leu Ser
```

```
                    165                 170                 175
Ile Ala Trp Arg Ser Gly Glu Lys Asp Gln Ala Leu Thr Cys Met Ala
            180                 185                 190

Arg Asn Pro Val Ser Asn Ser Phe Ser Thr Pro Val Phe Pro Gln Lys
        195                 200                 205

Leu Cys Glu Asp Ala Ala Thr Asp Leu Thr Ser Leu Arg Gly Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
        370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440
```